US008188238B2

(12) United States Patent
Pease et al.

(10) Patent No.: US 8,188,238 B2
(45) Date of Patent: May 29, 2012

(54) RECOMBINANTLY PRODUCED ANTIBODY

(75) Inventors: Larry R Pease, Rochester, MN (US); Virginia Van Keulen, Rochester, MN (US); Bogoljub Ciric, Philadelphia, PA (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 156 days.

(21) Appl. No.: 12/608,390

(22) Filed: Oct. 29, 2009

(65) Prior Publication Data
US 2010/0278816 A1 Nov. 4, 2010

Related U.S. Application Data

(63) Continuation of application No. 10/983,104, filed on Nov. 5, 2004, now abandoned.

(51) Int. Cl.
*C07K 16/00* (2006.01)
*A61K 39/395* (2006.01)
(52) U.S. Cl. .................................. 530/388.1; 424/141.1
(58) Field of Classification Search ........................ None
See application file for complete search history.

(56) References Cited

U.S. PATENT DOCUMENTS

| | | | |
|---|---|---|---|
| 4,946,778 | A | 8/1990 | Ladner et al. |
| 5,591,629 | A | 1/1997 | Rodriguez et al. |
| 2002/0091246 | A1 | 7/2002 | Pardoll et al. |
| 2002/0110836 | A1 | 8/2002 | Freeman et al. |
| 2002/0160000 | A1 | 10/2002 | Wood et al. |
| 2002/0164325 | A1 | 11/2002 | Rodriguez et al. |
| 2002/0164001 | A1 | 11/2002 | Freeman et al. |
| 2002/0182210 | A1 | 12/2002 | Rodriguez et al. |
| 2003/0044768 | A1 | 3/2003 | Wood et al. |
| 2003/0185827 | A1 | 10/2003 | Rodriguez et al. |
| 2003/0211100 | A1 | 11/2003 | Bedian et al. |
| 2004/0014207 | A1 | 1/2004 | Pease et al. |

FOREIGN PATENT DOCUMENTS

| | | |
|---|---|---|
| EP | 1 297 847 | 4/2003 |
| EP | 1 391 464 | 2/2004 |
| JP | 09 100300 | 4/1997 |
| JP | 11 127855 | 5/1999 |
| WO | WO 92/03569 | 3/1992 |
| WO | WO 99/33965 | 7/1999 |
| WO | WO 01/62932 | 8/2001 |
| WO | WO 01/83750 | 11/2001 |
| WO | WO 01/85797 | 11/2001 |
| WO | WO 03/064992 | 8/2003 |
| WO | WO 2004/050683 | 6/2004 |

OTHER PUBLICATIONS

Applicant Information Disclosure.
Nguyen LT et al (2010) J Exp Med 208:901.
Nguyen LT et al (2010) J Immunol 184:6552.
Iijima K et al (2010) J Immunol 184:6553.
Rhadakrishnan S et al (2010) PNAS 107(18):8498.
Rhadakrishnan S et al (2010) J Allergy Clin Immunol 125(5):1173.
Pease LR (2010) FASEB 24: 2135-2136.
Nguyen LT et al (2010) J Immunol 184:6554.
Wiehagen KR et al (2010) J Immunol 184:6555.
Cabrera R et al (2010) J Immunol 184:6556.
Ameson LN et al (2010) J Immunol 184:6557.
Rhadakrishnan S et al (2010) PLoS One 5(3). Doi: 10.137/annotation/36ac4b2c-cf27-41d9-90e25d58d307896.
Matsumoto et al., "B7-DC regulates asthmatic response by an IFN-gamma-dependent mechanism," *J. Immunol.*, 2004, 172(4):2530-2541.
Radhakrishnan et al., "Dendritic cells activated by cross-linking B7-DC (PD-L2) block inflammatory airway disease," *J. Allergy Clin. Immunol.*, 2005, 116(3):668-674.
"Pipeline: PreClinical / R&D Stage" [online]. Acorda Therapeutics, [retrieved on Sep. 8, 2004]. Retrieved from the Internet: <URL: www.acorda.com/pipeline_remyelination.asp>, 2 pages.
Aloisi et al., "Relative efficiency of microglia, astrocytes, dendritic cells and B cells in naïve $CD4^+$T cell priming and Th1/Th2 cell restimulation," *Eur. J. Immunol.*, 1999, 29:2705-2714.
Anjuère et al., "Definition of Dendritic Cell Subpopulations Present in the Spleen, Peyer's Patches, Lymph Nodes, and Skin of the Mouse," *Blood*, 1999, 93(2):590-598.
Asakura et al., "Targeting of $IgM_K$ Antibodies to Oligodendrocytes Promotes CNS Remyelination," *J. Neurosci.*, 1998, 18(19):7700-7708.
Banchereau and Steinman, "Dendritic cells and the control of immunity," *Nature*, 1998, 392:245-252.
Banchereau et al., "Immunology of Dendritic Cells," *Annu. Rev. Immunol.*, 2000, 18:767-811.
Bieber et al., "Humoral autoimmunity 24(11):S39-S44 as a mediator of CNS repair," *Trends in Neurosci.*, 2001,24(11):S39-S44.
Block et al., "Monomeric Class I Molecules Mediate TCR/CD3e/CD8 Interaction on the Surface of T Cells," *J. Immunol.*, 2001, 167:821-826.
Caux et al., "$CD34^+$Hematopoietic Progenitors from Human Cord Blood Differentiate Along Two Independent Dendritic Cell Pathways in Response to GM-CSF+ TNFα," *J. Exp. Med.*, 1996, 184:695-706.
Chen et al., "Tumor Immunogenicity Determines the Effect of B7 Costimulation on T Cell-mediated Tumor Immunity," *J. Exp. Med.*, 1994, 179:523-532.
Ciric et al., "Clonal evolution in Waldenstrom macroglobulinemia highlights functional role of B-cell receptor," *Blood*, 2001, 97:321-323.
Cole et al., "The EBV-Hybridoma Technique and Its Application to Human Lung Cancer," *Monoclonal Antibodies and Cancer Therapy*, 1985, Alan R. Liss, Inc., pp. 77-96.
Cote et al., "Generation of human monoclonal antibodies reactive with cellular antigens," *Proc. Natl. Acad. Sci. USA*, 1983, 80:2026-2030.
Critchfield et al., "T Cell Deletion in High Antigen Dose Therapy of Autoimmune Encephalomyelitis," *Science*, 1994, 263:1139-1143.
Earnshaw et al., "Mammalian Caspases: Structure, Activation, Substrates, and Functions During Apoptosis," *Annu. Rev. Biochem.*, 1999, 68:383-424.
Fagnoni et al., "Role of B70/B7-2 in $CD4^+$T-cell immune responses induced by dendritic cells," *Immunology*, 1995, 85:467-474.

(Continued)

*Primary Examiner* — Ilia Ouspenski
(74) *Attorney, Agent, or Firm* — Klauber & Jackson, LLC

(57) ABSTRACT

An antibody capable of potentiating immune responses and modifying existing states of immune responsiveness is described, as is the sequence of the antibody. Also described are compositions containing the antibody, as well as methods for using the antibody and the compositions to enhance immune responses, to enhance DC function, to modify an existing state of immune responsiveness, to immunize individuals, or to treat or inhibit conditions such as allergic asthma.

6 Claims, 26 Drawing Sheets

OTHER PUBLICATIONS

Fong and Engleman, "Dendritic Cells in Cancer Immunotherapy," *Annu. Rev. Immunol.*, 2000, 18:245-273.

Gallucci and Matzinger, "Danger signals: SOS to the immune system," *Curr. Opin. Immunol.*, 2001, 13:114-119.

Gallucci et al., "Natural adjuvants: Endogenous activators of dendritic cells," *Nat. Med.*, 1999, 5(11):1249-1255.

Granucci et al., "Transcriptional reprogramming of dendritic cells by differentiation stimuli," *Eur. J. Immunol.*, 2001, 31:2539-2546.

Greenwald et al., "Negative co-receptors on lymphocytes," *Curr. Opin. Immunol.*, 2002, 14:391-396.

Gunzer et al., "Antigen Presentation in Extracellular Matrix: Interactions of T Cells with Dendritic Cells Are Dynamic, Short Lived, and Sequential," *Immunity*, 2000, 13:323-332.

Hogquist et al., "T Cell Receptor Antagonist Peptides Induce Positive Selection," *Cell* 1994, 76:17-27.

Holt and Schon-Hegrad, "Localization of T cells, macrophages and dendritic cells in rat respiratory tract tissue: implications for immune function studies," *Immunol.*, 1987, 62:349-356.

Humphrey et al., "The origin of follicular dendritic cells in the mouse and the mechanism of trapping of immune complexes on them," *Eur. J. Immunol.*, 1984, 14:859-864.

Huse et al., "Generation of a Large Combinatorial Library of the Immunoglobulin Repertoire in Phage Lambda," *Science*, 1989, 246:1275-1281.

Inaba et al., "High Levels of a Major Histocompatibility Complex II-Self Peptide Complex on Dendritic Cells from the T Cell Areas of Lymph Nodes," *J. Exp. Med.*, 1997, 186(5):665-672.

Ingulli et al., "In Vivo Detection of Dendritic Cell Antigen Presentation to $CD4^+$ T Cells," *J. Exp. Med.*, 1997, 185(12):2133-2141.

Jacobson et al., "Interleukin 12 Signaling in T Helper Type 1 (Th1) Cells Involves Tyrosine Phosphorylation of Signal Transducer and Activator of Transcription (Stat)3 and Stat4," *J. Exp. Med.*, 1995, 181:1755-1762.

Johnson et al., "Prevalent Class I-Restricted T-Cell Response to the Theiler's Virus Epitope $D^b$:$VP2_{121-130}$ in the Absence to Endogenous CD4 Help, Tumor Necrosis Factor Alpha, Gamma Interferon, Perforin, or Costimulation through CD28," *J. Virol.*, 1999, 73(5):3702-3708.

Johnson et al., "Preservation of motor function by inhibition of CD8+ virus peptide-specific T cells in Theiler's virus infection," *FASEB J.*, 2001, 15:2760-2762.

Josien et al., "TRANCE, a Tumor Necrosis Factor Family Member, Enhances the Longevity and Adjuvant Properties of Dendritic Cells in Vivo," *J. Exp. Med.*, 2000, 191(3):495-501.

Kanto et al., "Ceramide Mediates Tumor-Induced Dendritic Cell Apoptosis," *J. Immunol.*, 2001, 167:3773-3784.

Kaplan et al., "Impaired IL-12 responses and enhanced development of Th2 cells in Stat4-deficient mice," *Nature* 1996, 382:174-177.

Klein et al., "Expressed human immunoglobulin χ genes and their hypermutation," *Eur. J. Immunol.*, 1993, 23:3248-3271.

Koch et al., "Effective Enrichment of Murine Epidermal Langerhans Cells by a Modified (Mismatched) Panning Technique," *J. Invest. Dermatol.*, 1992, 99:803-807.

Köhler and Milstein, "Continuous cultures of fused cells secreting antibody of predefined specificity," *Nature*, 1975, 256:495-497.

Kozbor and Roder, "The production of monoclonal antibodies from human lymphocytes," *Immunology Today*, 1983, 4(3):72-79.

Lang et al., "Isolation and Characterization of a Human Monoclonal Antibody That Recognizes Epitopes Shared by *Pseudomonas aeruginosa* Immunotype 1, 3, 4, and 6 Lipopolysaccharides," *Infection and Immunity*, 1989, 57(12):3851-3855.

Latclunan et al., "PD-L2 is a second ligand for PD-1 and inhibits T cell activation," *Nat. Immunol.*, 2001, 2(3):261-268.

Leenen et al., "Heterogeneity of Mouse Spleem Dendritic Cells: In Vivo Phagocytic Activity, Expression of Macrophage Markers, and Subpopulation Turnover," *J. Immunol.*, 1998, 160:2166-2173.

Lehninger, *Biochemistry*, 1975, 2nd edition, pp. 73-75.

Liang and Sha, "The right place at the right time: novel B7 family members regulate effector T cell responses," *Curr. Opin. Immunol.*, 2002, 14:384-390.

Lu et al., "Increased Apoptosis of Immunoreactive Host Cells and Augmented Donor Leukocyte Chimerism, Not Sustained Inhibition of B7 Molecule Expression are Associated with Prolonged Cardiac Allograft Survival in Mice Preconditioned with Immature Donor Dendritic Cells Plus Anti-CD4OL mAb," *Transplantation*, 1999, 68(6):747-757.

Lutz et al., "An advanced culture method for generating large quantities of highly pure dendritic cells from mouse bone marrow," *J. Immunol. Meth.*, 1999, 223:77-92.

Macatonia et al., "Dendritic Cells Product IL-12 and Direct the Development of Th1 Cells from Naïve $CD4^+$ T Cells," *J. Immunol.*, 1995, 154:5071-5079.

Maldonado-López et al., "$CD8\alpha^+$ and $CD8\alpha^-$ Subclasses of Dendritic Cells Direct the Development of Distinct T Helper Cells in Vivo," *J. Exp. Med.*, 1999, 189(3):587-592.

Maraskovsky et al., "Dramatic Increase in the Numbers Of Functionally Mature Dendritic Cells in Flt3 Ligand-treated Mice: Multiple Dendritic Cell Subpopulations Identified," *J. Exp. Med.*, 1996, 184:1953-1962.

Matsue et al., "Dendritic Cells Undergo Rapid Apoptosis in Vitro During Antigen-Specific Interaction with $CD4^+$ T Cells," *J. Immunol.*, 1999, 162:5287-5298.

Mayordomo et al., "Bone marrow-derived dendritic cells pulsed with synthetic tumour peptides elicit protective and therapeutic antitumour immunity," *Nat. Med.*, 1995, 1(12):1297-1302.

Miller et al., "Monoclonal Autoantibodies Promote Central Nervous System Repair in an Animal Model of Multiple Sclerosis," *J. Neurosci.*, 1994, 14(10):6230-6238.

Miller et al., "Multi-organ Reactivity of a Monoclonal Natural Autoantibody That Promotes Remyelination in a Mouse Model of Multiple Sclerosis," *J. Histochem. Cytochem.*, 1996, 44(9):1005-1011.

Mitsunaga et al., "Direct evidence that a human antibody derived from patient serum can promote myelin repair in a mouse model of chronic-progressive demyelinating disease," *FASEB J.*, 2002, 16(10):1325-1327.

Monks et al., "Three-dimensional segregation of supramolecular activation clusters in T cells," *Nature*, 1998, 395:82-86.

Murphy et al., "Induction by Antigen of Intrathymic Apoptosis of $CD4^+CD8^+TCR^{10}$ Thymocytes in Vivo," *Science*, 1990, 250:1720-1722.

Nguyen et al., "Cross-linking the B7 family molecule B7-DC directly activates immune functions of dendritic cells," *J. Exp. Med.*, 2002, 196(10):1393-1398.

Nociari et al. "A novel one-step, highly sensitive fluorometric assay to evaluate cell-mediated cytotoxicity," *J. Immunol. Meth.*, 1998, 213:157-167.

Nonacs et al., "Mechanisms of Mouse Spleen Dendritic Cell Function in the Generation of Influenza-specific, Cytolytic T Lymphocytes," *J. Exp. Med.*, 1992, 176:519-529.

Osborne, "MS Groundwork Laid, Acorda Taking Program 'On the Road'," *BioWorld Today*, 2004, 15(88):1-2.

Pardo et al., "Granzymes are essential for natural killer cell-mediated and perf-facilitated tumor control," *Eur. J. Immunol.*, 2002, 32:2881-2886.

Pease et al., "Spontaneous H-2 mutants provide evidence that a copy mechanism analogous to gene conversion generates polymorphism in the major histocompatibility complex," *Proc. Natl. Acad. Sci. USA*, 1983, 80:242-246.

Plotnicky-Gilquin, "Differential Effects of Parainfluenza Virus Type 3 on Human Monocytes and Dendritic Cells," *Virology*, 2001, 285:82-90.

Poltorak et al., "Defective LPS Signaling in C3H/HeJ and C57BL/10ScCr Mice: Mutations in Tlr4 Gene," *Science*, 1998, 282:2085-2088.

Pulendran et al., "Developmental Pathways of Dendritic Cells in Vivo. Distinct Function, Phenotype, and Localization of Dendritic Cell Subsets in FLT3 Ligand-Treated Mice,", *J. Immunol.*, 1997, 159:2222-2231.

Pulendran et al., "Sensing Pathogens and Tuning Immune Responses," *Science*, 2001, 293:253-256.

Radhakrishnan et al., "Blockade of allergic airway inflammation following systemic treatment with a B7-dendritic cell (PD-L2) cross-linking human antibody," *J. Immunol.*, 2004, 173(2):1360-1365.

Radhakrishnan et al., "Immunotherapeutic potential of B7-DC (PD-L2) cross-linking antibody in conferring antitumor immunity," *Cancer Res.*, 2004, 64(14):4965-4972.

Radhakrishnan et al., "Naturally occurring human IgM antibody that binds B7-DC and potentiates T cell stimulation by dendritic cells," *J. Immunol.*, 2003, 170:1830-1838.

Ray and Cohn, "Th2 cells and GATA-3 in asthma: new insights into the regulation of airway inflammation," *J. Clin. Invest.*, 1999, 104(8):985-993.

Rötzschke et al., "Exact prediction of 2894 a natural T cell epitope," *Eur. J. Immunol.*, 1991, 21:2891-2894.

Sertl et al., "Dendritic Cells with Antigen-Presenting Capability Reside in Airway Epithelium, Lung Parenchyma, and Visceral Pleura," *J. Exp. Med.*, 1986, 163:436-451.

Smyth et al., "Cutting Edge: Granzymes A and B Are Not Essential for Perforin-Mediated Tumor Rejection," *J. Immunol.*, 2003, 171:515-518.

Steinman and Witmer, "Lymphoid dendritic cells are potent stimulators of the primary mixed leukocyte reaction in mice," *Proc. Natl. Acad. Sci. USA*, 1978, 75(10):5132-5136.

Steinman, "The Dendritic Cell System and Its Role in Immunogenicity," 1991, *Annu. Rev. Immunol.*, 1991, 9:271-296.

Strunk et al., "A Skin Homing Molecule Defines the Langerhans Cell Progenitor in Human Peripheral Blood," *J. Exp. Med..*, 1997, 185(6):1131-1136.

Stryer, *Biochemistry*, 1981, (2nd edition) W. H. Freeman and Co. San Francisco, pp. 14-15.

Stumbles et al., "Resting Respiratory Tract Dendritic Cells Preferentially Stimulate T Helper Cell Type 2 (Th2) Responses and Require Obligatory Cytokine Signals for Induction of Th1 Immunity," *J. Exp. Med.*, 1998, 188(11):2019-2031.

Tallquist et al., "A Single T Cell Receptor Recognizes Structurally Distinct MHC/Peptide Complexes with High Specificity," J. Exp. Med., 1996, 184:1017-1026.

Thierfelder et al., "Requirement for Stat4 in interleukin-12-mediated responses of natural killer and T cells," *Nature*, 1996, 382:171-174.

Tseng et al., "B7-DC, a New Dendritic Cell Molecule with Potent Costimulatory Properties for T Cells," *J. Exp. Med.*, 2001, 193(7):839-845.

van den Broek et al., "Decreased Tumor Surveillance in Perforin-deficient Mice," *J. Exp. Med.*, 1996, 184:1781-1790.

Vremec and Shortman, "Dendritic Cell Subtypes in Mouse Lymphoid Organs. Cross-Correlation of Surface Markers, Changes with Incubation, and Differences Among Thymus, Spleen, and Lymph Nodes," *J. Immunol.*, 1997, 159:565-573.

Vremec et al., "CD4 and CD8 Expression by Dendritic Cell Subtypes in Mouse Thymus and Spleen," *J. Immunol.*, 2000, 164:2978-2986.

Vremec et al., "The Surface Phenotype of Dendritic Cells Purified from Mouse Thymus and Spleen: Investigation of the CD8 Expression by a Subpopulation of Dendritic Cells," *J. Exp. Med.*, 1992, 176:47-58.

Warrington et al., "Human monoclonal antibodies reactive to oligodendrocytes promote remyelination in a model of multiple sclerosis," *Proc. Natl. Acad. Sci. USA*, 2000, 97(12):6820-6825.

Warrington et al., "Immunoglobulin-mediated CNS repair," *J. Allergy Clin. Immunol.*, 2001, 108:S121-S125.

Warrington et al., "Neuron-binding human monoclonal antibodies support central nervous system neurite extension," *J. Neuropathol. Exp. Neurol.*, 2004, 63(5):461-473.

Wills-Karp, "Immunologic Basis of Antigen-Induced Airway Hyperresponsiveness," *Annu. Rev. Immunol.*, 1999, 17:255-281.

Winzler et al., "Maturation Stages of Mouse Dendritic Cells in Growth Factor-dependent Long-Term Cultures," *J. Exp. Med.*, 1997, 185(2):317-328.

Woodhead et al., "Novel molecular mechanisms of dendritic cell-induced T cell activation," *Int. Immunol.*, 2000, 12(7):1051-1061.

Wu et al. "Derivation of Dendritic Cells from Myeloid and Lymphoid Precursors " *Intern. Rev. Immunol.*, 2001, 20:117-135.

Wu et al., "Thymic Dendritic Cell Precursors: Relationship to the T Lymphocyte Lineage and Phenotype of the Dendritic Cell Progeny," *J. Exp. Med.*, 1996, 184:903-911.

Wülfing and Davis, "A Receptor/Cytoskeletal Movement Triggered by Costimulation During T Cell Activation," *Science.* 1998, 282:2266-2269.

Yoshida et al., "Host origin of follicular dendritic cells induced in the spleen of SCID mice after transfer of allogeneic lymphocytes," *Immunology*, 1995, 84:117-126.

Young and Steinman, "Dendritic Cells Stimulate Primary Human Cytolytic Lymphocyte Responses in the Absence of CD4[+]Helper T Cells," *J. Exp. Med.*, 1990, 171:1315-1332.

Zhang et al., "Influence of the Route of Allergen Administration and Genetic Background on the Murine Allergic Pulmonary Response," *Am. J. Respir. Crit. Care Med.*, 1997, 155:661-669.

sHIgM12

PD-1

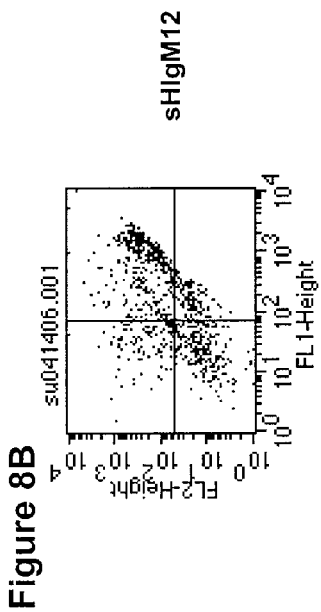
Figure 8A sHIgM39
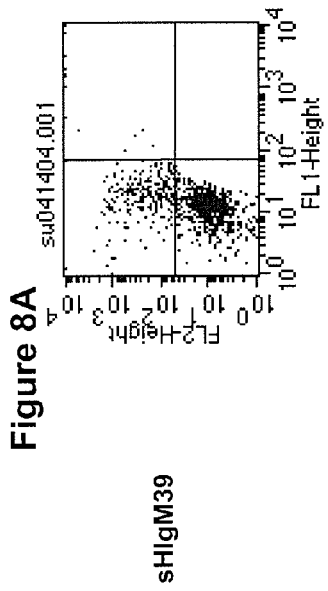
Figure 8B sHIgM12
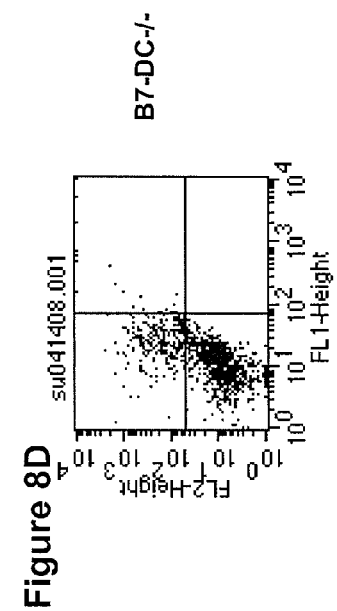
Figure 8C TY-25 blockade
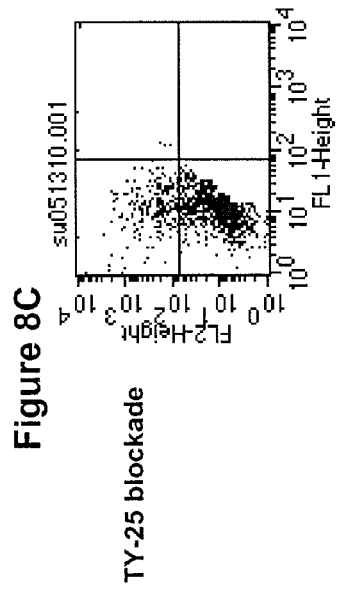
Figure 8D B7-DC-/-
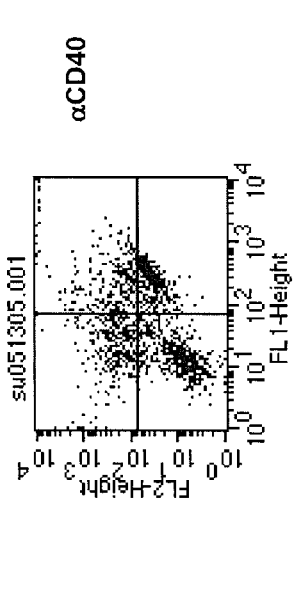
Figure 8E αCD40 on B7-DC-/-
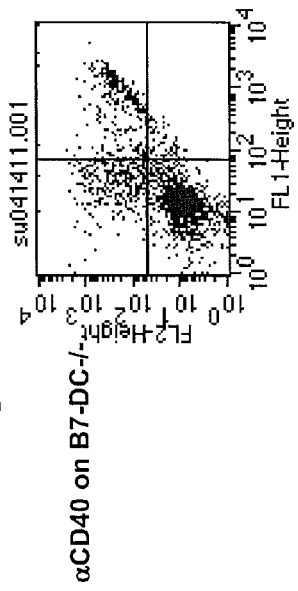
Figure 8F αCD40

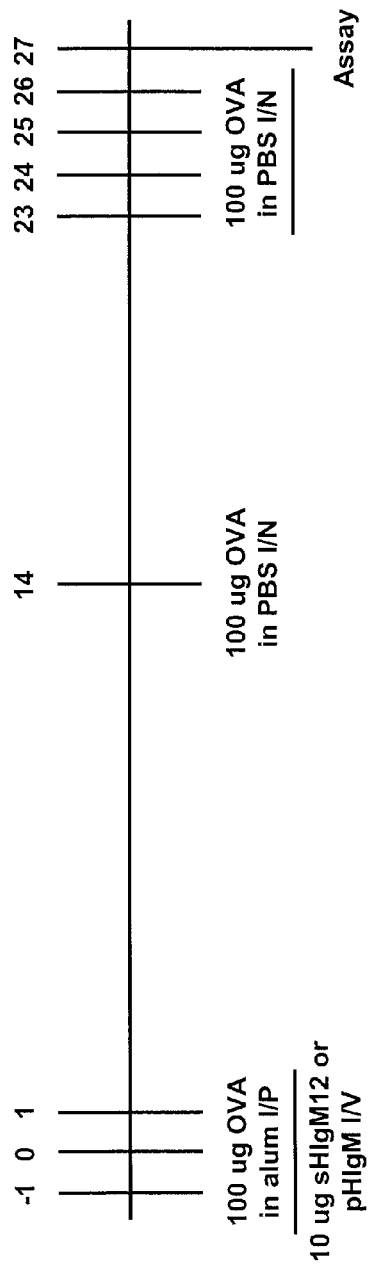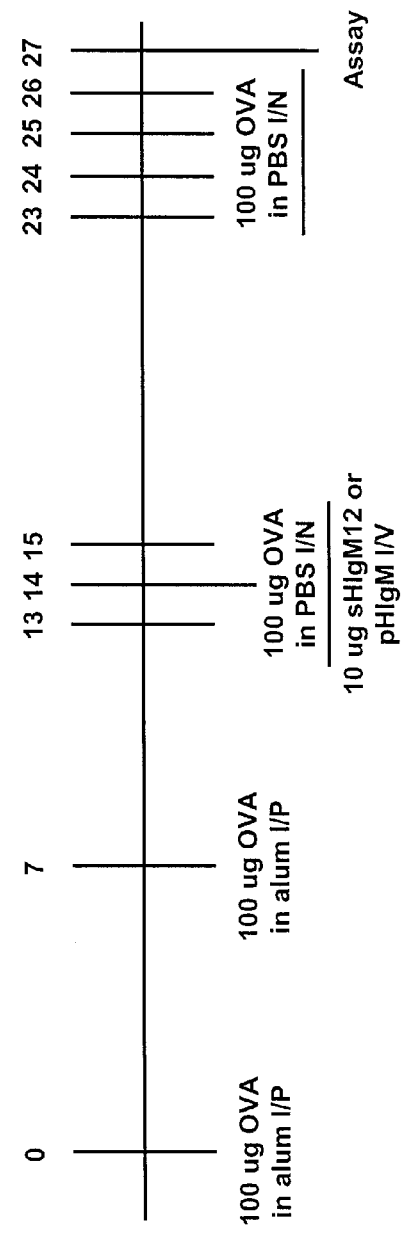

Figure 19A

Vk:
DIQMTQSPSSLSASVGDRVTITCRASQSISSYLNWYQQKPGKAPKVLIYAASLRSGVPSRFSGSGSGTDFTLTVSSLQPEDFATYYCQQSYHTPWTFGQGTKVEIK (SEQ ID NO:6)

Ck:
RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC (SEQ ID NO:7)

Figure 19B

Vh:
QVQLQESGPGLLKPSETLSLTCTVSGGSVSLYYWSWIRQSPGKEPEWIGYIYSSGSTDYN
PSLRSRVTISLDTSNNRFSLNLRSVTAADTAVYWCARSASIRGWFDPWGQGTLVTSS
(SEQ ID NO:8)

CH1:
GSASAPTLFPLVSCENSPSDTSSVAVGCLAQDFLPDSITFSWKYKNNSDISSTRGFPSVLR
GGKYAATSQVLLPSKDVMQGTDEHVVCKVQHPNGNKEKNVPLP (SEQ ID NO:9)

CH2:
VIAELPPKVSVFVPPRDGFFGNPRKSKLICQATGFSPRQIQVSWLREGKQVGSGVTTDQV
QAEAKESGPTTYKVTSTLTIKESDWLSQSMFTCRVDHRGLTFQQNASSMCVP (SEQ ID
NO:10)

CH3:
DQDTAIRVFAIPPSFASIFLTKSTKLTCLVTDLTTYDSVTISWTRQNGEAVKTHTNISESHPN
ATFSAVGEASICEDDWNSGERFTCTVTHTDLPSPLKQTISRPK (SEQ ID NO:11)

CH4:
GVALHRPDVYLLPPAREQLNLRESATITCLVTGFSPADVFVQWMQRGQPLSPEKYVTSAP
MPEPQAPGRYFAHSILTVSEEEWNTGETYTCVVAHEALPNRVTERTVDKSTGKPTLYNVS
LVMSDTAGTCY (SEQ ID NO:12)

Figure 20

Vk:
GACATCCAGATGACCCAGTCTCCATCCTCCCTGTCTGCGTCTGTAGGAGACAGAGTCACC
ATCACTTGCCGGGCAAGTCAGAGTATTAGTAGTTATCTAAATTGGTATCAGCAGAAACCAG
GGAAAGCCCCTAAGGTCCTGATCTATGCTGCATCCACTTTGCGAAGTGGGGTCCCGTCAA
GGTTCAGTGGCAGTGGATCTGGGACAGATTTCACTCTCACCGTCAGCAGTCTGCAACCTG
AAGATTTTGCAACTTACTACTGTCAACAGAGTTACCATACCCCGTGGACGTTCGGTCAGGG
GACCAAGGTGGAAATCAAACGAACTGTGGCTGCAC (SEQ ID NO:13)

Vh:
CAGGTGCAGCTGCAGGAGAGTCGGGTCCAGGACTGTCCAGGACCCTGTCCCT
CACATGCACTGTCTCTGGTGGCTCCGTCAGTCTTACTACTGGATCCGGCAGTC
CCCAGGGAAGGAACCGGAGTGGATTGGATATCTATTCCAGTGGAAGCACCGATTACAA
CCCTTCCCCTCAGGAGTCGAGTCGAGTCACCATATCACTGGACACGTCAAACAACCGGTTTTCCCTA
AACCTGAGGTCTGTGACCGCCGCAGATACAGCGGTCTATTGGTGTGCGAGAAGTGCGTCA
ATTAGGGGCTGGTTCGACCCCTGGGGCCAGGGAACCCTGGTCACCGTCTCCTCAGGGAG
TGCATCCGCC (SEQ ID NO:14)

SEQUENCE LISTING

```
<160> NUMBER OF SEQ ID NOS: 14

<210> SEQ ID NO 1
<211> LENGTH: 8
<212> TYPE: PRT
<213> ORGANISM: Gallus gallus

<400> SEQUENCE: 1

Ser Ile Ile Asn Phe Glu Lys Leu
 1               5

<210> SEQ ID NO 2
<211> LENGTH: 14
<212> TYPE: PRT
<213> ORGANISM: Gallus gallus

<400> SEQUENCE: 2

Ile Ser Gln Ala Val His Ala Ala His Ala Glu Ile Asn Glu
 1               5                  10

<210> SEQ ID NO 3
<211> LENGTH: 20
<212> TYPE: DNA
<213> ORGANISM: Artificial Sequence
<220> FEATURE:
<223> OTHER INFORMATION: Synthetically generated oligonucleotide

<400> SEQUENCE: 3
tccatgacgt tcctgacgtt                                                   20

<210> SEQ ID NO 4
<211> LENGTH: 21
<212> TYPE: PRT
<213> ORGANISM: Homo sapiens
<220> FEATURE:
<221> NAME/KEY: VARIANT
<222> LOCATION: 18
<223> OTHER INFORMATION: Xaa = Arg or Ser
```

-continued

```
<400> SEQUENCE: 4

Val Gln Leu Gln Glu Ser Gly Pro Gly Leu Leu Lys Pro Ser Glu Thr
  1               5                  10                  15

Leu Xaa Leu Thr Asn
            20

<210> SEQ ID NO 5
<211> LENGTH: 19
<212> TYPE: PRT
<213> ORGANISM: Homo sapiens

<400> SEQUENCE: 5

Asp Ile Gln Met Thr Gln Ser Pro Ser Ser Leu Ser Ala Ser Val Gly
  1               5                  10                  15

Asp Arg Val

<210> SEQ ID NO 6
<211> LENGTH: 106
<212> TYPE: PRT
<213> ORGANISM: Homo sapiens

<400> SEQUENCE: 6

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Ser Ile Ser Ser Tyr
             20                  25                  30

Leu Asn Trp Tyr Gln Gln Lys Pro Gly Lys Ala Pro Lys Val Leu Ile
         35                  40                  45

Tyr Ala Ala Ser Leu Arg Ser Gly Val Pro Ser Arg Phe Ser Gly Ser
     50                  55                  60

Gly Ser Gly Thr Asp Phe Thr Leu Thr Val Ser Ser Leu Gln Pro Glu
 65                  70                  75                  80

Asp Phe Ala Thr Tyr Tyr Cys Gln Gln Ser Tyr His Thr Pro Trp Thr
                 85                  90                  95

Phe Gly Gln Gly Thr Lys Val Glu Ile Lys
                100                 105

<210> SEQ ID NO 7
<211> LENGTH: 107
<212> TYPE: PRT
<213> ORGANISM: Homo sapiens

<400> SEQUENCE: 7

Arg Thr Val Ala Ala Pro Ser Val Phe Ile Phe Pro Pro Ser Asp Glu
  1               5                  10                  15

Gln Leu Lys Ser Gly Thr Ala Ser Val Val Cys Leu Leu Asn Asn Phe
             20                  25                  30

Tyr Pro Arg Glu Ala Lys Val Gln Trp Lys Val Asp Asn Ala Leu Gln
         35                  40                  45

Ser Gly Asn Ser Gln Glu Ser Val Thr Glu Gln Asp Ser Lys Asp Ser
     50                  55                  60

Thr Tyr Ser Leu Ser Ser Thr Leu Thr Leu Ser Lys Ala Asp Tyr Glu
 65                  70                  75                  80

Lys His Lys Val Tyr Ala Cys Glu Val Thr His Gln Gly Leu Ser Ser
                 85                  90                  95

Pro Val Thr Lys Ser Phe Asn Arg Gly Glu Cys
                100                 105
```

-continued

```
<210> SEQ ID NO 8
<211> LENGTH: 118
<212> TYPE: PRT
<213> ORGANISM: Homo sapiens

<400> SEQUENCE: 8

Gln Val Gln Leu Gln Glu Ser Gly Pro Gly Leu Leu Lys Pro Ser Glu
  1               5                  10                  15

Thr Leu Ser Leu Thr Cys Thr Val Ser Gly Ser Val Ser Leu Tyr
             20                  25                  30

Tyr Trp Ser Trp Ile Arg Gln Ser Pro Gly Lys Glu Pro Glu Trp Ile
         35                  40                  45

Gly Tyr Ile Tyr Ser Ser Gly Ser Thr Asp Tyr Asn Pro Ser Leu Arg
     50                  55                  60

Ser Arg Val Thr Ile Ser Leu Asp Thr Ser Asn Asn Arg Phe Ser Leu
 65                  70                  75                  80

Asn Leu Arg Ser Val Thr Ala Ala Asp Thr Ala Val Tyr Trp Cys Ala
                 85                  90                  95

Arg Ser Ala Ser Ile Arg Gly Trp Phe Asp Pro Trp Gly Gln Gly Thr
            100                 105                 110

Leu Val Thr Val Ser Ser
        115

<210> SEQ ID NO 9
<211> LENGTH: 104
<212> TYPE: PRT
<213> ORGANISM: Homo sapiens

<400> SEQUENCE: 9

Gly Ser Ala Ser Ala Pro Thr Leu Phe Pro Leu Val Ser Cys Glu Asn
  1               5                  10                  15

Ser Pro Ser Asp Thr Ser Ser Val Ala Val Gly Cys Leu Ala Gln Asp
             20                  25                  30

Phe Leu Pro Asp Ser Ile Thr Phe Ser Trp Lys Tyr Lys Asn Asn Ser
         35                  40                  45

Asp Ile Ser Ser Thr Arg Gly Phe Pro Ser Val Leu Arg Gly Gly Lys
     50                  55                  60

Tyr Ala Ala Thr Ser Gln Val Leu Leu Pro Ser Lys Asp Val Met Gln
 65                  70                  75                  80

Gly Thr Asp Glu His Val Val Cys Lys Val Gln His Pro Asn Gly Asn
                 85                  90                  95

Lys Glu Lys Asn Val Pro Leu Pro
            100

<210> SEQ ID NO 10
<211> LENGTH: 112
<212> TYPE: PRT
<213> ORGANISM: Homo sapiens

<400> SEQUENCE: 10

Val Ile Ala Glu Leu Pro Pro Lys Val Ser Val Phe Val Pro Pro Arg
  1               5                  10                  15

Asp Gly Phe Phe Gly Asn Pro Arg Lys Ser Lys Leu Ile Cys Gln Ala
             20                  25                  30

Thr Gly Phe Ser Pro Arg Gln Ile Gln Val Ser Trp Leu Arg Glu Gly
         35                  40                  45

Lys Gln Val Gly Ser Gly Val Thr Thr Asp Gln Val Gln Ala Glu Ala
     50                  55                  60
```

```
Lys Glu Ser Gly Pro Thr Thr Tyr Lys Val Thr Ser Thr Leu Thr Ile
 65                  70                  75                  80

Lys Glu Ser Asp Trp Leu Ser Gln Ser Met Phe Thr Cys Arg Val Asp
                 85                  90                  95

His Arg Gly Leu Thr Phe Gln Gln Asn Ala Ser Ser Met Cys Val Pro
            100                 105                 110
```

<210> SEQ ID NO 11
<211> LENGTH: 106
<212> TYPE: PRT
<213> ORGANISM: Homo sapiens

<400> SEQUENCE: 11

```
Asp Gln Asp Thr Ala Ile Arg Val Phe Ala Ile Pro Pro Ser Phe Ala
  1               5                  10                  15

Ser Ile Phe Leu Thr Lys Ser Thr Lys Leu Thr Cys Leu Val Thr Asp
                 20                  25                  30

Leu Thr Thr Tyr Asp Ser Val Thr Ile Ser Trp Thr Arg Gln Asn Gly
             35                  40                  45

Glu Ala Val Lys Thr His Thr Asn Ile Ser Glu Ser His Pro Asn Ala
 50                  55                  60

Thr Phe Ser Ala Val Gly Glu Ala Ser Ile Cys Glu Asp Asp Trp Asn
 65                  70                  75                  80

Ser Gly Glu Arg Phe Thr Cys Thr Val Thr His Thr Asp Leu Pro Ser
                 85                  90                  95

Pro Leu Lys Gln Thr Ile Ser Arg Pro Lys
            100                 105
```

<210> SEQ ID NO 12
<211> LENGTH: 131
<212> TYPE: PRT
<213> ORGANISM: Homo sapiens

<400> SEQUENCE: 12

```
Gly Val Ala Leu His Arg Pro Asp Val Tyr Leu Leu Pro Pro Ala Arg
  1               5                  10                  15

Glu Gln Leu Asn Leu Arg Glu Ser Ala Thr Ile Thr Cys Leu Val Thr
                 20                  25                  30

Gly Phe Ser Pro Ala Asp Val Phe Val Gln Trp Met Gln Arg Gly Gln
             35                  40                  45

Pro Leu Ser Pro Glu Lys Tyr Val Thr Ser Ala Pro Met Pro Glu Pro
 50                  55                  60

Gln Ala Pro Gly Arg Tyr Phe Ala His Ser Ile Leu Thr Val Ser Glu
 65                  70                  75                  80

Glu Glu Trp Asn Thr Gly Glu Thr Tyr Thr Cys Val Val Ala His Glu
                 85                  90                  95

Ala Leu Pro Asn Arg Val Thr Glu Arg Thr Val Asp Lys Ser Thr Gly
            100                 105                 110

Lys Pro Thr Leu Tyr Asn Val Ser Leu Val Met Ser Asp Thr Ala Gly
            115                 120                 125

Thr Cys Tyr
    130
```

<210> SEQ ID NO 13
<211> LENGTH: 337
<212> TYPE: DNA
<213> ORGANISM: Homo sapiens

```
<400> SEQUENCE: 13
gacatccaga tgacccagtc tccatcctcc ttgtctgcgt ctgtaggaga cagagtcacc      60
atcacttgcc gggcaagtca gagtattagt agttatctaa attggtatca gcagaaacca     120
gggaaagccc ctaaggtcct gatctatgct gcatccactt tgcgaagtgg ggtcccgtca     180
aggttcagtg gcagtggatc tgggacagat ttcactctca ccgtcagcag tctgcaacct     240
gaagattttg caacttacta ctgtcaacag agttaccata ccccgtggac gttcggtcag     300
gggaccaagg tggaaatcaa acgaactgtg gctgcac                              337

<210> SEQ ID NO 14
<211> LENGTH: 369
<212> TYPE: DNA
<213> ORGANISM: Homo sapiens

<400> SEQUENCE: 14
caggtgcagc tgcaggagtc gggtccagga ctgctgaagc cttcggagac cctgtccctc      60
acatgcactg tctctggtgg ctccgtcagt ctttactact ggagctggat ccggcagtcc     120
ccagggaagg aaccggagtg gattggatat atctattcca gtggaagcac cgattacaac     180
ccttccctca ggagtcgagt caccatatca ctggacacgt caaacaaccg gtttccccta     240
aacctgaggt ctgtgaccgc cgcagataca gcggtctatt ggtgtgcgag aagtgcgtca     300
attaggggct ggttcgaccc ctggggccag ggaaccctgg tcaccgtctc ctcagggagt     360
gcatccgcc                                                             369
```

RECOMBINANTLY PRODUCED ANTIBODY

CROSS-REFERENCE TO RELATED APPLICATIONS

This application is a continuation of U.S. application Ser. No. 10/983,104, filed on Nov. 5, 2004.

TECHNICAL FIELD

This invention relates to an antibody that can bind to and cross-link B7-DC polypeptides on the surface of a cell. The invention also relates to methods for using the B7-DC cross-linking antibody to modulate an existing state of immune responsiveness, and to treat or inhibit development of allergic asthma.

BACKGROUND

Decavalent IgM antibodies display measurable binding avidity to antigens, even though binding affinity may be low. The multivalent structure of pentameric IgM provides the potential for cross-linking cell surface targets, endowing the soluble antibodies with biological potential not normally associated with immune function.

Dendritic cells (DC) are efficient antigen-presenting cells (APC). These cells express class I and class II major histocompatibility complex (MHC) peptide-presenting molecules on their cell surfaces, along with a series of costimulatory molecules (Banchereau and Steinman (1998) *Nature* 392: 245-252). Naïve T cells express receptors for these DC ligands. Following recognition of peptide-antigen presented in the context of class I or class II molecules, the structure of the T cell membrane is reorganized, bringing together the elements of the T cell receptor with other cell-surface molecules, including the co-receptors CD4 or CD8 and the costimulatory receptors CD28 and CTLA-4 (Monks et al. (1998) *Nature* 395:82-86; and Wulfing and Davis (1998) *Science* 282:2266-2269). Interactions within the newly formed macromolecular complexes determine the outcome of inductive events transduced into T cells by DC.

DC reside in a variety of tissues and display distinct tissue-associated phenotypes (Strunk et al. (1997) *J. Exp. Med.* 185:1131-1136; Caux et al. (1996) *J. Exp. Med.* 184:695-706; Wu et al. (1996) *J. Exp. Med.* 184:903-911; and Vremec et al. (1992) *J. Exp. Med.* 176:47-58). The relationships among the cell lineages of these different subsets of cells are not firmly established. A large body of work has emerged focusing on DC generated in vitro from bone marrow or blood precursors (Mayordomo et al. (1995) *Nat. Med.* 1:1297-1302; Nonacs et al. (1992) *J. Exp. Med.* 176:519-529; Steinman and Witmer (1978) *Proc. Natl. Acad. Sci. USA* 75:5132-5136; and Young and Steinman (1990) *J. Exp. Med.* 171:1315-1332). The cells generated in vitro express high levels of class I antigens and the series of costimulatory ligands associated with endogenous DC (Fagnoni et al. (1995) *Immunology* 85:467-474; and Banchereau et al. (2000) *Annu. Rev. Immunol.* 18:767-811). Importantly, they are able to efficiently activate naïve T cells, a function that is the signature of the DC.

Asthma is primarily a chronic inflammatory disease of the airways. This primary inflammation causes two secondary symptoms: (a) overly reactive bronchi that are more sensitive to various asthma triggers such as allergens, cold and dry air, smoke and viruses, and (b) airflow obstruction (i.e., difficulty moving air in and out of the lungs). These symptoms are typically manifested by coughing, wheezing, shortness of breath or rapid breathing, and chest tightness.

Allergic asthma is the most common form of asthma. Many of the symptoms of allergic and non-allergic asthma are the same. Allergic asthma is triggered by inhaling allergens such as dust mites, pet dander, pollens, or mold. Through a complex reaction, these allergens then cause the passages in the airways of the lungs to become inflamed and swollen, resulting in asthma symptoms.

Allergic asthma is characterized by pulmonary inflammatory infiltration and hyperreactivity to variety of lung irritants and stimuli such as methacholine. The hallmark of allergic asthma is abnormal expansion of Th2 cells in the lungs (Wills-Karp (1999) *Annu. Rev. Immunol.* 17:255-281; and Ray and Cohn (1999) *J. Clin. Invest.* 104:985-993). DC act as the major antigen presenting cells to naïve T cells in lymphoid organs (Steinman (1991) *Annu. Rev. Immunol.* 9:271-296). DC are present in the respiratory tract, and upon isolation from the trachea, bronchi, alveoli and visceral pleura, they are capable of antigen presentation to T cells (Holt and Schon-Hegrad (1987) *Immunol.* 62:349-356; and Sertl et al. (1986) *J. Exp. Med.* 163:436-451). In addition, it has been demonstrated using an ovalbumin (OVA) model of allergic asthma that pulmonary DC prime T cells, inducing a Th2 phenotype. Treatment of mice with GM-CSF modulated this effect toward a Th1 polarity, with an accompanying increase in message for IL-12 (Stumbles et al. (1998) *J. Exp. Med.* 188: 2019-2031).

SUMMARY

The invention is based on the discovery that a human B7-DC cross-linking molecule such as an antibody, for example, can modulate the immune response in an in vivo model of allergic airway inflammation. Treatment of mice with an antibody designated sHIgM12 just prior to and at the same time as OVA sensitization significantly attenuated the immune response. In addition, sHIgM12 treatment protected mice from allergic symptoms even when administered after hypersensitization. Moreover, the polarity of T cells isolated from the spleens of therapeutically treated mice was changed from strong Th2 to weak Th1. Thus, treatment with the B7-DC cross-linking antibody sHIgM12 protected mice in both prophylactic and therapeutic settings in the murine model of allergic airway inflammation. As such, the invention provides polypeptides having amino acid sequences that are similar or identical to the amino acid sequence of the sHIgM12 antibody. The invention also provides nucleic acid molecules encoding polypeptides that have amino acid sequences similar or identical to the amino acid sequence of sHIgM12. In addition, the invention provides methods for both treating and reducing development of allergic asthma. Methods of the invention also can be useful to treat or reduce development of other conditions involving a pathological immune response (e.g., irritable bowel disease or multiple sclerosis).

In one aspect, the invention features a purified polypeptide containing an amino acid sequence that is between 80.0% and 99.9% identical to the amino acid sequence set forth in SEQ ID NO:6 or SEQ ID NO:8. The amino acid sequence can be at least 95.0% (e.g., 99.1% or 99.2%) identical to the amino acid sequence set forth in SEQ ID NO:6 or SEQ ID NO:8. The purified polypeptide can further contain an amino acid sequence that is at least 80.0% identical to the amino acid sequence set forth in SEQ ID NO:7, SEQ ID NO:9, SEQ ID NO:10, SEQ ID NO:11, or SEQ ID NO:12.

In another aspect, the invention features an isolated nucleic acid encoding a polypeptide that comprises an amino acid sequence that is between 80.0% and 99.9% identical to the amino acid sequence set forth in SEQ ID NO:6 or SEQ ID NO:8. The amino acid sequence can be at least 95.0% (e.g., 99.1% or 99.2%) identical to the amino acid sequence set forth in SEQ ID NO:6 or SEQ ID NO:8. The encoded polypeptide can further contain an amino acid sequence that is between 80.0% and 99.9% identical to the amino acid sequence set forth in SEQ ID NO:7, SEQ ID NO:9, SEQ ID NO:10, SEQ ID NO:11, or SEQ ID NO:12.

In another aspect, the invention features a composition containing a polypeptide and a pharmaceutically acceptable carrier, wherein the polypeptide contains an amino acid sequence that is between 80.0% and 99.9% identical to the amino acid sequence set forth in SEQ ID NO:6 or SEQ ID NO:8. The polypeptide can further contain an amino acid sequence that is between 80.0% and 99.9% identical to the amino acid sequence set forth in SEQ ID NO:7, SEQ ID NO:9, SEQ ID NO:10, SEQ ID NO:11, or SEQ ID NO:12.

In still another aspect, the invention features a composition containing a nucleic acid molecule and a pharmaceutically acceptable carrier, wherein the nucleic acid encodes a polypeptide containing an amino acid sequence that is between 80% and 99.9% identical to the amino acid sequence set forth in SEQ ID NO:6 or SEQ ID NO:8. The encoded polypeptide can further contain an amino acid sequence that is between 80.0% and 99.9% identical to the amino acid sequence set forth in SEQ ID NO:7, SEQ ID NO:9, SEQ ID NO:10, SEQ ID NO:11, or SEQ ID NO:12.

In another aspect, the invention features an isolated nucleic acid molecule containing a nucleotide sequence that is between 80.0% and 99.9% identical to the nucleotide sequence set forth in SEQ ID NO:13 or SEQ ID NO:14. The nucleotide sequence can be at least 98.0% identical (e.g., at least 99% identical) to the nucleotide sequence set forth in SEQ ID NO:13 or SEQ ID NO:14.

The invention also features a method for treating allergic asthma in a mammal in need thereof. The method can include administering to the mammal an effective amount of a composition containing a B7-DC cross-linking molecule. The B7-DC cross-linking molecule can be an antibody (e.g., an antibody that recognizes a B7-DC epitope having a glycosylation site, or sHIgM12). The composition can further contain a pharmaceutically acceptable carrier. The method can further include the step of monitoring the mammal for a symptom of asthma, such as airway hyperreactivity, coughing, wheezing, shortness of breath, rapid breathing, chest tightness, reduced airflow, reduced airway capacity, increased cellular infiltration of the lungs, or eosinophil migration to the lungs.

In another aspect, the invention features a method for inhibiting development of allergic asthma in a mammal. The method can include administering to the mammal an effective amount of a composition containing a B7-DC cross-linking molecule. The B7-DC cross-linking molecule can be an antibody (e.g., an antibody that recognizes a B7-DC epitope having a glycosylation site, or sHIgM12). The composition can further contain a pharmaceutically acceptable carrier. The method can further include the step of monitoring the mammal for a symptom of asthma, such as airway hyperreactivity, coughing, wheezing, shortness of breath, rapid breathing, chest tightness, reduced airflow, reduced airway capacity, increased cellular infiltration of the lungs, or eosinophil migration to the lungs.

In another aspect, the invention features a method for inhibiting a Th2 response in a mammal. The method can include administering to the mammal an effective amount of a composition containing a B7-DC cross-linking molecule. The B7-DC cross-linking molecule can be an antibody (e.g., an antibody that recognizes a B7-DC epitope comprising a glycosylation site, or sHIgM12). The composition can further contain a pharmaceutically acceptable carrier. The method can further include the step of monitoring the mammal for a Th2 response (e.g., by measuring the level of IL-4 or IL-5).

In still another aspect, the invention features a method for modulating a state of immune responsiveness in a mammal. The method can include administering to the mammal an effective amount of a composition containing a B7-DC cross-linking molecule. The B7-DC cross-linking molecule can be an antibody (e.g., an antibody that recognizes a B7-DC epitope having a glycosylation site, or sHIgM12). The composition can further contain a pharmaceutically acceptable carrier.

The invention also features a method for modifying dendritic cell function in a mammal. The method can include administering to the mammal an effective amount of a composition containing a B7-DC cross-linking molecule. The B7-DC cross-linking molecule can be an antibody (e.g., an antibody that recognizes a B7-DC epitope having a glycosylation site, or sHIgM12). The composition can further contain a pharmaceutically acceptable carrier.

In another aspect, the invention features a recombinantly produced polypeptide that binds specifically to B7-DC molecules on a cell, wherein the binding results in cross-linking of a plurality of the B7-DC molecules. The recombinantly produced polypeptide can be an antibody (e.g., an antibody that recognizes a B7-DC epitope having a glycosylation site, or sHIgM12). The recombinantly produced polypeptide can modulate dendritic cell function when administered to a mammal.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 2A shows the MHC class I-restricted T cell response to DC treated with sHIgM12 (filled circles) or control polyclonal human IgM control (HIgM; open circles). FIG. 2B shows the MHC class II-restricted T cell response to DC treated with sHIgM12 (filled circles) or control polyclonal HIgM (open circles).

FIGS. 8A-8F are a series of flow cytometry plots showing the staining of cells from draining lymph nodes from mice that were treated with sHIgM12, an isotype matched control antibody, or an antibody specific for CD40 and then injected with FITC labeled OVA. Cells were labeled for the DC marker CD11c (shown on the Y-axis). The X-axis represents the amount of FITC acquired by the lymph node cells. Lymph node cells were analyzed from C57BL/6 mice treated with sHIgM39 (FIG. 8A); C57BL/6 mice treated with sHIgM12 (FIG. 8B); C57BL/6 mice treated as in panel B, except also receiving the B7-DC specific antibody TY-25 (FIG. 8C); B7-DC knockout mice treated with sHIgM12 (FIG. 8D); B7-DC knockout mice treated with the anti-CD 40 antibody HM40-3 (FIG. 8E); and C57BL/6 mice treated with the anti-CD40 antibody (FIG. 8F).

FIG. 15A is a timeline depicting the prophylactic regimen used in the experiments described herein. FIG. 15B is a timeline depicting the therapeutic regimen used in the experiments described herein.

FIG. 18B shows IFN-γ levels, FIG. 18C shows TNF-α levels, FIG. 18D shows IL-4 levels, FIG. 18E shows IL-5 levels, and FIG. 18F shows IL-10 levels.

FIG. 19A shows the amino acid sequences of the variable (Vk) and constant (Ck) domains (SEQ ID NOS:6 and 7, respectively) of the sHIgM12 light chain. FIG. 19B shows the amino acid sequences of the variable (Vh) and constant (CH1, CH2, CH3, CH4) domains (SEQ ID NOS:8, 9, 10, 11, and 12, respectively) of the sHIgM12 heavy chain.

FIG. 20 shows nucleic acid sequences that encode the Vk and Vh domains (SEQ ID NOS:13 and 14, respectively) of sHIgM12.

DETAILED DESCRIPTION

Figure 1:
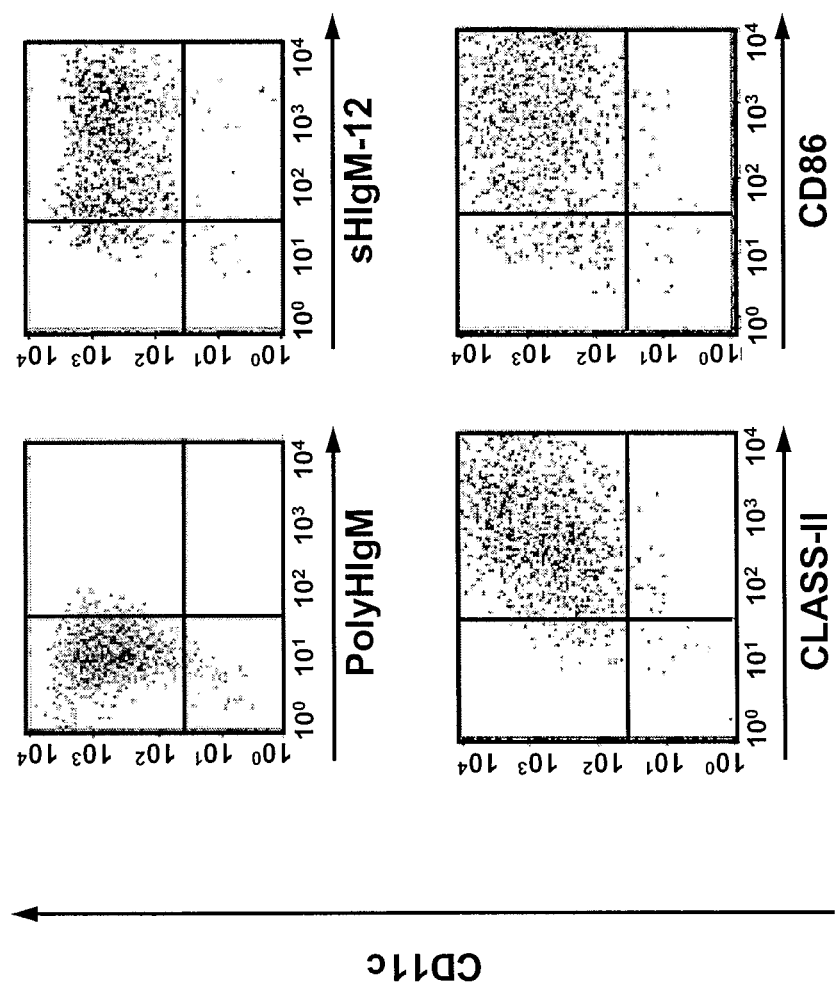
FIG. 1 is a series of fluorescence activated cell sorting (FACS) plots showing the staining of bone marrow-derived murine DC with sHIgM12 or polyclonal human IgM as indicated (upper panels), followed by fluorescein isothiocyanate- (FITC-) conjugated I-human IgM. Cells also were costained with phycoerythrin-(PE-) conjugated I-CD11c. The lower panels show staining with antibodies against typical DC surface markers, including MHC class II and CD86.

As described herein, a human IgM monoclonal antibody has been shown to bind to both human and murine DC in a B7-DC (PD-L2) dependent manner. This binding can result in (i) potentiation of the antigen presenting ability of the DC as seen by the ability to activate OT-I TCR transgenic T cells; (ii) increase in survival of the treated DC upon cytokine withdrawal; (iii) secretion of IL-12; and (iv) homing and/or survival of DC resulting in increased numbers reaching the draining lymph nodes. A monomeric form of the antibody (sHIgM12) was not able to potentiate the immune response, and actually inhibited the activity of an intact pentameric antibody. Thus, the targeted determinants on the surface of the DC may be activated by cross-linking.

The invention is based on the discovery that sHIgM12 also can modulate the immune response in an in vivo model of allergic airway inflammation. As described herein, treatment of mice with sHIgM12 just prior to and at the same time as OVA sensitization significantly attenuated the immune response. In addition, sHIgM12 treatment protected mice from allergic symptoms even when administered 14 days after hypersensitization. Thus, the invention provides polypeptides containing an amino acid sequence that is similar or identical to an amino acid sequence present within the sHIgM12 antibody. The invention also provides nucleic acid molecules encoding polypeptides that contain an amino acid sequence similar or identical to the amino acid sequence of the sHIgM12 antibody. In addition, the invention provides prophylactic and therapeutic methods for using a B7-DC cross-linking molecule such as sHIgM12 to alleviate allergic asthma. Further, the invention provides methods for inhibiting a Th2 response in a mammal.

1. B7-DC Cross-Linking Molecules

The invention provides molecules that bind specifically to B7-DC polypeptides. Such molecules can bind simultaneously to a plurality of B7-DC polypeptides (i.e., one such molecule can bind to more than one B7-DC polypeptide at the same time). Molecules provided herein thus can effectively cross-link a plurality of B7-DC polypeptides. These molecules typically are polypeptides, and antibodies can be particularly useful (see below), but other multivalent molecules that can bind and cross-link B7-DC on the surface of cells also can function in this capacity. Examples of such molecules include, without limitation, multivalent RNA or DNA aptamers. Aptamers typically are single-stranded DNA and RNA molecules that, like antibodies, can bind target molecules with affinity and specificity. Although nucleic acids are commonly thought of as linear molecules, they actually can take on complex, sequence-dependent, three-dimensional shapes. When the resulting shapes interact with a target protein, the result can be a tightly bound complex analogous to an antibody-antigen interaction. Aptamers can be modified to resist nuclease digestion, for example, or to enhance their therapeutic usefulness (e.g., to remain in the bloodstream longer, or to be stable in serum).

Molecules provided herein can bind specifically to cells through B7-DC polypeptides that are present on the cell surface. As used herein, "binds specifically to B7-DC" means that a molecule binds preferentially to B7-DC and does not display significant binding to other cell surface polypeptides (e.g., substantially less, or no, detectable binding to other cell surface polypeptides). As disclosed below, a polypeptide is an amino acid chain, regardless of post-translational modification. Thus, a molecule that binds specifically to a B7-DC polypeptide can "recognize" the B7-DC amino acid sequence or a portion thereof, a post-translational modification of B7-DC (e.g., one or more glycosylated or phosphorylated positions within the B7-DC amino acid sequence), or a combination thereof. Molecules (e.g., antibodies or polypeptides) can be tested for recognition of B7-DC using standard immunoassay methods, including FACS, enzyme-linked immunosorbent assay (ELISA), and radioimmuno assay (RIA). See, e.g., *Short Protocols in Molecular Biology*, eds. Ausubel et al., Green Publishing Associates and John Wiley & Sons (1992).

B7-DC is a cell surface polypeptide that can be found on, for example, DC, activated macrophages, and some tumor cells (e.g., glioma tumor cells). Molecules provided herein can bind to B7-DC on the surface of DC in a mammal (e.g., a human) and potentiate an immune response. As used herein, the term "potentiate an immune response" encompasses enhancement of DC function and increased activation of naïve T cells. Enhanced DC function includes components such as prolonged longevity of DC, which can be detected based on increased expression of NF-κB and increased translocation of NF-κB to the nucleus. Other components of enhanced DC function include an increased ability of DC to activate naïve T cells, increased localization of DC to the lymph nodes, increased phosphorylation of Akt (also known as protein kinase B) within DC, and increased secretion of cytokines such as interleukin-6 (IL-6), IL-12, RANTES, and tumor necrosis factor-alpha (TNF-α) by DC. Molecules provided by the invention also can enhance the metabolism of DC upon the withdrawal of cytokines from DC in culture. The molecules described herein can be administered to a mammal (e.g., a human) in order to enhance DC function and potentiate an immune response that can include any or all of the above-listed components. Such molecules also can be used to contact and activate DC in vitro.

Potentiation of an immune response can be measured by assessing any of the components listed above. Secretion of cytokines such as IL-12 can be measured, for example, by an enzyme linked immunosorbent (ELISA) assay as described in the Examples (below). Activation of naïve T cells can be assayed by, for example, measuring the incorporation of $^3$H-thymidine into newly synthesized DNA in proliferating cells, measuring induction of cytolytic T cell activity, or by detecting T cell activation markers such as CD44 and/or CD69. Expression or translocation of NF-κB can be measured by, for example, cell staining with an antibody against NF-κB. Increased phosphorylation of Akt can be assessed by, for example, western blotting with an antibody against phosphorylated Akt. Antibodies against NF-κB and phosphorylated Akt are available from, for example, Cell Signaling Technologies, Inc. (Beverly™, Mass.). Methods for measuring the other components encompassed by enhanced DC function and immunopotentiation also are described herein.

The molecules provided by the invention typically are purified. The term "purified" as used herein refers to a molecule that has been separated or isolated from other cellular components by which it is naturally accompanied (e.g., other cellular proteins, polynucleotides, or cellular components), or separated from most or all other components present in a reaction mixture when the molecule is synthesized in vitro. "Purified" as used herein also encompasses molecules that are partially purified, so that at least some of the components by which the molecule is accompanied are removed. Typically, a molecule is considered "purified" when it is at least 50% (e.g., 55%, 60%, 70%, 80%, 90%, 95%, or 99%), by dry weight, free from the proteins and other organic molecules or components with which it naturally associates or with which it is accompanied in a synthesis reaction.

Aptamers can be initially selected for specific binding activities from a starting pool of nucleic acids using, for example, methods known in the art. Variants can be obtained during subsequent rounds of amplification. An aptamer can be considered purified when it is at least 50% free from the other nucleic acids in the pool from which it is isolated.

2. Polypeptides and Antibodies

Molecules provided by the invention can be polypeptides. As used herein, a polypeptide is an amino acid chain, regardless of length or post-translational modification (e.g., phosphorylation or glycosylation). The polypeptides provided herein can bind specifically to B7-DC, and upon administration to a mammal (e.g., a human), can enhance DC function and potentiate an immune response. Polypeptides of the invention also can enhance DC function when incubated in vitro with DC.

The polypeptides featured herein can contain an amino acid sequence that is similar or identical to the amino acid sequence of sHIgM12. For example, a polypeptide can contain an amino acid sequence that is at least 80.0% identical (e.g., 80.0%, 85.0%, 90.0%, 95.0%, 97.0%, 97.5%, 98.0%, 98.5%, 99.0%, 99.1%, 99.2%, 99.3%, 99.4%, 99.5%, 99.6%, 99.7%, 99.8%, or 99.9% identical) to the amino acid sequence set forth in SEQ ID NO 6 or SEQ ID NO:8. In some embodiments, a polypeptide can further contain an amino acid sequence that is at least 80.0% identical (e.g., 80.0%, 85.0%, 90.0%, 95.0%, 97.0%, 97.5%, 98.0%, 98.5%, 99.0%, 99.1%, 99.2%, 99.3%, 99.4%, 99.5%, 99.6%, 99.7%, 99.8%, or 99.9% identical) to the amino acid sequence set forth in SEQ ID NO:7, SEQ ID NO:9, SEQ ID NO:10, SEQ ID NO:11, or SEQ ID NO:12. Percent sequence identity is calculated by determining the number of matched positions in aligned nucleic acid sequences, dividing the number of matched positions by the total number of aligned nucleotides, and multiplying by 100. A matched position refers to a position in which identical nucleotides occur at the same position in aligned nucleic acid sequences. Percent sequence identity also can be determined for any amino acid sequence.

To determine percent sequence identity, a target nucleic acid or amino acid sequence is compared to the identified nucleic acid or amino acid sequence using the BLAST 2 Sequences (Bl2seq) program from the stand-alone version of BLASTZ containing BLASTN version 2.0.14 and BLASTP version 2.0.14. This stand-alone version of BLASTZ can be obtained from Fish & Richardson's web site (World Wide Web at "fr" dot "com" slash "blast") or the U.S. government's National Center for Biotechnology Information web site (World Wide Web at "ncbi" dot "nlm" dot "nih" dot "gov"). Instructions explaining how to use the Bl2seq program can be found in the readme file accompanying BLASTZ.

Bl2seq performs a comparison between two sequences using either the BLASTN or BLASTP algorithm. BLASTN is used to compare nucleic acid sequences, while BLASTP is used to compare amino acid sequences. To compare two nucleic acid sequences, the options are set as follows: -i is set to a file containing the first nucleic acid sequence to be compared (e.g., C:\seq1.txt); -j is set to a file containing the second nucleic acid sequence to be compared (e.g., C:\seq2.txt); -p is set to blastn; -o is set to any desired file name (e.g., C:\output.txt); -q is set to -1; -r is set to 2; and all other options are left at their default setting. For example, the following command can be used to generate an output file containing a comparison between two sequences: C:\Bl2seq c:\seq1.txt -j c:\seq2.txt -p blastn -o c:\output.txt -q -1 -r 2. To compare two amino acid sequences, the options of Bl2seq are set as follows: -i is set to a file containing the first amino acid sequence to be compared (e.g., C:\seq1.txt); -j is set to a file containing the second amino acid sequence to be compared (e.g., C:\seq2.txt); -p is set to blastp; -o is set to any desired file name (e.g., C:\output.txt); and all other options are left at their default setting. For example, the following command can be used to generate an output file containing a comparison between two amino acid sequences: C:\Bl2seq c:\seq1.txt -j c:\seq2.txt -p blastp -o c:\output.txt. If the two compared sequences share homology, then the designated output file will present those regions of homology as aligned sequences. If the two compared sequences do not share homology, then the designated output file will not present aligned sequences.

Once aligned, the number of matches is determined by counting the number of positions where an identical nucleotide or amino acid residue is presented in both sequences. The percent sequence identity is determined by dividing the number of matches either by the length of the sequence set forth in the identified sequence (e.g., SEQ ID NO:6), or by an articulated length (e.g., 100 consecutive nucleotides or amino acid residues from a sequence set forth in an identified sequence), followed by multiplying the resulting value by 100. For example, a nucleic acid sequence that has 98 matches when aligned with the sequence set forth in SEQ ID NO:6 is 92.5 percent identical to the sequence set forth in SEQ ID NO:6 (i.e., 98÷106*100=92.5). It is noted that the percent sequence identity value is rounded to the nearest tenth. For example, 75.11, 75.12, 75.13, and 75.14 is rounded down to 75.1, while 75.15, 75.16, 75.17, 75.18, and 75.19 is rounded up to 75.2. It is also noted that the length value will always be an integer.

The amino acid sequences of the polypeptides provided herein can have substitutions, deletions, or additions with respect to the amino acid sequences set forth in SEQ ID NOS:6 and 8. A polypeptide having an amino acid sequence that is modified (e.g., by substitution) with respect to SEQ ID NO:6 and/or SEQ ID NO:8 can have substantially the same or improved qualities as compared to a polypeptide containing the amino acid sequence identical to that set forth in SEQ ID NO:6 and SEQ ID NO:8. A substitution can be a conserved substitution. As used herein, a "conserved substitution" is a substitution of an amino acid with another amino acid having a similar side chain. A conserved substitution typically can be a substitution with an amino acid that makes the smallest change possible in the charge of the amino acid or size of the side chain of the amino acid (alternatively, in the size, charge or kind of chemical group within the side chain) such that the overall peptide essentially retains its spatial conformation but has altered biological activity. Examples of conserved changes include, without limitation, Asp to Glu, Asn or Gln; His to Lys, Arg or Phe; Asn to Gln, Asp or Glu, and Ser to Cys, Thr or Gly. Alanine is commonly used to substitute for other amino acids. The 20 essential amino acids can be grouped as follows: alanine, valine, leucine, isoleucine, proline, phenylalanine, tryptophan and methionine having nonpolar side chains; glycine, serine, threonine, cysteine, tyrosine, asparagine and glutamine having uncharged polar side chains; aspartate and glutamate having acidic side chains; and lysine, arginine, and histidine having basic side chains (see, e.g., Stryer, *Biochemistry* ($2^{nd}$ edition) W.H. Freeman and Co. San Francisco (1981), pp. 14-15; and Lehninger, *Biochemistry* ($2^{nd}$ edition, 1975), pp. 73-75). Conservative substitutions can include substitutions made within these groups.

PD-1 is a polypeptide that is a natural receptor for B7-DC. PD-1 can be immobilized on a solid substrate (e.g., a plastic dish or a glass microscope slide). Upon incubation with DC, immobilized PD-1 can cross-link a plurality of B7-DC polypeptides on the cell surface and enhance the function of the DC. Incubation of cultured DC with immobilized PD-1 can, for example, maintain the metabolic rate of the cells upon removal of cytokines from the culture medium, as compared to the metabolic rate of DC that are not incubated with PD-1 (see Example 7).

Molecules provided herein can be antibodies that have specific binding activity for B7-DC. The terms "antibody" and "antibodies" encompass intact molecules as well as fragments thereof that are capable of binding to B7-DC. Antibodies can be polyclonal antibodies, monoclonal antibodies, humanized or chimeric antibodies, single chain Fv antibody fragments, Fab fragments, and $F(ab)_2$ fragments. Polyclonal antibodies are heterogeneous populations of antibody molecules that are specific for a particular antigen, while monoclonal antibodies are homogeneous populations of antibodies to a particular epitope contained within an antigen.

An antibody can be of any immunoglobulin (Ig) class, including IgM, IgA, IgD, IgE, and IgG, and any subclass thereof. Antibodies of the IgM class (e.g., sHIgM12) typically are pentavalent and are particularly useful because one antibody molecule can cross-link a plurality of B7-DC polypeptides. Immune complexes containing Ig molecules that are cross-linked (e.g., cross-linked IgG) and are thus multivalent also are capable of cross-linking a plurality of B7-DC molecules, and can be particularly useful.

As used herein, an "epitope" is a portion of an antigenic molecule to which an antibody binds. Antigens can present more than one epitope at the same time. For polypeptide antigens, an epitope typically is about four to six amino acids in length, and can include modified (e.g., phosphorylated or glycosylated) amino acids. Two different immunoglobulins can have the same epitope specificity if they bind to the same epitope or set of epitopes.

Polyclonal antibodies are contained in the sera of immunized animals. Monoclonal antibodies can be prepared using, for example, standard hybridoma technology. In particular, monoclonal antibodies can be obtained by any technique that provides for the production of antibody molecules by continuous cell lines in culture as described, for example, by Kohler et al. (1975) *Nature* 256:495-497, the human B-cell hybridoma technique of Kosbor et al. (1983) *Immunology Today* 4:72, and Cote et al. (1983) *Proc. Natl. Acad. Sci. USA* 80:2026-2030, and the EBV-hybridoma technique of Cole et al., *Monoclonal Antibodies and Cancer Therapy*, Alan R. Liss, Inc. pp. 77-96 (1983). A hybridoma producing monoclonal antibodies of the invention can be cultivated in vitro or in vivo.

Antibodies of the invention also can be isolated from, for example, the serum of an individual. The sHIgM12 antibody, for example, was isolated from human serum as described in Example 1 herein. Suitable methods for isolation include purification from mammalian serum using techniques that include, for example, chromatography.

Antibodies that bind to B7-DC also can be produced by, for example, immunizing host animals (e.g., rabbits, chickens, mice, guinea pigs, or rats) with B7-DC. A B7-DC polypeptide or a portion of a B7-DC polypeptide can be produced recombinantly, by chemical synthesis, or by purification of the native protein, and then used to immunize animals by injection of the polypeptide. Adjuvants can be used to increase the immunological response, depending on the host species. Suitable adjuvants include Freund's adjuvant (complete and incomplete), mineral gels such as aluminum hydroxide, surface active substances such as lysolecithin, pluronic polyols, polyanions, peptides, oil emulsions, keyhole limpet hemocyanin (KLH), and dinitrophenol. Standard techniques can be used to isolate antibodies generated in response to the B7-DC immunogen from the sera of the host animals. Such techniques are useful for generating antibodies that have similar characteristics to sHIgM12 (e.g., similar epitope specificity and other functional similarities).

Antibodies such as sHIgM12 also can be produced recombinantly. The amino acid sequence (e.g., the partial amino acid sequence) of an antibody provided herein can be determined by standard techniques, and a cDNA encoding the antibody or a portion of the antibody can be isolated from the serum of the subject (e.g., the human patient or the immunized host animal) from which the antibody was originally isolated. The cDNA can be cloned into an expression vector using standard techniques. The expression vector then can be transfected into an appropriate host cell (e.g., a Chinese hamster ovary cell, a COS cell, or a hybridoma cell), and the antibody can be expressed and purified. See, for example, Example 14 herein.

Antibody fragments that have specific binding affinity for B7-DC and retain cross-linking function also can be generated by techniques such as those disclosed above. Such antibody fragments include, but are not limited to, $F(ab')_2$ fragments that can be produced by pepsin digestion of an antibody molecule, and Fab fragments that can be generated by reducing the disulfide bridges of $F(ab')_2$ fragments. Alternatively, Fab expression libraries can be constructed. See, for example, Huse et al. (1989) *Science* 246:1275-1281. Single chain Fv antibody fragments are formed by linking the heavy and light chain fragments of the Fv region via an amino acid bridge (e.g., 15 to 18 amino acids), resulting in a single chain polypeptide. Single chain Fv antibody fragments can be produced through standard techniques, such as those disclosed in U.S. Pat. No. 4,946,778. Such fragments can be rendered multivalent by, for example, biotinylation and cross-linking, thus generating antibody fragments that can cross-link a plurality of B7-DC polypeptides.

3. Nucleic Acids, Vectors, and Host Cells

The invention provides nucleic acids encoding molecules (e.g., polypeptides and antibodies such as those described herein) that bind specifically to B7-DC. As used herein, the term "nucleic acid" refers to both RNA and DNA, including cDNA, genomic DNA, and synthetic (e.g., chemically synthesized) DNA. A nucleic acid molecule can be double-stranded or single-stranded (i.e., a sense or an antisense single strand). Nucleic acids of the invention include, for example, cDNAs encoding the light and heavy chains of the sHIgM12 antibody.

An "isolated nucleic acid" refers to a nucleic acid that is separated from other nucleic acid molecules that normally flank one or both sides of the nucleic acid in the genome in which it is normally found. The term "isolated" as used herein with respect to nucleic acids also includes any non-naturally-occurring nucleic acid sequence, since such non-naturally-occurring sequences are not found in nature and do not have immediately contiguous sequences in a naturally-occurring genome.

An isolated nucleic acid can be, for example, a DNA molecule, provided one of the nucleic acid sequences normally found immediately flanking that DNA molecule in its naturally-occurring genome is removed or absent. Thus, an isolated nucleic acid includes, without limitation, a DNA molecule that exists as a separate molecule (e.g., a chemically synthesized nucleic acid, or a cDNA or genomic DNA fragment produced by PCR or restriction endonuclease treatment) independent of other sequences as well as DNA that is incorporated into a vector, an autonomously replicating plasmid, a virus (e.g., a retrovirus, lentivirus, adenovirus, or herpes virus), or into the genomic DNA of a prokaryote or eukaryote. In addition, an isolated nucleic acid can include an engineered nucleic acid such as a DNA molecule that is part of a hybrid or fusion nucleic acid. A nucleic acid existing among hundreds to millions of other nucleic acids within, for example, cDNA libraries or genomic libraries, or gel slices containing a genomic DNA restriction digest, is not considered an isolated nucleic acid.

The isolated nucleic acids disclosed herein can encode polypeptides provided by the invention. For example, an isolated nucleic acid can encode a polypeptide containing an amino acid sequence that is similar or identical to an amino acid sequence found in the variable or constant regions of sHIgM12. In one embodiment, a nucleic acid can encode a polypeptide containing an amino acid sequence that is at least 80.0% (e.g., 80.0%, 85.0%, 90.0%, 95.0%, 97.0%, 97.5%, 98.0%, 98.5%, 99.0%, 99.1%, 99.2%, 99.3%, 99.4%, 99.5%, 99.6%, 99.7%, 99.8%, or 99.9%) identical to the amino acid sequence set forth in SEQ ID NO:6 or SEQ ID NO:8. The encoded polypeptide can further contain an amino acid sequence that is at least 80.0% (e.g., 80.0%, 85.0%, 90.0%, 95.0%, 97.0%, 97.5%, 98.0%, 98.5%, 99.0%, 99.1%, 99.2%, 99.3%, 99.4%, 99.5%, 99.6%, 99.7%, 99.8%, or 99.9%) identical to the amino acid sequence set forth in SEQ ID NO:7, SEQ ID NO:9, SEQ ID NO:10, SEQ ID NO:11, or SEQ ID NO:12. In another embodiment, an isolated nucleic acid can contain a nucleotide sequence that is at least 80.0% (e.g., 80.0%, 85.0%, 90.0%, 95.0%, 97.0%, 97.5%, 98.0%, 98.5%, 99.0%, 99.1%, 99.2%, 99.3%, 99.4%, 99.5%, 99.6%, 99.7%, 99.8%, or 99.9%) identical to the nucleotide sequence set forth in SEQ ID NO:13 or SEQ ID NO:14. The method for determining percent sequence identity is provided herein.

The isolated nucleic acid molecules provided herein can be produced by standard techniques, including, without limitation, common molecular cloning and chemical nucleic acid synthesis techniques. For example, polymerase chain reaction (PCR) techniques can be used to obtain an isolated nucleic acid molecule encoding an antibody such as sHIgM12. Isolated nucleic acids of the invention also can be chemically synthesized, either as a single nucleic acid molecule (e.g., using automated DNA synthesis in the 3' to 5' direction using phosphoramidite technology) or as a series of polynucleotides. For example, one or more pairs of long polynucleotides (e.g., >100 nucleotides) can be synthesized that contain the desired sequence, with each pair containing a short segment of complementarity (e.g., about 15 nucleotides) such that a duplex is formed when the polynucleotide pair is annealed. DNA polymerase is used to extend the polynucleotides, resulting in a single, double-stranded nucleic acid molecule per polynucleotide pair.

The invention also provides vectors containing nucleic acids such as those described above. As used herein, a "vector" is a replicon, such as a plasmid, phage, or cosmid, into which another DNA segment may be inserted so as to bring about the replication of the inserted segment. The vectors of the invention can be expression vectors. An "expression vector" is a vector that includes one or more expression control sequences, and an "expression control sequence" is a DNA sequence that controls and regulates the transcription and/or translation of another DNA sequence.

In the expression vectors of the invention, a nucleic acid (e.g., a nucleic acid encoding the light and/or heavy chains of sHIgM12) is operably linked to one or more expression control sequences. As used herein, "operably linked" means incorporated into a genetic construct so that expression control sequences effectively control expression of a coding sequence of interest. Examples of expression control sequences include promoters, enhancers, and transcription terminating regions. A promoter is an expression control sequence composed of a region of a DNA molecule, typically within 100 to 500 nucleotides upstream of the point at which transcription starts (generally near the initiation site for RNA polymerase II). To bring a coding sequence under the control of a promoter, it is necessary to position the translation initiation site of the translational reading frame of the polypeptide between one and about fifty nucleotides downstream of the promoter. Enhancers provide expression specificity in terms of time, location, and level. Unlike promoters, enhancers can function when located at various distances from the transcription site. An enhancer also can be located downstream from the transcription initiation site. A coding sequence is "operably linked" and "under the control" of expression control sequences in a cell when RNA polymerase is able to transcribe the coding sequence into mRNA, which then can be translated into the protein encoded by the coding sequence. Expression vectors provided herein thus are useful to produce sHIgM12, as well as other molecules of the invention.

Suitable expression vectors include, without limitation, plasmids and viral vectors derived from, for example, bacteriophage, baculoviruses, tobacco mosaic virus, herpes viruses, cytomegalovirus, retroviruses, vaccinia viruses, adenoviruses, and adeno-associated viruses. Numerous vectors and expression systems are commercially available from such corporations as Novagen (Madison, Wis.), Clontech (Palo Alto, Calif.), Stratagene (La Jolla, Calif.), and Invitrogen/Life Technologies (Carlsbad, Calif.).

An expression vector can include a tag sequence designed to facilitate subsequent manipulation of the expressed nucleic acid sequence (e.g., purification or localization). Tag sequences, such as green fluorescent protein (GFP), glutathione S-transferase (GST), polyhistidine, c-myc, hemagglutinin, or Flag™ tag (Kodak, New Haven, Conn.) sequences typically are expressed as a fusion with the encoded polypeptide. Such tags can be inserted anywhere within the polypeptide including at either the carboxyl or amino terminus.

The invention also provides host cells containing vectors of the invention. The term "host cell" is intended to include prokaryotic and eukaryotic cells into which a recombinant expression vector can be introduced. As used herein, "transformed" and "transfected" encompass the introduction of a nucleic acid molecule (e.g., a vector) into a cell by one of a number of techniques. Although not limited to a particular technique, a number of these techniques are well established within the art. Prokaryotic cells can be transformed with nucleic acids by, for example, electroporation or calcium chloride mediated transformation. Nucleic acids can be transfected into mammalian cells by techniques including, for example, calcium phosphate co-precipitation, DEAE-dextran-mediated transfection, lipofection, electroporation, or microinjection. Suitable methods for transforming and transfecting host cells are found in Sambrook et al., *Molecular Cloning: A Laboratory Manual* ($2^{nd}$ edition), Cold Spring Harbor Laboratory, New York (1989), and reagents for transformation and/or transfection are commercially available (e.g., Lipofectin® (Invitrogen/Life Technologies); Fugene (Roche, Indianapolis, Ind.); and SuperFect (Qiagen, Valencia, Calif.)).

4. Compositions

The molecules described herein (e.g., antibodies such as sHIgM12 and polypeptides such as PD-1) can be incorporated into compositions. Such compositions are provided herein, as is the use of B7-DC binding molecules in the manufacture of compositions. The compositions provided herein can be administered to a subject in order to enhance DC function and potentiate an immune response. Such compositions also can be useful to inhibit Th2 immune responses, and thus can treat or inhibit development of allergic asthma. As described herein, enhanced DC function includes such components as prolonged longevity, increased ability to activate naïve T cells, increased localization to the lymph nodes, increased phosphorylation of Akt, and increased secretion of interleukin-12 (IL-12).

Compositions provided herein also can contain a molecule (e.g., PD-1) that is immobilized on a solid substrate. Such compositions can be used to contact DC and enhance their function as described above.

Methods for formulating and subsequently administering therapeutic compositions are well known to those skilled in the art. Dosages typically are dependent on the responsiveness of the subject to the molecule, with the course of treatment lasting from several days to several months, or until a suitable immune response is achieved. Persons of ordinary skill in the art routinely determine optimum dosages, dosing methodologies and repetition rates. Optimum dosages can vary depending on the relative potency of an antibody, and generally can be estimated based on the $EC_{50}$ found to be effective in in vitro and/or in vivo animal models. Dosage typically is from 0.01 μg to 100 g per kg of body weight (e.g., from 1 μg to 100 mg, from 10 μg to 10 mg, or from 50 μg to 500 μg per kg of body weight). Compositions containing the molecules provided herein may be given once or more daily, weekly, monthly, or even less often.

In addition to the molecules provided herein, the compositions described herein further can contain antigens that will elicit a specific immune response. Suitable antigens include, for example, polypeptides or fragments of polypeptides expressed by tumors and pathogenic organisms. Killed viruses and bacteria, in addition to components of killed viruses and bacteria, also are useful antigens. Such antigens can stimulate immune responses against tumors or pathogens.

Compositions also can include DC that have been isolated from, for example, bone marrow, spleen, or thymus tissue. DC lines also can be useful in compositions of the invention.

The molecules featured herein (e.g., antibodies such as sHIgM12) can be admixed, encapsulated, conjugated or otherwise associated with other molecules, molecular structures, or mixtures of compounds such as, for example, liposomes, receptor targeted molecules, or oral, topical or other formulations for assisting in uptake, distribution and/or absorption.

In some embodiments, a composition can contain a molecule provided herein (e.g., sHIgM12, a polypeptide containing an amino acid sequence that is at least 80.0% identical to SEQ ID NO:6 or SEQ ID NO:8, a nucleic acid encoding a polypeptide that contains an amino acid sequence at least 80.0% identical to the sequence set forth in SEQ ID NO:6 or SEQ ID NO:8, or a nucleic acid molecule containing a nucleotide sequence that is at least 80.0% identical to the sequence set forth in SEQ ID NO:13 or SEQ ID NO:14) in combination with a pharmaceutically acceptable carrier. Pharmaceutically acceptable carriers are pharmaceutically acceptable solvents, suspending agents, or any other pharmacologically inert vehicles for delivering antibodies to a subject. Pharmaceutically acceptable carriers can be liquid or solid, and can be selected with the planned manner of administration in mind so as to provide for the desired bulk, consistency, and other pertinent transport and chemical properties, when combined with one or more therapeutic compounds and any other components of a given pharmaceutical composition. Typical pharmaceutically acceptable carriers include, without limitation: water; saline solution; binding agents (e.g., polyvinylpyrrolidone or hydroxypropyl methylcellulose); fillers (e.g., lactose and other sugars, gelatin, or calcium sulfate); lubricants (e.g., starch, polyethylene glycol, or sodium acetate); disintegrates (e.g., starch or sodium starch glycolate); and wetting agents (e.g., sodium lauryl sulfate).

Pharmaceutical compositions containing molecules provided herein can be administered by a number of methods, depending upon whether local or systemic treatment is desired. Administration can be, for example, parenteral (e.g., by subcutaneous, intrathecal, intraventricular, intramuscular, or intraperitoneal injection, or by intravenous (i.v.) drip); oral; topical (e.g., transdermal, sublingual, ophthalmic, or intranasal); or pulmonary (e.g., by inhalation or insufflation of powders or aerosols). Administration can be rapid (e.g., by injection) or can occur over a period of time (e.g., by slow infusion or administration of slow release formulations). For administration to the central nervous system, antibodies can be injected or infused into the cerebrospinal fluid, typically with one or more agents capable of promoting penetration across the blood-brain barrier.

Compositions and formulations for parenteral, intrathecal or intraventricular administration include sterile aqueous solutions (e.g., sterile physiological saline), which also can contain buffers, diluents and other suitable additives (e.g., penetration enhancers, carrier compounds and other pharmaceutically acceptable carriers).

Compositions and formulations for oral administration include, for example, powders or granules, suspensions or solutions in water or non-aqueous media, capsules, sachets, or tablets. Such compositions also can incorporate thickeners, flavoring agents, diluents, emulsifiers, dispersing aids, or binders.

Formulations for topical administration include, for example, sterile and non-sterile aqueous solutions, non-aqueous solutions in common solvents such as alcohols, or solutions in liquid or solid oil bases. Such solutions also can contain buffers, diluents and other suitable additives. Pharmaceutical compositions and formulations for topical administration can include transdermal patches, ointments, lotions, creams, gels, drops, suppositories, sprays, liquids, and powders. Conventional pharmaceutical carriers, aqueous, powder or oily bases, thickeners and the like may be useful.

Pharmaceutical compositions include, but are not limited to, solutions, emulsions, aqueous suspensions, and liposome-containing formulations. These compositions can be generated from a variety of components that include, for example, preformed liquids, self-emulsifying solids and self-emulsifying semisolids. Emulsion formulations are particularly useful for oral delivery of therapeutic compositions due to their ease of formulation and efficacy of solubilization, absorption, and bioavailability. Liposomes can be particularly useful due to their specificity and the duration of action they offer from the standpoint of drug delivery.

Molecules featured herein can encompass any pharmaceutically acceptable salts, esters, or salts of such esters, or any other compound which, upon administration to a subject, is capable of providing (directly or indirectly) the biologically active metabolite or residue thereof. Accordingly, for example, the invention provides pharmaceutically acceptable salts of molecules such as antibodies (e.g., sHIgM12), prodrugs and pharmaceutically acceptable salts of such prodrugs, and other bioequivalents. A prodrug is a therapeutic agent that is prepared in an inactive form and is converted to an active form (i.e., drug) within the body or cells thereof by the action of endogenous enzymes or other chemicals and/or conditions. The term "pharmaceutically acceptable salts" refers to physiologically and pharmaceutically acceptable salts of the antibodies useful in methods of the invention (i.e., salts that retain the desired biological activity of the parent antibodies without imparting undesired toxicological effects). Examples of pharmaceutically acceptable salts include, but are not limited to, salts formed with cations (e.g., sodium, potassium, calcium, or polyamines such as spermine); acid addition salts formed with inorganic acids (e.g., hydrochloric acid, hydrobromic acid, sulfuric acid, phosphoric acid, or nitric acid); salts formed with organic acids (e.g., acetic acid, citric acid, oxalic acid, palmitic acid, or fumaric acid); and salts formed with elemental anions (e.g., bromine, iodine, or chlorine).

Compositions additionally can contain other adjunct components conventionally found in pharmaceutical compositions. Thus, the compositions also can include compatible, pharmaceutically active materials such as, for example, antipruritics, astringents, local anesthetics or anti-inflammatory agents, or additional materials useful in physically formulating various dosage forms of the compositions of the present invention, such as dyes, flavoring agents, preservatives, antioxidants, opacifiers, thickening agents, and stabilizers. Furthermore, the composition can be mixed with auxiliary agents, e.g., lubricants, preservatives, stabilizers, wetting agents, emulsifiers, salts for influencing osmotic pressure, buffers, colorings, flavorings, penetration enhancers, and aromatic substances. When added, however, such materials should not unduly interfere with the biological activities of the PNA components within the compositions of the present invention.

Pharmaceutical formulations as disclosed herein, which can be presented conveniently in unit dosage form, can be prepared according to conventional techniques well known in the pharmaceutical industry. Such techniques include the step of bringing into association the active ingredients (i.e., the antibodies) with the desired pharmaceutical carrier(s). Typically, the formulations can be prepared by uniformly and intimately bringing the active ingredients into association with liquid carriers or finely divided solid carriers or both, and then, if necessary, shaping the product. Formulations can be sterilized if desired, provided that the method of sterilization does not interfere with the effectiveness of the antibody(s) contained in the formulation.

Compositions can be formulated into any of many possible dosage forms such as, without limitation, tablets, capsules, liquid syrups, soft gels, suppositories, and enemas. Compositions also can be formulated as suspensions in aqueous, non-aqueous or mixed media. Aqueous suspensions further can contain substances that increase the viscosity of the suspension including, for example, sodium carboxymethyl-cellulose, sorbitol, and/or dextran. Suspensions also can contain stabilizers.

5. Methods

The invention provides methods for using molecules described herein to enhance DC function and potentiate an immune response. Molecules described herein can interact specifically with B7-DC and, as described herein, can enhance the function of DC and potentiate an immune response. Methods provided by the invention can be particularly useful for treating tumors and inducing immunity to a specific antigen.

The invention also provides methods for using molecules described herein to treat, prevent, or inhibit development of allergic asthma in a mammal. In addition, the invention provides methods modulating an existing state of immune response in a mammal, and for inhibiting a Th2 immune response in a mammal.

The methods provided herein typically include administering to a mammal (e.g., a dog, a cat, a horse, a cow, a rabbit, a rat, a mouse, or a human) a molecule of the invention (e.g., an antibody such as sHIgM12) or a composition of the invention (e.g., a composition containing sHIgM12). Methods of the invention also involve administration of DC that have been contacted with a molecule or a composition provided herein (e.g., a compositions containing sHIgM12 and an antigen). Such DC are useful to potentiate an immune response in the mammal to which they are administered.

As described above, the molecule, composition, or activated DC can be administered by any suitable systemic or local method. Systemic methods of administration include, without limitation, oral, topical, or parenteral administration, as well as administration by injection. Local methods of administration include, for example, direct injection into a tumor.

Methods provided herein also can be used to modulate (e.g., enhance) DC function. The enhancement of DC function includes, for example, prolonging the longevity of DC, increasing the ability of DC to activate naïve T cells, and increasing the localization of DC to lymph nodes in a mammal. The longevity of DC can be assessed by, for example, measuring the expression of NF-κB or the translocation of NF-κB to the nucleus. Since NF-κB is an intracellular signal involved in the inhibition of programmed cell death, increased expression or translocation of NF-κB indicates inhibition of apoptosis and prolonged DC longevity. T cell activation can be measured by, for example, assessing the incorporation of radiolabeled (e.g., tritiated) thymidine into newly synthesized DNA in proliferating T cells. Activation of naïve T cells also can be measured by detecting (e.g., by flow cytometry) CD44 and/or CD69 activation markers on the T cell surface.

Methods for potentiating an immune response (i.e., inducing immunity to a particular antigen) can involve administering to a mammal (e.g., a human) a composition that contains (1) a purified molecule (e.g., a polypeptide or an antibody, particularly sHIgM12) capable of binding specifically to B7-DC polypeptides, and (2) an antigen (e.g., an antigen from a tumor cell or from a pathogen). Such methods also can involve administering DC that have been activated in vitro by contacting the cells with (1) a purified molecule (e.g., a polypeptide or an antibody such as sHIgM12) capable of binding specifically to B7-DC polypeptides, and (2) an antigen (e.g., an antigen from a tumor cell or from a pathogen). These methods are useful to, for example, treat tumors and/or induce immunity to pathogens.

Methods of the invention can be useful for treating solid tumors including, without limitation, breast cancer, lung cancer, pancreatic cancer, brain cancer, prostate cancer, ovarian cancer, uterine cancer, renal cancer, melanoma, and other solid tumors. Such methods are particularly useful for treating melanoma and renal carcinoma tumors. A solid tumor can be, for example, an early-stage solid tumor. As used herein, the term "treating a tumor" encompasses reducing the size of a tumor, reducing the number of viable cells in a tumor, and/or slowing or stopping the growth of a tumor. Methods for assessing such outcomes are known in the art. Methods for treating tumors can involve administration of a molecule or composition of the invention (e.g., a composition containing sHIgM12 and a tumor antigen) either systemically (e.g., intravenously or subcutaneously) or directly to a tumor (e.g., by injection).

The invention also provides methods that can be used to treat or inhibit development of allergic asthma in a mammal. These methods can result in reduced asthmatic symptoms in the mammal. For example, administration of a molecule such as sHIgM12 can result in a decreased level of previously observed symptoms, or can result in decreased development of new symptoms. Symptoms of asthma can include, without limitation, coughing, wheezing, shortness of breath or rapid breathing, and chest tightness, AHR (e.g., in response to methacholine challenge), increased cellular infiltrates in bronchoalveolar lavage fluid, and eosinophil migration to the lungs.

Methods for treating or inhibiting development of allergic asthma can include administering to a mammal (e.g., a dog, a cat, a horse, a cow, a rabbit, a rodent, or a human) an effective amount of a B7-DC cross-linking molecule, or an effective amount of a composition containing such a molecule. As used herein, the term "effective amount" is an amount of a molecule or composition that is sufficient to reduce or inhibit development of asthma symptoms in a mammalian recipient by at least 10%, or that can increase airflow, lung capacity, and/or airway reactivity by at least 10% (e.g., 10%, 15%, 20%, 25%, 30%, 40%, 50%, 60%, 70%, 75%, 80%, 85%, 90%, 95%, 99%, or 100%). In some embodiments, methods of the invention can include administering to a mammal an amount of a composition that is sufficient to reduce or inhibit development of asthma symptoms by at least 50%.

For example, an "effective amount" of a molecule (e.g., an antibody such as sHIgM12) can be an amount that reduces or inhibits development of an asthma symptom (e.g., AHR) in a treated mammal by at least 10% as compared to the level of the symptom in the mammal prior to administration of the molecule or without administration of the molecule (e.g., the level of the symptom observed in a previous asthmatic episode). Thus, if an untreated mammal exhibits AHR during methacholine challenge at a particular concentration of methacholine, treatment of the mammal with an effective amount of a B7-DC cross-linking molecule will either result in no AHR, or will result in AHR at a concentration of methacholine that is at least 10% greater than the first concentration. AHR can be measured by determining airway responsiveness to methacholine challenge as described herein. Alternatively, an effective amount of a B7-DC cross-linking molecule in a mammal exposed to an asthma-triggering allergen such as dust mites, pet dander, pollen, or mold can reduce the existence or development of symptoms such as coughing or wheezing by at least 10%, or can reduce the number of cellular infiltrates in BAL fluid by at least 10%. In addition, an effective amount of a B7-DC cross-linking molecule can increase airflow rate and airway capacity by at least 10%. Such parameters can be measured using, for example, a spirometry breathing test.

6. Articles of Manufacture

The invention provides articles of manufacture that can include one or more molecules and/or compositions disclosed herein. The molecule and/or composition can be combined with packaging material and sold as kits for treating or reducing development of allergic asthma. The molecule and/or composition can be in a container such as a vial, a tube, or a syringe, for example, and can be at least partially surrounded with packaging material. Components and methods for producing articles of manufacture are well known.

Articles of manufacture may combine one or more of the molecules set out in the above sections. For example, an article of manufacture can contain a composition that includes a molecule provided herein (e.g., an antibody such as sHIgM12 or a polypeptide such as immobilized PD-1). An article of manufacture also can include one or more antigens (e.g., a tumor antigen or an antigen from a pathogen) that can stimulate a specific immune response. Furthermore, an article of manufacture can contain DC. An article of manufacture also may include, for example, buffers or other control reagents for potentiating an immune response. Instructions indicating that the molecules, antigens, DC, and/or compositions are effective for potentiating an immune response or for treating or reducing development of allergic asthma also can be included in such kits.

The invention will be further described in the following examples, which do not limit the scope of the invention described in the claims.

EXAMPLES

Example 1

Materials and Methods for Isolating and Characterizing sHIgM12

Isolation of human antibodies—Human serum samples were obtained from the dysproteinemia clinic, and those exhibiting an Ig clonal peak of greater than 20 mg/ml were chosen for further evaluation. The selected samples were from 50 patients with a wide variety of conditions characterized by a monoclonal IgM spike, including Waldenstrom's macroglobulinemia, lymphoma, and monoclonal gammopathy of undetermined significance. Sera were dialyzed against water, and precipitates were collected by centrifugation at 14,000 rpm for 30 minutes and dissolved in phosphate buffered saline (PBS). The samples were centrifuged and subjected to chromatography on a SUPEROSE-6™ column (Amersham Pharmacia, Piscataway, N.J.). IgM fractions were pooled and analyzed by SDS-PAGE, and protein concentrations were determined by reading absorbance at 280 nm. IgM solutions were sterile filtered and cryopreserved. The antibody sHIgM12 was identified based on its ability to bind DC as determined by FACS analysis (see Example 2). The polyclonal human IgM antibody control was described previously (Miller et al. (1994) *J. Neurosci.* 14:6230-6238).

Monomeric sHIgM12 was obtained from the pentameric form by reduction with 5 mM dithiothreitol (Sigma-Aldrich, St. Louis, Mo.) in 200 mM Tris, 150 mM NaCl, 1 mM EDTA pH 8.0 for 2 hours at room temperature. Subsequent alkylation was performed with 12 mM iodacetamide for 1 hour on ice. IgM monomers were isolated by chromatography on a Superdex-200 column (Amersham Pharmacia) equilibrated with PBS, and characterized by reducing and non-reducing SDS-PAGE.

Mice and reagents—C57BL6/J, C3H/HeJ, and BALB/C mouse strains were obtained from The Jackson Laboratory (Bar Harbor, Me.). OT-1 and D0-11 transgenic mouse strains (Hogquist et al. (1994) Cell 76:17-27; and Murphy et al. (1990) Science 250:1720-1723) were bred and maintained at the Mayo Clinic animal facility according to the protocol approved by the Institutional Review Board for Animal Rights, Mayo Clinic. C57BL/6-RAG$^{-/-}$ mice, CD4$^{-/-}$ mice, and GFP transgenic mice were purchased from The Jackson Laboratory (Bar Harbor, Me.). β2-microglobulin knockout mice were obtained from Francois Lemmonier, Pasteur Institute, Paris. Chicken OVA was obtained from Sigma-Aldrich. Peptides were synthesized at the Mayo Protein Core Facility. Fluorophore-coupled anti-CD11c(HL-3), anti-B220(RA3-6B2), anti-CD80(16-10A1), anti-CD86(GL-1), anti-CD44 (IM7), anti-CD69(H1.2F3), anti-CD3e(145-2C11), anti-Mac1(M1/70), Pan-NK antibody(DX-5), anti-K$^b$(AF6-88.5), and anti-1-A$^b$(KH74) were obtained from BD PharMingen (San Diego, Calif.). FITC-coupled goat anti-human IgM was obtained from Jackson ImmunoResearch Laboratories, Inc. (West Grove, Pa.). The K$^b$-Ser-Ile-Ile-Asn-Phe-Glu-Lys-Leu (SEQ ID NO:1) tetramer coupled to APC was prepared as previously described (Block et al. (2001) J. Immunol. 167: 821-826). RPMI-1640 medium was purchased from Gibco/Invitrogen (Carlsbad, Calif.).

Generation of immature and mature DC in vivo—DC from bone marrow were isolated using an established protocol. Briefly, bone marrow was isolated from mouse hind leg long bones. Erythrocytes were lysed by treatment with ammonium chloride-potassium chloride (ACK; 0.1 M NH$_4$Ac, 0.01 M KHCO$_3$, 60 µM EDTA) at 37° C. The remaining cells were plated at a density of 1×10$^6$ cells per ml in 6 well plates (Becton Dickinson, Franklin Lakes, N.J.) in RPMI-10 containing 10 µg/ml murine granulocyte macrophage-colony stimulating factor (GM-CSF; PeproTech, Inc., Rocky Hill, N.J.) and 1 ng/ml murine interleukin-4 (IL-4; PeproTech, Inc.). Cells were incubated at 37° C. with 5% CO$_2$. On culture day 2, cells were gently washed and the media was replaced with fresh RPMI-10 containing the same concentrations of GM-CSF and IL-4, and the culture was continued for another 5 days. DC were matured by the addition of either 10 µg/ml lipopolysaccharide (LPS; Difco®) or 50 µmol/ml CpG (Mayo Molecular Core Facility) to the cultures for 48 hours. Maturation status was confirmed by staining for Class-11, CD80, and CD86.

Human DC were derived from monocytes cultured with GM-CSF and IL-4. Day 7 cells were activated with either LPS (10 µg/ml), TNF-α/IL-113 (1.1×10$^4$ U/ml and 3.2×10$^3$ U/ml, respectively), interferon-γ (IFN-γ; 2×10$^3$ U/ml), or PBS control for 3 days. DC development was followed by monitoring the presence of the CD83 cell surface marker, as described below.

Flow cytometry—Cells were washed with fluorescence activated cell sorting (FACS) buffer (0.5% bovine serum albumin (BSA) and 0.1% sodium azide in PBS) and centrifuged into a 96-well plate (Nunc). Antibodies were added to the wells for a 30 minute incubation on ice. After three washes with FACS buffer, cells were fixed with 1% paraformaldehyde and analyzed on a FACSCALIBUR™ (Becton Dickinson). Data were analyzed using CELL QUEST™ software (BD PharMingen).

Activated human DC were stained with 10 µg/ml of sHIgM12 or polyclonal hIgM control on culture day 10 (3 days after induction of maturation). FITC-conjugated anti-hIgM secondary antibody was added after several washes. CD83 is a maturation marker on DC, and was assessed by anti-human CD83-PE antibody.

Human TP365 glioma cells were obtained from Dr. Robert Jenkins at the Mayo Clinic (Rochester, Minn.). Cells were stained with 10 µg/ml sHIgM12 or polyclonal hIgM control. A secondary anti-human IgM, Fc$_5$µ, fragment specific FITC-conjugated antibody (Jackson Immunoresearch Laboratories) was added after 2 washes. Cells subsequently were washed and fixed with 2% paraformaldehyde, and subjected to flow cytometry analysis.

Isolation of endogenous DC-DC were isolated from mouse spleen and thymus. Tissues were cut into small pieces and incubated in RPMI containing 2 mg/ml collagenase (Sigma-Aldrich), 100 µg/ml DNAse (Sigma-Aldrich), and 2% fetal calf serum (Hyclone) for 20 minutes at 37° C. EDTA (0.031 M) was added for 5 minutes. Erythrocytes were lysed with ACK at 37° C., and the remaining cells were counted and used for flow cytometry.

In vitro activation of naïve T cells—Naïve splenocytes were harvested from mice and plated in triplicate after erythrocyte lysis using ACK buffer. 3×10$^5$ responder cells were stimulated in vitro for three days with titrating doses of antigen or antigen-pulsed DC. The plated cells were pulsed with $^3$H-thymidine during the final 18 hours before they were harvested and $^3$H levels determined.

Adoptive transfer of DC and T cells—DC derived from seven-day bone marrow cultures were pulsed overnight with 1 µmol/ml of the class-I restricted peptide Ser-Ile-Ile-Asn-Phe-Glu-Lys-Leu (SEQ ID NO:1) or the class-II restricted peptide Ile-Ser-Gln-Ala-Val-His-Ala-Ala-His-Ala-Glu-Ile-Asn-Glu (SEQ ID NO:2), or with 1 mg/ml chicken OVA. The control antibody or sHIgM12 was co-incubated with the peptide in the cultures at a concentration of 10 µg/ml. Cells were harvested the next day and washed three times with PBS, and 10$^7$ cells per mouse were injected intravenously for in vivo priming of T cells.

For experiments to monitor cell division, OT-1 splenocytes were labeled with 5 µM 5- (and 6-) carboxyfluorescein diaceteate succinimidyl ester (CFSE) for 20 minutes at 37° C. prior to adoptive transfer. Following three washes with PBS, 10$^7$ CFSE-labeled splenocytes were intravenously injected into each mouse. DC and T cells were administered in separate injections. Spleen cells were harvested 2 or 7 days after adoptive transfer and either analyzed directly by flow cytometry or incubated in culture with various concentrations of OVA for three additional days. Cultures were pulsed with $^3$H-thymidine overnight before harvesting and evaluation for $^3$H incorporation as a measure of T cell activation.

Competition for binding—PD-1.Ig was acquired from Lieping Chen at the Mayo Clinic (Rochester, Minn.). The plasmid encoding PD-1.Ig was originally obtained from Drew Pardoll (Johns Hopkins University, Baltimore, Md.). The plasmid was transformed into CHO cells (ATCC, Manassas, Va.), and PD-1.Ig was isolated from culture supernatants using protein G columns (Pharmacia). DC were preincubated with PD-1.Ig for 20 minutes at 4° C. before addition of sHIgM12 and subsequent staining with a fluorescein isothiocyanate-(FITC-) conjugated secondary antibody. For the reverse experiments, cells were preincubated with sHIgM12 before addition of PD-1.Ig. An isotype control antibody was used as a control.

Staining of transfected cells—293-T cells and P815 cells were obtained from ATCC. Cells were transiently transfected with expression plasmids encoding either B7-DC or B7-H1 and stained with sHIgM12, PD-1.Ig, or an isotype control antibody.

Ltk cells (ATCC) were transiently transfected with 2.5 µg of pcDNA3.1 (Invitrogen, Carlsbad, Calif.) or 0.5 µg to 10 µg of pcDNA3.1-hB7.DC expression plasmids. After 48 hours, cells were stained with sHIgM12 or polyclonal hIgM control. FITC-conjugated anti-hIgM secondary antibody was added after several washes.

In vivo assays—To evaluate in vivo effects of sHIgM12 on T cell proliferation, mice were treated with 10 µg of sHIgM12 or polyclonal HIgM control on days −1, 0, and +1, and intravenously injected with 1 mg OVA on day 0. On day 7, splenocytes were isolated and pulsed with concentrations of OVA ranging from 1 ng/ml to 1 mg/ml. After three days of culture in vitro, cells were incubated with 1 µCi of $^3$H-thymidine for 16 hours before harvest and determination of $^3$H incorporation.

The effect of sHIgM12 on a lethal tumor cell challenge was evaluated in C57BL/6J mice, C57BL/6-RAG$^{-/-}$ immunodeficient mice, 132-microglobulin knockout mice (K$^-$D$^-$), and CD4$^{-/-}$ knockout mice. The animals received 10 µg of sHIgM12, polyclonal HIgM control, or PBS intravenously on days −1, 0, and +1. All mice received a subcutaneous injection of 2×10$^4$ B16 melanoma cells in the flank on day 0. The presence of tumors was evaluated starting on day 10. Data were pooled from three separate trials. Categorical data was analyzed using Chi-square distribution (C57BL/6J) or Fischer exact test (C57BL/6-RAG$^{-/-}$, CD4$^{-/-}$ and K$^-$D$^-$).

For studies of tumor growth, the width and length of subcutaneous tumors were measured on day 17 (C57BL/6) or day 13 (C57BL/6-RAG$^{-/-}$). The product of width and length was used as an estimate of tumor size. Statistical comparisons were made using ANOVA.

To evaluate the persistence of anti-tumor resistance in tumor survivors, C57BL/6 mice that survived otherwise lethal B16 melanoma challenge were rechallenged with 2×10$^4$ tumor cells 30 or more days after the primary challenge. Rechallenge was administered on the opposite flank from the primary challenge. No further antibody treatments were administered. As reference points for comparison, naïve animals were treated with sHIgM12 or polyclonal HIgM control and challenged with the same dose of tumor cells. Developing tumors were measured (width and length) on day 14, and data were analyzed by ANOVA.

Cytokine withdrawal assay—Day 5 DC were plated on 96-well plates at 2×10$^4$ cells per well. Cells were cultured with sHIgM12, A2B5 control antibody, or media to a final concentration of 10 µg/ml in RPMI-10 with 10 µg/ml granulocyte macrophage-colony stimulating factor (GM-CSF) and 1 ng/ml interleukin-4 (IL-4). Alternatively, DC were contacted with immobilized PD-1.Ig prior to plating and culturing in RPMI-10 with GM-CSF and IL-4. Cells were cultured for 5 days before cytokine withdrawal. For cytokine withdrawal, cells were washed and cultured in RPMI-10 alone. After 1 hour, Alamar Blue (Biosource International, Camarillo, Calif.) was added to a final concentration of 10% (v/v). Readings were taken at 6 hour intervals on a CYTOFLUOR® multiplate reader (Series 4000, PerSeptive Biosystems, Framingham, Mass.). The fluorescence plate reader was set to an excitation wavelength of 520 nm and an emission wavelength of 590 nm. Each data point was done in triplicate.

Assessment of DC migration to lymph nodes—Bone marrow from GFP transgenic mice was used to derive GFP DC. In some experiments, the cells were pulsed with a Ser-Ile-Ile-Asn-Phe-Glu-Lys-Leu (SEQ ID NO:1) peptide and then treated with sHIgM12 or an isotype control antibody for 16 hours or over night. Cells were subcutaneously injected into mice, and then isolated from the ipsilateral popliteal and inguinal lymph nodes 48 hours after transfer. Contralateral lymph nodes from both treatment groups served as controls. To measure the number of GFP DC that migrated to the lymph nodes, samples were stained with PE-conjugated CD11c antibody and analyzed by flow cytometry.

To assess the effect of these GFP DC, splenocytes from OT-1 T cell receptor (TcR) transgenic mice (3×10$^5$ T cells per well) were co-cultured for 4 days with titrated numbers of cells from the ipsilateral draining lymph nodes of mice treated as described above. Cells were pulsed with 1 mCi of $^3$H-thymidine per well for the final 16 hours of the incubation, and then harvested for measurement of $^3$H incorporation. Each group was performed in triplicate.

In related studies, GFP DC were mixed with sHIgM12 or control antibody (10 µg/ml) immediately prior to transplantation, and the migration of the cells to lymph nodes was assessed as described above. In another group of studies, the cells were transferred without antibody and the mice received three i.v. tail injections of 10 µg sHIgM12 or HIgM control on days −1, 0, and +1 relative to the transplant. Again, lymph nodes were harvested and analyzed as described above.

IL-12 measurement—Day 7 bone marrow derived DC were treated with sHIgM12, polyclonal HIgM control, or LPS at a final concentration of 10 µg/ml. Supernatants were collected 96 hours after stimulation and an ELISA (BD PharMingen, San Diego, Calif.) was performed for the active fraction of IL-12. The supernatant tested for each treatment group was pooled from 6 separate wells. Experimental groups were tested in triplicate and at numerous dilutions, with each demonstrating a similar profile.

Example 2

A Monoclonal Human IgM Antibody Binds Mouse DC

DC were obtained in culture following incubation of mouse bone marrow cells in media supplemented with GM-CSF and IL-4. Cells from seven day cultures were incubated with purified antibodies isolated from human sera, and stained with fluoresceinated goat anti-human antibody as well as antibodies specific for cell surface molecules typically expressed on DC. As shown in FIG. 1, the human antibody sHIgM12 bound cells in the cultures that expressed high levels of CD11c, class II, and CD86. Polyclonal human IgM, as well as the other tested monoclonal antibodies from patients with gammopathies or from EBV-transformed cell lines did not appreciably bind the DC populations.

To determine when the cell surface determinant recognized by the sHIgM12 antibody first appears during the in vitro development of DC, cultured cells were analyzed by flow cytometry at various times during the culture procedure. The determinant first appeared on day 5, approximately 2 days after the appearance of cells expressing high levels of the DC marker CD11c. The determinant was expressed at even higher levels in cells cultured in the presence of LPS and CpG, two molecular signals associated with bacterial infection.

DC isolated from various tissues were examined to establish whether endogenous cells express the determinant bound by sHIgM12 antibody. DC freshly isolated from spleen, thymus, and bone marrow all were stained by the sHIgM12 antibody. In contrast, most other bone marrow cells, splenic B cells, splenic T cells, and splenic macrophages were not appreciably stained by sHIgM12. B cells, T cells, NK cells, and macrophages were activated with LPS or concanavalin A to assess whether activated lymphoid or monocytic cells express the antigen. None of the activated cells from these lineages bound sHIgM12. The sHIgM12 antibody therefore appears to bind a cell surface molecule expressed selectively by DC, and this determinant is expressed increasingly as the DC mature and become activated.

Example 3

The sHIgM12 Antibody Potentiates Dendritic Antigen-Presenting Function

To determine whether binding of sHIgM12 to the surface of DC influences the pattern of expressed cell surface molecules, day 7 DC cultures were supplemented with 10 µg/ml antibody, incubated overnight, and analyzed by flow cytometry. Changes in the cell surface markers (e.g., class II B7-I and B7-II) were not observed.

Figure 2B:
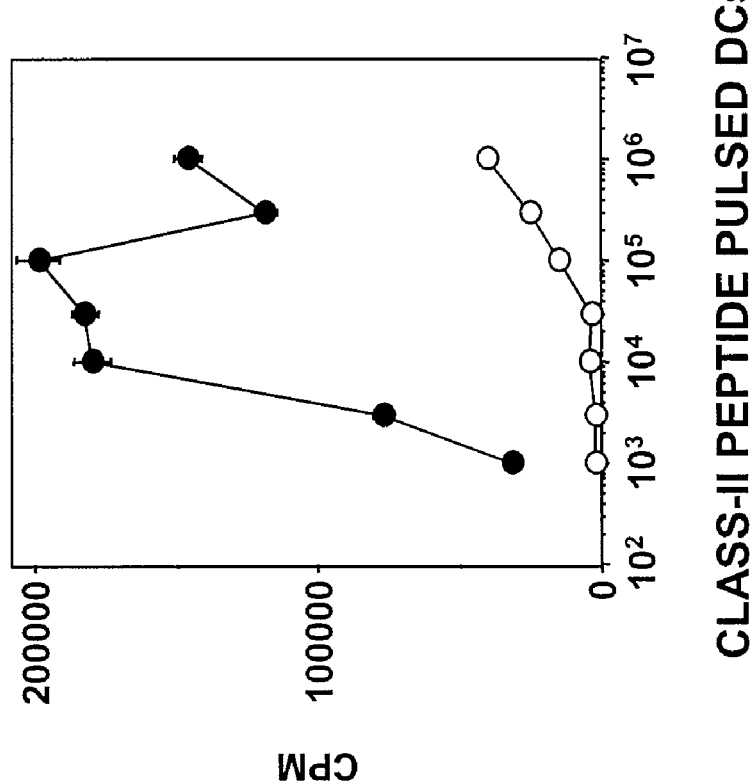
FIGS. 2A and 2B are line graphs showing the effect of sHIgM12-treated, antigen-pulsed DC on incorporation of 3H-thymidine into T cells, an indicator of proliferation.
Figure 2A:
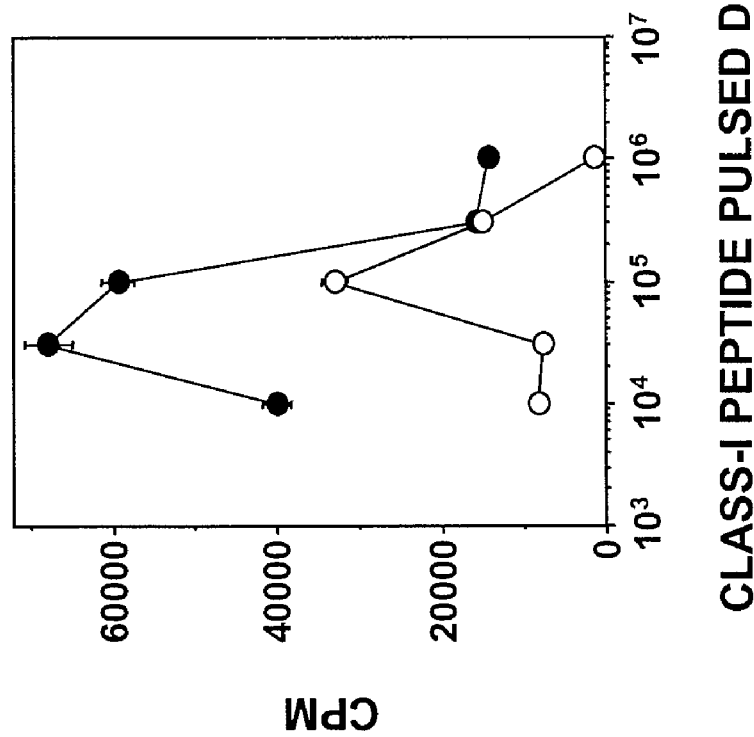

The antigen-presenting functions of the DC were assessed in vitro. Antibody-treated DC were pulsed with peptide antigen and used to stimulate naïve antigen-specific T cells freshly isolated from OT-1 and DO-11 transgenic mice. T cell activation was measured by incorporation of $^3$H-thymidine as described in Example 1. DC that were pulsed with a class I-binding peptide (Ser-Ile-Ile-Asn-Phe-Glu-Lys-Leu; SEQ ID NO:1) and incubated with polyclonal HIgM control antibody were able to activate naïve CD8 T cells from OT-1 mice. DC treated with the same peptide and incubated with the monoclonal sHIgM12 antibody activated naïve T cells approximately 10-fold more effectively, as judged by the number of antigen-pulsed DC required to induce the incorporation of $^3$H-thymidine (FIG. 2A). BALB/c DC pulsed with a peptide (Ile-Ser-Gln-Ala-Val-His-Ala-Ala-His-Ala-Glu-Ile-Asn-Glu; SEQ ID NO:2) presented by class II molecules were even more effective at activating naïve T cells freshly isolated from DO-11 TcR transgenic mice. Greater than 100-fold more DC treated with polyclonal HIgM control antibody were needed to activate T cells to levels observed with sHIgM12-treated DC (FIG. 2B). These experiments demonstrated that the antigen-presenting functions of DC were dramatically enhanced by treatment of DC with sHIgM12.

To assess the requirement for direct contact between DC and T cells in the potentiation of T cell activation, the two cell types are cultured in compartmentalized tissue culture plates that allow soluble factors to move between chambers but do not allow cellular contact between chambers. Alternatively, antibody-depleted supernatants from DC cultures treated with sHIgM12 are incubated with cultures of transgenic spleen cells or transgenic spleen cells mixed with DC pulsed with specific antigen.

Figure 3:
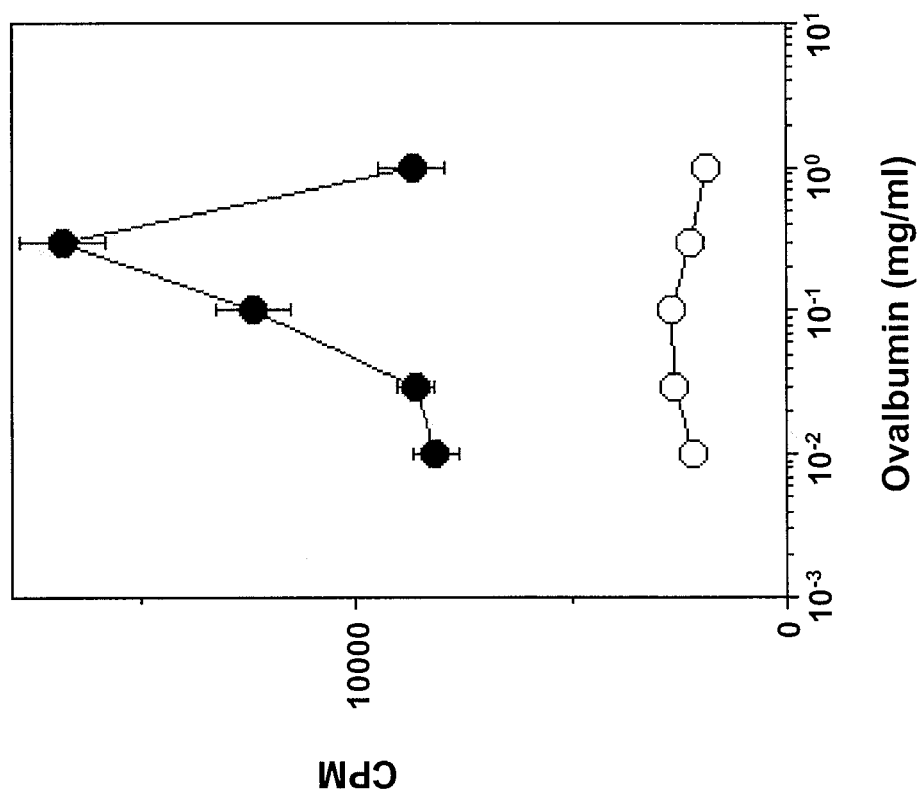
FIG. 3 is a line graph showing the effect of sHIgM12 treated, antigen-pulsed DC on in vivo T cell priming. Mouse DC were pulsed with OVA and treated with sHIgM12 (open circles) or polyclonal HIgM control (closed circles) prior to adoptive transfer. The data depict levels of 3H incorporation into splenocytes that were harvested 7 days after adoptive transfer and treated with titrating doses of OVA.

The ability of antigen-pulsed, antibody-treated DC prepared in vitro to stimulate splenic T cells in vivo was evaluated in C3H/HeJ mice. This inbred strain is genetically defective at the TLR-4 locus and consequently is not responsive to LPS, an activator of DC. Day 7 cultures of mouse bone marrow-derived DC were incubated overnight with chicken OVA and sHIgM12 or polyclonal HIgM control antibody, and $10^7$ cells were intravenously infused into each mouse. After seven days, spleen cells were removed from the animals, incubated in vitro with various amounts of OVA for three days, and T cell activation was measured by incorporation of $^3$H-thymidine. As shown in FIG. 3, spleen cells from animals that had received sHIgM12-treated DC responded much more vigorously to secondary challenge with OVA than did spleen cells from mice that received DC treated with polyclonal HIgM control. DC treated in culture with sHIgM12 therefore displayed enhanced ability to stimulate T cells in vivo. Because DC from the TLR-4 deficient mice were responsive to sHIgM12 treatment, possible contamination by LPS was not a factor in these experiments. In parallel studies, polymixin B was added to the DC cultures to inactivate potential LPS contaminants. Polymixin B had no influence on DC function following treatment with sHIgM12, although it was effective in reducing maturation of the DC when LPS was added directly to the cultures.

To visualize what was happening to the T cells in vivo, C57BL/6 antigen-pulsed, antibody-treated DC were adoptively transferred along with transgenic OT-1 cells into C57BL/6 hosts. OT-1 T cells were identified in these experiments by probing with $K^b$:Ser-Ile-Ile-Asn-Phe-Glu-Lys-Leu (SEQ ID NO:1) tetramers. Spleen cells were recovered 2 or 7 days after transfer, and tetramer-positive T cells were analyzed by flow cytometry to determine their activation state. T cells stimulated in vivo by DC pretreated with sHIgM12 expressed substantially higher levels of the activation markers CD44 and CD69 two days after transfer as compared to T cells stimulated by DC pretreated with PBS. By day 7, cells remaining in the spleen were less activated, but cells transferred into mice receiving sHIgM12-treated DC still expressed higher levels of CD44 and CD69. DC not treated with antigen had no effect on the activation of transgenic T cells upon adoptive transfer, whether pretreated with sHIgM12 or not. Treatment with sHIgM12 therefore potentiated the ability of DC to activate T cells in vivo.

Example 4

The Pentameric Structure of sHIgM12 Facilitates DC Potentiation

Figure 4B:
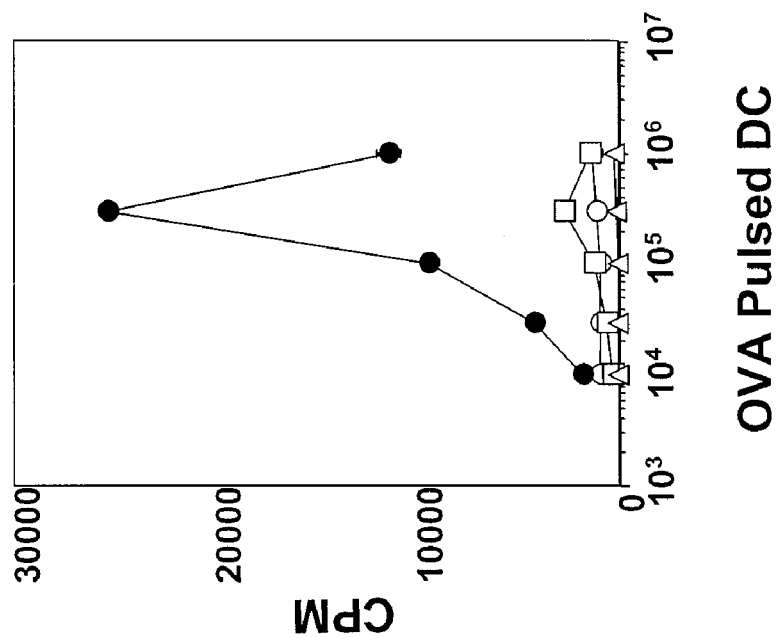
FIG. 4B is a line graph showing levels of activation of naïve OT-1 splenocytes by DC treated with pentameric sHIgM12 (filled circles), polyclonal HIgM control (open circles), monomeric sHIgM12 (open squares), and monomeric sHIgM12 followed by pentameric sHIgM12 (open triangles).
Figure 4A:
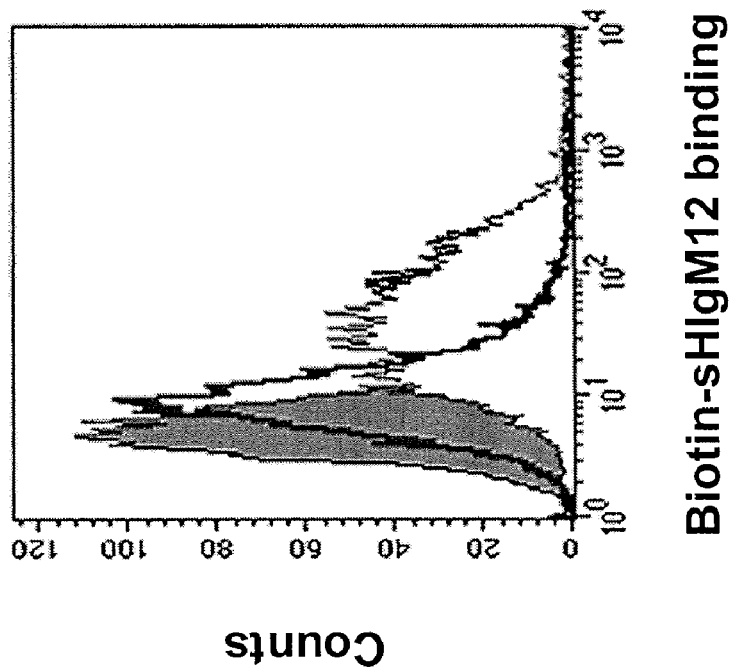
FIG. 4A is a histogram showing amounts of DC staining by sHIgM12 (gray filled histogram), polyclonal HIgM control (black filled histogram), and monomeric sHIgM12 (thick black line outlining unfilled histogram).

To test the hypothesis that low affinity IgM antibodies have the ability to activate cells because they cross-link multiple receptors on the cells surface of targeted cells, monomeric fragments of sHIgM12 were evaluated for their ability to stain DC, potentiate DC function, and block the ability of an intact sHIgM12 antibody to potentiate function. IgM monomers were significantly less effective than intact sHIgM12 at staining DC (FIG. 4A). However, the fragments did stain the cells more than polyclonal IgM antibodies, suggesting that they have intact, low affinity binding sites. Moreover, the antibody fragments were able to block the ability of intact IgM to potentiate DC antigen-presenting function (FIG. 4B). Overnight treatment with sHIgM12 monomers did not, however, potentiate the ability of DC to induce T cells to incorporate $^3$H-thymidine. The sHIgM12 antibody therefore may function by cross-linking multiple determinants on DC. The monomeric fragments can bind the determinants and thus block the ability of the pentamers to cross-link the relevant cell surface structures.

Example 5

B7-DC is the Cognate Receptor for sHIgM12 on Murine DC

Figure 5A:
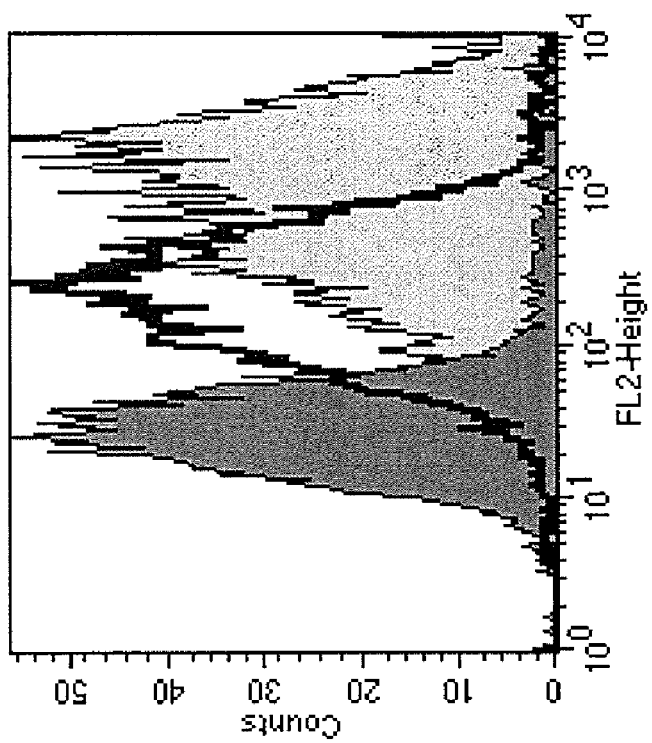
FIG. 5A is a histogram showing levels of sHIgM12 staining of DC (gray histogram) or DC preincubated with PD-1.Ig (unshaded histogram). A control antibody (black histogram) did not stain the cells.
Figure 5B:
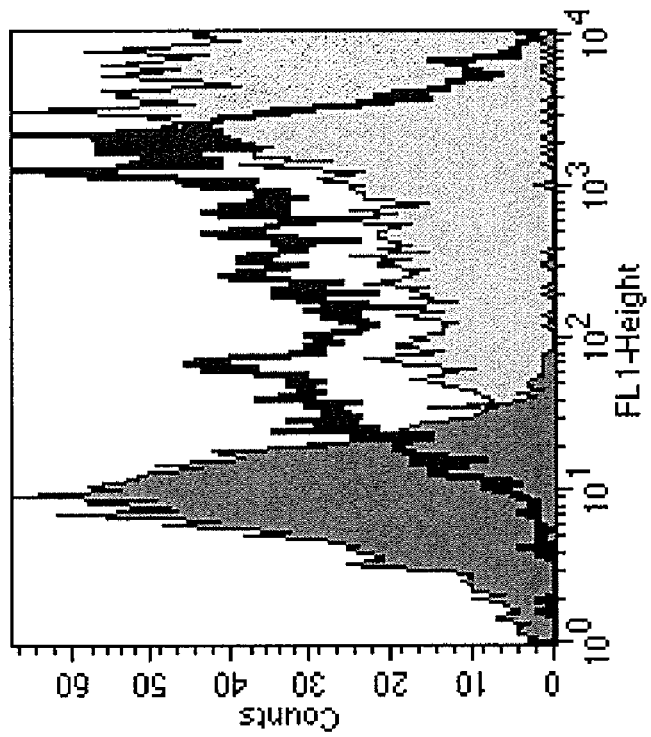
FIG. 5B is a histogram of the reciprocal experiment, showing PD-1.Ig staining of DC (gray histogram) or DC preincubated with sHIgM12 (unshaded histogram).
Figure 6A:
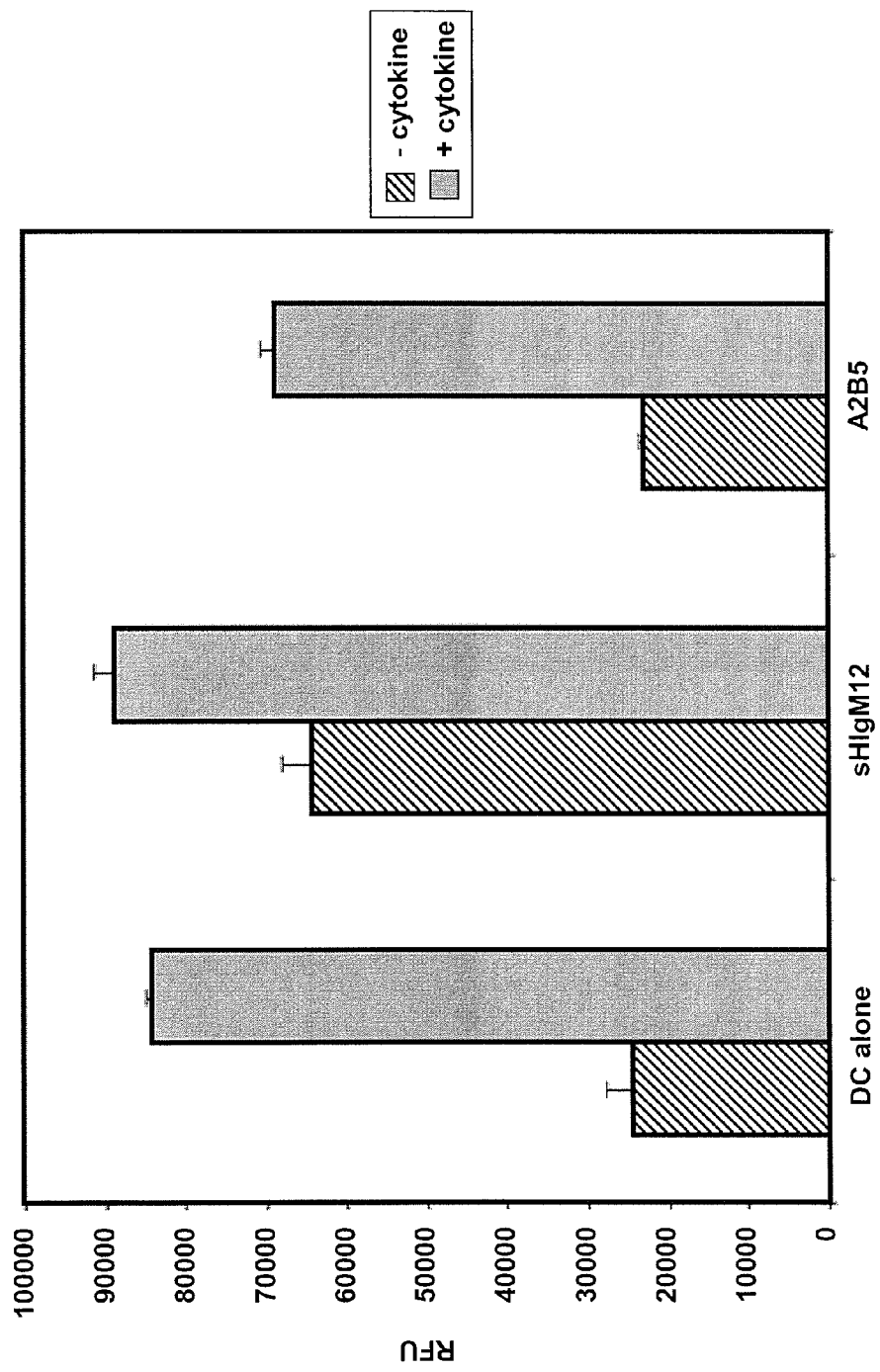
FIG. 6A is a column graph showing levels of DC metabolism before and after cytokine withdrawal from untreated cells and cells treated with either sHIgM12 or a control antibody as indicated.
Figure 6B:
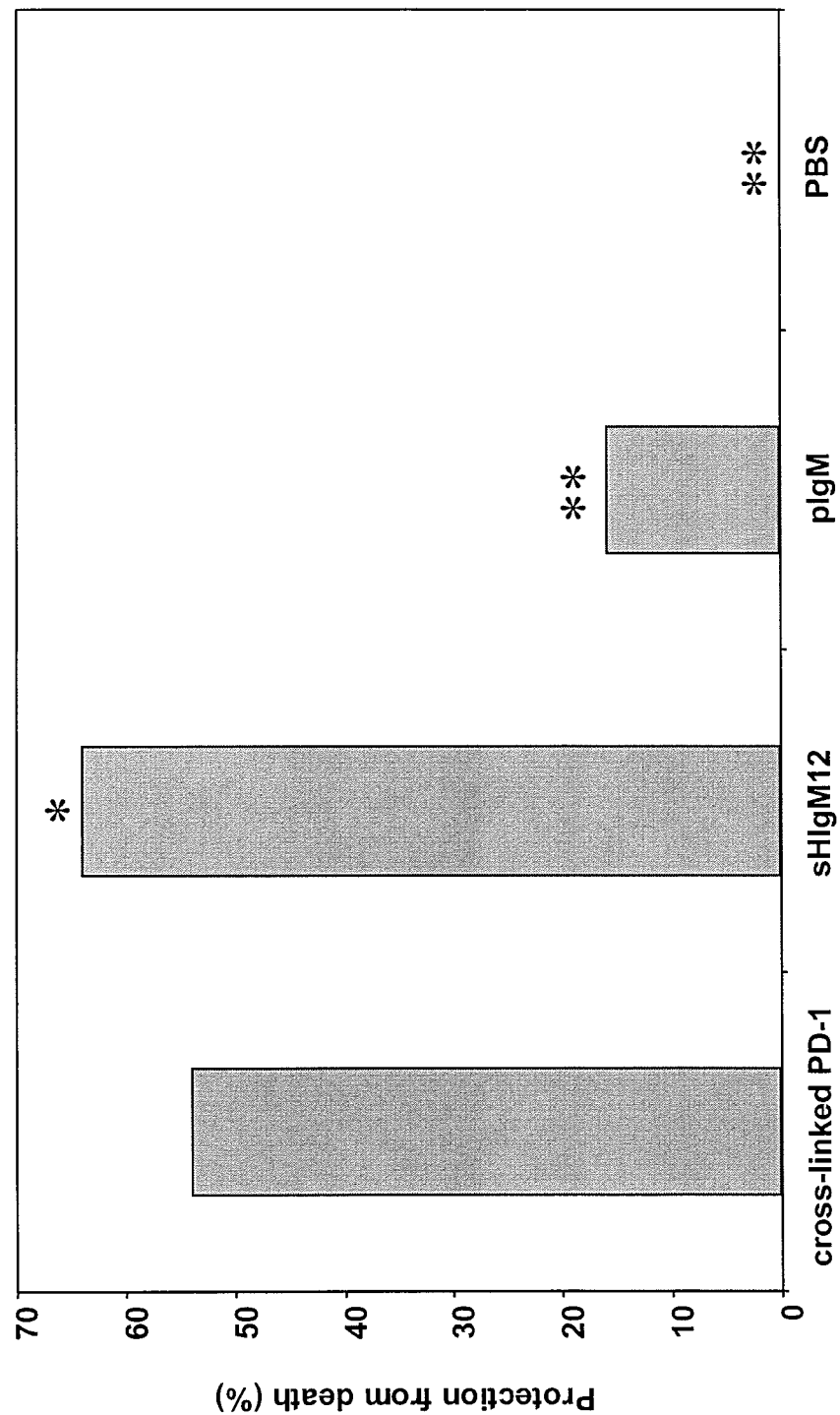
FIG. 6B is a column graph showing levels of DC metabolism before and after cytokine withdrawal from untreated cells and cells treated with either immobilized PD-1.Ig, sHIgM12, or a control antibody as indicated.

To determine the identity of the receptor for sHIgM12 on the surface of DC, murine bone marrow derived DC were incubated with or without a soluble PD-1.Ig fusion protein and stained with sHIgM12. Binding of the PD-1 fusion protein attenuated sHIgM12 staining to approximately 50% of the level observed in the absence of PD-1 (FIG. 5A). The reciprocal experiment showed that sHIgM12 also reduced the binding of PD-1 to DC to about 20% of the level observed in the absence of sHIgM12 (FIG. 5B). The higher avidity of the pentameric IgM antibody may contribute to the higher degree of competition by sHIgM12.

To investigate whether sHIgM12 can bind to B7-DC, 293T cells were transfected with a plasmid encoding murine B7-DC. $2\times10^5$ cells were plated and incubated overnight prior to transfection. 2 µg of the expression plasmid was mixed with 5 µA of FUGENE® (Roche) and incubated for 20 minutes in a 37° C. incubator. The mixture was pipetted directly onto the cells. The cells were cultured for 48 hours at 37° C., and then stained with either sHIgM12 or a control antibody. Flow cytometry revealed that approximately 97% of the transfected cells were stained by sHIgM12. Since the PD-1 receptor has been shown to have dual specificity for B7-DC and B7-H1, P815 cells were transfected with B7-H1 to determine whether the epitope for sHIgM12 is conserved between the two family members. sHIgM12 did not bind to P815 cells expressing B7-H1, indicating that the binding to B7-DC may be specific.

Example 6 sHIgM12 binding to B7-DC Directly Induces Functional Changes in DC

To examine whether binding of sHIgM12 to B7-DC directly affects DC biology, DC were treated in vitro with sHIgM12, polyclonal HIgM control, or LPS. The cells then were analyzed for their ability to (1) survive in culture following cytokine deprivation, (2) migrate to draining lymph nodes following adoptive transfer into naïve animals, and (3) secrete IL-12, a key immuno-modulator.

Prolonged survival of DC could lead to more effective interaction with T cells and thus potentiate immune responses. The possibility that sHIgM12 provides a survival signal to DC that would otherwise undergo apoptosis was investigated by cytokine withdrawal assays. Murine bone marrow-derived DC were plated on day 5 into 96-well plates. Cells were cultured with sHIgM12, A2B5 (a control antibody that binds DC), or media in RPMI-10 containing GM-CSF and IL-4. To achieve cytokines withdrawal, cells were washed in cultured in RPMI-10 alone. Alamar Blue was added one hour after withdrawal. The metabolism of Alamar Blue was measured at 6 hour intervals. The data represent the percentage of cellular metabolism that was maintained 24 hours after cytokine withdrawal, whereby 100% represents the level of metabolism when DC were cultured with GM-CSF and IL-4, and 0% arbitrarily represents complete cytokine withdrawal.

As shown in FIG. 6A, withdrawal of GM-CSF/IL-4 reduced metabolism to 29% of the level observed in cells cultured in cytokine-supplemented media. Incubating the cells with sHIgM12, however, resulted in 80% maintenance of metabolism levels 24 hours after cytokine withdrawal. Treatment with A2B5 did not significantly improve metabolism in the cultures as compared to treatment with media alone (33% vs. 29%). Additionally, treatment with sHIgM12 resulted in larger numbers of viable, Annexin-V negative DC 24 hours after cytokine withdrawal than were found in comparable cultures treated with control antibodies. In analogous experiments, DC were incubated with a PD-1.Ig fusion protein that was immobilized by binding to plastic plates. Treatment with the PD-1.Ig fusion maintained DC metabolism upon GM-CSF/IL-4 withdrawal in a manner comparable to treatment with sHIgM12 (FIG. 6B), and there was no statistical difference between the two groups. Cells contacted with PD-1.Ig maintained metabolism at statistically higher levels than cells treated with polyclonal HIgM control antibody or PBS ($p<0.05$). Other IgM antibodies known to bind to DC membranes also are useful for cytokine withdrawal experiments as described herein. Such antibodies include, for example, the anti-MHC class-I antibody 28-13-3 (specific for $K^b$) and the murine oligodendrocyte-binding antibody 94.03.

The anti-apoptotic activity induced by sHIgM12 indicated that the antibody may induce intracellular signals that inhibit programmed cell death. To evaluate this possibility, bone marrow cells were cultured with GM-CSF and IL-4 for 7 days. Cells were treated with sHIgM12, polyclonal HIgM control, or LPS for various lengths of time, stained with an antibody against the p65 subunit of NFκB, and subsequently stained with an antibody against the DC marker CD11c. These experiments revealed that NFκB was upregulated between 15 and 30 minutes after addition of sHIgM12. The polyclonal HIgM control had no effect on NFκB levels. The effect of sHIgM12 was specific and was not due to LPS contamination, as DC from Toll-4 deficient mice did not respond to LPS treatment but did upregulate NFκB after treatment with sHIgM12. The sHIgM12 antibody therefore may bind to DC and induce intracellular signals that block programmed cell death, thus enhancing the ability of the cells to induce T cell responses against specific antigens.

To further examine whether binding of sHIgM12 to B7-CD has a direct effect on DC biology and viability, bone marrow-derived DC from mice transgenic for green fluorescent protein (GFP) were treated in vitro prior to adoptive transfer into syngeneic, non-057BL/6 transgenic mice. Five-fold more GFP CD11c$^+$ DC were recovered from draining popliteal and inguinal lymph nodes in mice receiving sHIgM12-treated DC than those receiving cells treated with polyclonal HIgM control. The capacity of lymph node immigrants to potentiate an immune response was tested by concomitant treatment of the DC with sHIgM12 and Ser-Ile-Ile-Asn-Phe-Glu-Lys-Leu (SEQ ID NO:1) peptide prior to adoptive transfer. In vitro treatment of DC with anti-B7-DC antibody not only increased the number of DC recovered by draining lymph nodes, but also increased by 10-fold the ability of these lymph node DC to induce an antigen-specific T cell response.

The ability of sHIgM12 to modulate DC function in a distant tissue was tested by mixing the antibody with untreated DC at the time of transplantation. This experiment was designed to determine whether DC migration and survival could be enhanced provided that the antibody reaches the transplantation site. Treatment with the sHIgM12 antibody resulted in enhanced DC migration to draining lymph nodes, while the polyclonal HIgM control did not result in enhanced migration. In related experiments, mice received i.v. doses of sHIgM12 or polyclonal HIgM on the day before, the day of, and the day after DC transplant. Again, the migration of DC was increased in the mice that received sHIgM12, while the control did not have such an effect. Systemic administration of the antibody therefore is sufficient to influence DC biology.

IL-12 is a key factor in promoting Th1-type cellular immunity. Production of IL-12 by DC treated with sHIgM12 was measured by an ELISA using culture supernatants. Treatment with sHIgM12 stimulated nearly 3-fold higher levels of IL-12 p70 release by DC than did LPS, a strong danger signal. The polyclonal HIgM control did not elicit detectable levels of IL-12 p70. The increased secretion of IL-12 supports the observation that modulation of B7-DC by sHIgM12 strongly potentiates a cellular immune response against even weakly immunogenic tumors.

Example 7 sHIgM12 Binds to Human DC

To examine whether sHIgM12 also binds the human B7-DC orthologue, human monocyte-derived DC were stained with sHIgM12 or polyclonal IgM control antibody. sHIgM12 bound weakly to immature DC. Maturation of the cells with LPS increased the level of sHIgM12 binding, particularly on CD83$^+$ cells. DC activated with different stimulation protocols displayed sHIgM12 binding that was increased to varying degrees: cells activated with LPS were bound by sHIgM12 to a high degree, cells activated with TNF-α and IL-1β were bound by sHIgM12 to an intermediate degree, and cells activated with IFN-γ were bound by sHIgM12 to a lesser degree.

To determine whether human B7-DC is a ligand for sHIgM12, Ltk fibroblast cells were transiently transfected with a human B7-DC expression plasmid and cultured for 48 hours. sHIgM12 bound to the B7-DC transfected cells to a significantly higher level than to mock-transfected cells. Furthermore, the level of sHIgM12 binding to L-cells was positively correlated with the amount of B7-DC plasmid used in the transfection.

B7-DC is expressed in a variety of human and murine tumors. To examine whether sHIgM12 binds to tumor cells, human TP365 glioma cells were incubated with the antibody. These cells were stained by sHIgM12 at a level that was significantly higher than the staining by polyclonal IgM control antibody. Furthermore, PCR was used to generate a B7-DC amplicon with DNA from TP365 cells. The sHIgM12 antibody thus may bind to glioma cells via B7-DC.

Example 8

Effects of sHIgM12 on Immune Response to Protein Antigen

Figure 7:
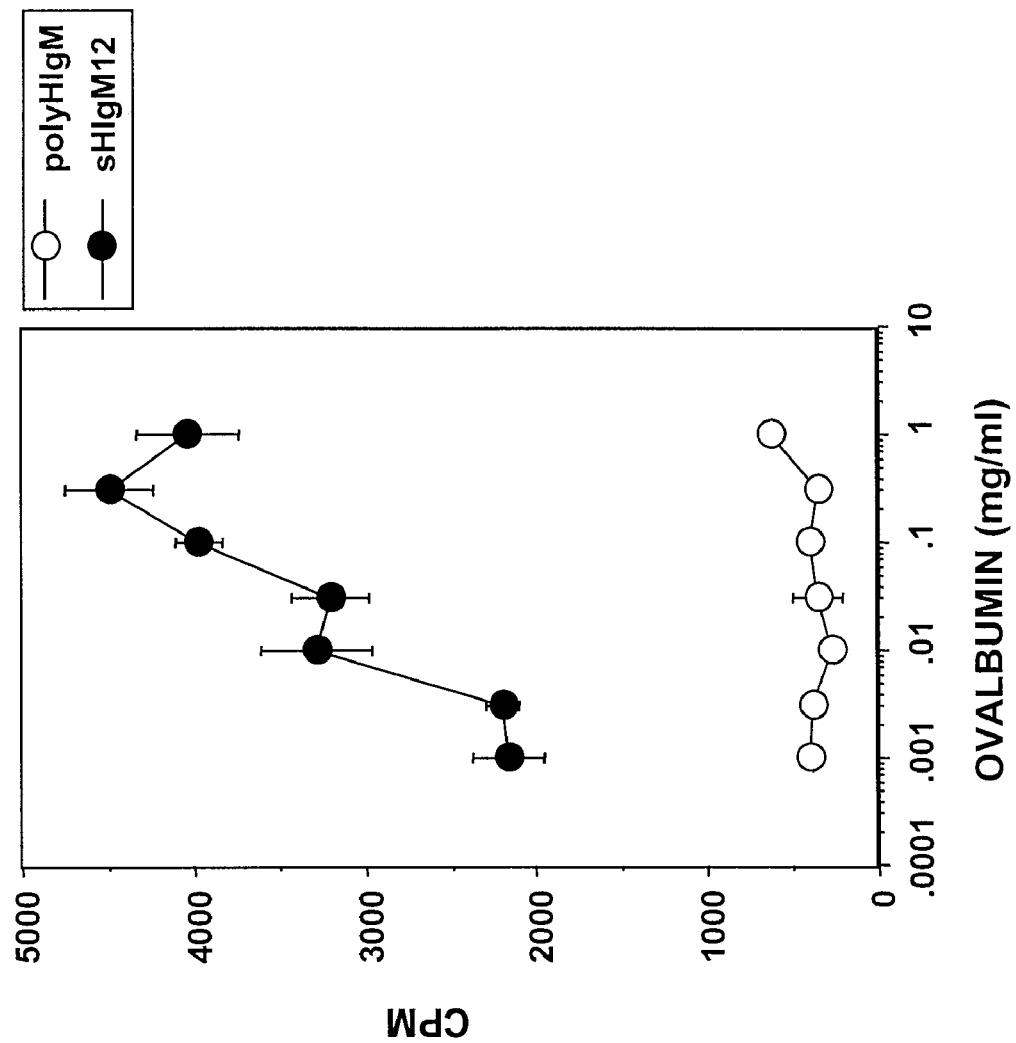
FIG. 7 is a graph showing the immune response of splenocytes isolated from mice that were pre-treated with sHIgM12 (filled circles) or polyclonal HIgM control (open circles) and immunized with OVA. After isolation, the splenocytes were restimulated in vitro with OVA.

The systemic effect of sHIgM12 binding to DC was examined in vivo. Mice were treated with 10 μg sHIgM12 antibody or polyclonal HIgM control on days −1, 0, and +1, and immunized with 1 mg of OVA on day 0, Seven days after immunization, splenocytes were isolated and assayed for a proliferative response against OVA antigens. Splenocytes treated with polyclonal HIgM control did not mount an immune response against OVA. Treatment with sHIgM12, however, led to high levels of proliferation in response to titrated amounts of antigen (FIG. 7). These data indicate that systemic sHIgM12 has profound immune potentiating effects, presumably through its interaction with DC.

Since sHIgM12 significantly enhanced T cell activation at the time of adoptive transfer into immunocompetent mice (Example 3), it is possible that sHIgM12 treatment could enhance the protective effect of adoptively transferred DC primed with antigenic tumor-derived peptides. To test this possibility, syngeneic DC pulsed with the B16-derived antigenic peptide Trp2$_{180-188}$ are adoptively transferred into C57BL/6 mice on the earliest day after tumor inoculation on which antibody treatment alone does not protect the mice. Groups of C57BL/6 mice receive DC pulsed with either tumor specific antigenic peptide or an irrelevant peptide along with sHIgM12 or polyclonal HIgM control. Alternatively, a B16 melanoma variant that expresses chicken OVA is used as an antigen. T cells from OT-1 TcR transgenic mice are adoptively transferred into mice bearing established tumors at various stages (e.g., days +3, +5, +7, +9, and +11) after tumor challenge. The activation, tumor infiltration, and anti-tumor cytotoxicity of T cells bearing the OT-1 receptor are monitored as animals are treated with sHIgM12 or polyclonal HIgM control. OT-1 cells specific for the surrogate tumor antigen are visualized and isolated using T cell-specific class I tetramers such as those generated in response to the antigenic Ser-Ile-Ile-Asn-Phe-Glu-Lys-Leu (SEQ ID NO:1) OVA peptide.

Example 9

Materials and Methods for In Vivo Studies of the Immunotherapeutic Potential of sHIgM12 in Conferring Anti-Tumor Activity Mice: Wild type C57BL/6J, B6.129S2-Cd4$^{tm1Mak}$/J (CD4$^{-/-}$), B6.12952Cd8$^{tm1/Mak}$/J (CD8$^{-/-}$), B6.129S7-Rag$^{tm1/Mom}$/J (Rag1$^{-/-}$), and B6.129S2-Gzmb$^{tm1Ley}$/J (granzyme B$^{-/-}$) strains of mice, all on the C57BL genetic background, were purchased from The Jackson Laboratory. B6.129P2-B2m$^{tm1/Umc}$/J (β2-microglobulin$^{-/-}$) mice were bred in the immunogenetic mouse colony (Chella David) at the Mayo Clinic, Rochester, Minn. B cell deficient μMT mice were obtained from Marilia Cascalho at the Mayo Clinic. C57BL/6-Prf1$^{tm1Sdz}$/J (perforin$^{-/-}$) mice were originally obtained from The Jackson Laboratory and were subsequently bred in the mouse colony of Moses Rodriguez at the Mayo Clinic.

Reagents: The B7-DC cross-linking antibody, sHIgM12, was purified as described herein. A preparation of pHIgM and an IgM antibody (sHIgM39) purified from the serum of a patient with chronic lymphoproliferative disorder were used as isotype control antibodies. Bouin's fixative was obtained from Sigma-Aldrich (St. Louis, Mo.). B16, B16-F10, and EL-4 lines of tumors were maintained in RPMI (Cambrex Bioscience, Walkersville, Md.) containing 10% calf serum (GIBCO Invitrogen, Grand Island, N.J.). PE antibody coupled to the pan-NK cell marker, DX-5, was obtained from PharMingen (San Diego, Calif.). NK1.1 (PK136) was obtained from Lieping Chen at the Mayo Clinic. LPS and Poly I:C were purchased from Calbiochem. CpG (5'-TCCAT-GACGTTCCTGACGTT-3', SEQ ID NO:3) was synthesized in the Mayo Clinic molecular biology core facility.

Prophylactic regimen: Mice were injected with 2×10$^4$ B16 cells on the right flank in a 100 μl volume. Animals were injected at a distal site with 10 μg of sHIgM12 or the control antibody in 100 μl in PBS on the day before, the day of, and the day after tumor challenge. Mice were monitored for tumor development, and were euthanized when the tumor size reached 225 mm$^2$ in size. The size of the tumors was determined in two dimensions using calipers (Dyer, Lancaster, Pa.). Mice that failed to develop tumors for 30 days were rechallenged with 2×10$^4$ B16 cells on the left flank. Rechallenged mice were monitored for another 30 days. Separate sets of mice that resisted B16 melanoma grafts were challenged with 2×10$^6$ EL-4 cells on the opposite flank and were monitored for tumor growth. Naïve mice injected with 2×10$^6$ EL-4 cells served as controls for this test of specificity of tumor resistance.

Therapeutic regimen: Mice were intravenously injected with 5×10$^5$ B16-F10 cells. Mice were treated with 10 μg of sHIgM12 or the control antibody on days 3, 4, and 5. Sentinel mice were injected with the tumor cells and received no further treatments. Tumor load in sentinel animals was monitored by examining the lungs of individual animals on a periodic basis using a dissection microscope to ascertain when a significant tumor load was present in the treatment groups. When a sentinel was detected that had developed 50 or more tumor nodules in their lungs, the animals in the experimental treatment groups were euthanized and tumor nodules in their lungs were counted. For depletion experiments, 200 µg of NK1.1 mAb was injected intraperitoneally 72 hours and 48 hours prior to tumor injection and every 3-4 days thereafter for the duration of the experiment. Depletion of the appropriate cell subset was confirmed by flow cytometry using anti-NK1.1 and anti-DX-5 antibody. The sentinel mice typically developed nodules in the lungs by days 17 to 21. Mice from all the experimental groups were then euthanized, the lungs were fixed with Bouin's fixative, and the number of nodules was determined using a dissection microscope.

Flow Cytometry: Sera were collected from mice that had been engrafted with B16 melanoma on the flank and treated using the prophylactic regimen with either control polyclonal IgM antibody or sHIgM12 antibody. Dilutions of the sera were assayed for the presence of anti-tumor antibodies using standard flow cytometry to assess binding to B16 melanoma cells. DC derived from bone marrow precursors in vitro or isolated directly from the spleens of animals (see, e.g., Radhakrishnan et al. (2003) *J. Immunol.* 170:1830-1838) were analyzed by multicolor flow cytometry for incorporation of FITC and staining with anti-B7.1- or B7.2-PE, and anti-CD11c-APC.

Cytotoxicity Assay Briefly, $5 \times 10^5$ B16 melanoma cells were injected in the right flank of C57BL/6 mice. Mice were injected intravenously with either 10 µg of control antibody or B7-DC cross-linking antibody on the day before, the day of, and the day after tumor injection. Seven days later, cells from the draining lymph nodes from five mice per group were harvested, pooled and further stimulated with $2 \times 10^6$ cells/ml of mitomycin C- (Calbiochem) treated B16 melanoma cells for an additional 4 days. The effector cells were harvested and titrated in triplicate against $^{51}$Cr (Amersham) labeled B16 or EL4 cells in a standard 4 hour cytotoxicity assay.

Statistical analysis: Statistical analysis was performed on normally distributed data using ANOVA for multiple comparisons, or the Student's t-test for comparisons of two groups. For data that was not distributed normally, the Whitney-Rank sum test was used for the analysis of two treatment groups and a rank ANOVA for comparing more than two treatment groups.

Example 10

Systemic Treatment with sHIgM12 Induces Resistance to B16 Melanoma

B16 melanoma is an aggressive tumor derived from C57BL mice that kills immunocompetent animals receiving a subcutaneous inoculum of as few as $2 \times 10^4$ cells. In this model, palpable tumors develop 10-12 days following tumor transplantation, and tumors typically progress to surface areas in excess of 225 mm$^2$ by day 17. In these experiments, mice were intravenously injected at a distant site with isotype control polyclonal IgM antibody (pHIgM), PBS, or sHIgM12 on days -1, 0, and +1 relative to tumor transplant. At day 17, only a single mouse among thirteen mice (7%) treated with pHIgM and no mice among 13 PBS treated animals was tumor free. In contrast, 11 of 16 mice (69%) injected with sHIgM12 remained tumor free at day 17 (p<0.001, Table 1). For mice that did develop palpable tumors, sHIgM12 treatment significantly inhibited tumor growth as compared to growth of tumors in mice treated with PBS or pHIgM (p<0.001, Table 1). The delay in growth was transient, as tumors that did develop in sHIgM12-treated mice eventually progressed to 225 mm$^2$ in size. In a separate experiment, mice treated with sHIgM12 antibody on days 9, 8, and 7 prior to challenge with B16 melanoma displayed no treatment effects on tumor growth; 100% of the animals treated with B7-DC cross-linking antibody (n=8) or isotype control antibody (n=8) developed tumor with the same kinetics. This finding indicates that the timing of treatment relative to tumor engraftment is an important factor in determining treatment outcome.

TABLE 1 sHIgM12 treatment protects mice from subcutaneous challenge with B16 melanoma

| Treatment | Tumor-Free (Day 17) | Statistic | Average Tumor Size (mm$^2$) | SEM (mm$^2$) | Statistic |
|---|---|---|---|---|---|
| pHIgM | 1/13 | Reference | 167.0 | +/−21.2 | Reference |
| PBS | 0/13 | NS* | 182.1 | +/−21.3 | NS |
| sHIgM12 | 11/16 | P < 0.001 | 13.2 | +/−7.5 | P < 0.001 |

*NS = no statistical difference

Example 11

Resistance to B16 Melanoma by sHIgM12 Treatment is Immune Mediated

Flow cytometry was used to evaluate whether sHIgM12 binds directly to tumor cells. No binding was observed, suggesting that the antibody may be acting indirectly on the tumor cells by binding to cells derived from the host. sHIgM12 antibody bound to DC derived from bone marrow precursors in vitro, however, suggesting that the induced resistance to lethal tumor challenge may be mediated by sHIgM12 interaction with endogenous DC. Modulation of DC function could promote changes in the immune response, and could be the underlying mechanism determining antibody induced tumor resistance. This possibility was explored using two approaches. First, studies were conducted to evaluate whether sHIgM12 antibody administered systemically to mice could modulate the phenotype of endogenous DC. Second, studies were conducted to determine whether in vivo administration of sHIgM12 induced tumor resistance by potentiating an anti-tumor response.

Using DC generated in vitro from bone marrow precursors, it was shown that treatment with sHIgM12 B7-DC cross-linking antibody potentiates the ability of these cells to activate naïve antigen-specific T cells, but does not induce traditional maturation markers in the DC. As DC mature, they lose the ability to acquire antigen from their surroundings and increase their expression of the co-stimulatory molecules B7.1 (CD80) and B7.2 (CD86) at the cell surface (Banchereau and Steinman (1998) *Nature* 392:245-252). B7.1 and B7.2 expression levels were not substantially increased following treatment of bone marrow derived myeloid DC with sHIgM12 antibody in vitro (Radhakrishnan et al., supra). To evaluate functional changes associated with activation following sHIgM12 treatment, changes in pinocytotic activity were assessed by monitoring the ability of DC to take up FITC-tagged bovine serum albumin (BSA) in vitro.

As shown in Table 2A, DC treated with the TLR-4 agonist LPS accumulated lower amounts of FITC-BSA as compared to the levels acquired by DC treated with pHIgM control antibody. Since engagement of TLR-4 induces maturation of DC, this was an expected result. In contrast, DC treated with the B7-DC cross-linking antibody sHIgM12 accumulated significantly more FITC-BSA than did DC treated with isotype control antibody or isotype control antibodies, demonstrating that treatment with sHIgM12 antibody does not induce maturation of DC in vivo. DC from mice treated with the TLR agonists, on the other hand, expressed significantly higher levels of both co-stimulatory molecules, demonstrating that DC maturation is induced by engaging TLR-3 and TLR-9.

TABLE 2

Antigen acquisition and expression of co-stimulatory molecules following DC activation

| Source of DC | Treatment | FITC-MFI (+/−SEM) | B7.1 MFI (+/−SEM) | B7.2 MFI (+/−SEM) |
|---|---|---|---|---|
| A. IN VITRO | | | | |
| Bone marrow GM-CSF/IL-4 | Polyclonal human IgM; 10 μg/ml FITC-BSA | 141.5 (+/−0.5) $p < 0.001$ | ND* | ND |
| Bone marrow GM-CSF/IL-4 | sHIgM12; 10 μg/ml FITC-BSA | 583.5 (+/−6.5) $p < 0.001$ | ND | ND |
| Bone marrow GM-CSF/IL-4 | LPS; 10 μg/ml FITC-BSA | 10.0 (+/−1.0) $p < 0.001$ | ND | ND |
| B. IN VIVO | | | | |
| Spleen Endogenous DC | sHIgM39 isotype control; 100 μg FITC-OVA i.p. | 56.0 (+/−10.7) $p < 0.001$ | 52.01 (+/−3.2) NS** | 194.7 (+/−2.4) NS |
| Spleen Endogenous DC | sHIgM12; 100 μg FITC-OVA i.p. | 116.0 (+/−7.0) $p = 0.001$ | 53.0 (+/−4.2) NS | 200.0 (+/−8.5) NS |
| Spleen Endogenous DC | Poly I:C/CpG-ODN; 100 μg FITC-OVA i.p. | 24.7 (+/−2.7) $p = 0.026$ | 70.7 (+/−2.6) $p = 0.013$ | 319.3 (+/−3.8) $p < 0.001$ |

*ND = not determined
**NS = no statistical difference type control antibody. This finding provided additional evidence that activation of DC with B7-DC cross-linking antibody does not induce a traditionally defined maturation response, but rather induces a distinctive activation phenotype.

The ability of endogenous DC to pinocytose was evaluated to determine whether systemic treatment with B7-DC cross-linking antibody targets DC in vivo, as well. C57BL/6 mice were treated intravenously on two successive days with either isotype control IgM antibody sHIgM39, the B7-DC cross-linking antibody sHIgM12, or a combination of the TLR-3 and TLR-9 agonists poly I:C and CpG oligonucleotide. LPS was not used in the in vivo analysis to avoid toxicity. At the time of the second treatment, the animals received 100 ug of FITC-OVA intraperitoneally. Twenty hours later, splenic DC were isolated and analyzed by flow cytometry for accumulation of FITC-OVA and expression levels of the co-stimulatory molecules B7.1 and B7.2. DC were identified by their expression of the surface marker CD11c. As shown in Table 2B, DC isolated from animals treated with sHIgM12 acquired significantly higher levels of FITC-OVA relative to DC from animals treated with the isotype control antibody. This result mirrored the analysis of pinocytotic activity of bone marrow derived DC in vitro. Furthermore, DC isolated from animals treated with the TLR agonists accumulated significantly lower levels of FITC-OVA, a finding consistent with the decrease in antigen acquisition by mature DC. The maturation status of these endogenous DC in this analysis is illustrated by the levels of expression of the B7.1 and B7.2 co-stimulatory molecules in the different treatment groups. There was no significant difference in expression levels of co-stimulatory molecules on DC isolated from animals Dendritic cell uptake of antigen is a critical step in the initiation of antigen-specific T cell responses. The effect of sHIgM12 on the ability of DC to take up antigen was studied using FITC labeled chicken albumin as a model antigen. Eight week old mice received intradermal injections of 100 μg FITC-OVA. After 24 hours, the amount of FITC contained within CD11c dendritic cells was assessed by flow cytometry. The animals received a variety of treatments to influence antigen uptake by DC in draining lymph nodes. As shown in FIG. 8A, no label was incorporated in DC of mice that received i.v. injections of 10 μg sHIgM39 one day prior to and on the same day as intradermal challenge with FITC-OVA. This control IgM human antibody has no apparent binding on mouse dendritic cells. In contrast, DC isolated from animals that received the isotype matched sHIgM12 antibody incorporated substantial FITC label, indicating that they took up the FITC-OVA antigen (FIG. 8B). Pretreatment of DC with the TY-25 anti-B7-DC antibody inhibited the activation of the transcription factor NF-κB in DC that is usually induced following incubation with sHIgM12. As shown in FIG. 8C, administration of TY-25 also inhibited the acquisition of soluble antigen induced by sHIgM12. As shown in FIG. 8D, sHIgM12 treatment had no effect on antigen uptake by dendritic cells in the draining lymph nodes of B7-DC deficient animals, although DC from B7-DC deficient animals were able to take up antigen following i.v. injection of an IgG antibody specific for CD40 one day prior to and on the day of intradermal challenge with 100 μg of FITC-OVA (FIG. 8E). The level of antigen uptake induced by CD40-specific antibody treatment of B7-DC$^{-/-}$ mice was comparable to the levels of uptake observed in normal animals in response to the same treatment (FIG. 8F).

To determine whether treatment of mice with sHIgM12 induces tumor resistance by potentiating an immune response, the ability of antibody to induce tumor resistance in immunodeficient B6-RAG1$^{-/-}$ mice, which lack B and T cells, was evaluated. Treatment of these animals with sHIgM12 using the prophylactic treatment protocol had no effect on B16 melanoma appearance or growth, demonstrating that an intact immune system is essential for the induction of tumor resistance (Table 3A). The failure of sHIgM12 antibody treatment to protect Rag-deficient mice also provided additional evidence that the antibody does not act directly on the tumor. The importance of the CD8 T-cells in the host immune response to the tumors was established using $\beta_2$-microglobulin mice. Although these knockout mice have an intact CD4 T-cell repertoire, the deficiency in CD8 T-cells abolished the protective effect of sHIgM12 antibody treatment (Table 3B). Likewise, the absence of a helper response in CD4 knockout mice abrogated the protective effect of sHIgM12, as all of these mice developed palpable tumors akin to mice receiving control treatment (Table 3C).

more, the finding that B cell deficient mice are protected from B16 melanoma following treatment with the human antibody sHIgM12 excludes the possibility that an anti-human IgM antibody response by antibody treated animals is an integral component of the treatment effect elicited with B7-DC cross-linking antibody.

The hallmark of an effective adaptive immune response is a vigorous memory response upon secondary challenge. To study whether a memory response against B16 tumor antigens was established following treatment with sHIgM12 antibody, the surviving mice were re-challenged with a lethal dose of B16 melanoma cells in the opposite flank. As shown in Table 4, mice that had survived for at least 30 days following initial tumor challenge displayed significant resistance to a secondary challenge with tumor cells (p<0.001). As none of the surviving mice received additional treatments with sHIgM12, the resistance to secondary challenge indicates that an effective anti-tumor immune response was established in mice treated with sHIgM12 following the initial challenge.

TABLE 3

B7-DC cross-linking antibody is not protective in immuno-compromised host

| Group | Treatment | Tumor-Free (Day 11) | Statistic | Average Tumor Size (mm$^2$) | SEM (mm$^2$) | Statistic |
|---|---|---|---|---|---|---|
| A. C57BL/6J-RAG$^{-/-}$ | pHIgM | 0/5 | Reference | 150.0 | +/−22.2 | Reference |
| | sHIgM12 | 0/5 | NS* | 192.6 | +/−15.8 | NS |
| B. C57BL/6J-$\beta_2$-m | pHIgM | 0/6 | Reference | 136.5 | +/−29.3 | Reference |
| | sHIgM12 | 0/6 | NS | 136.0 | +/−24.5 | NS |
| C. C57BL/6J-CD4$^{-/-}$ | pHIgM | 0/9 | Reference | 162.3 | +/−13.0 | Reference |
| | sHIgM12 | 0/9 | NS | 150.0 | +/−14.4 | NS |

*NS = no statistical difference

Figure 9:
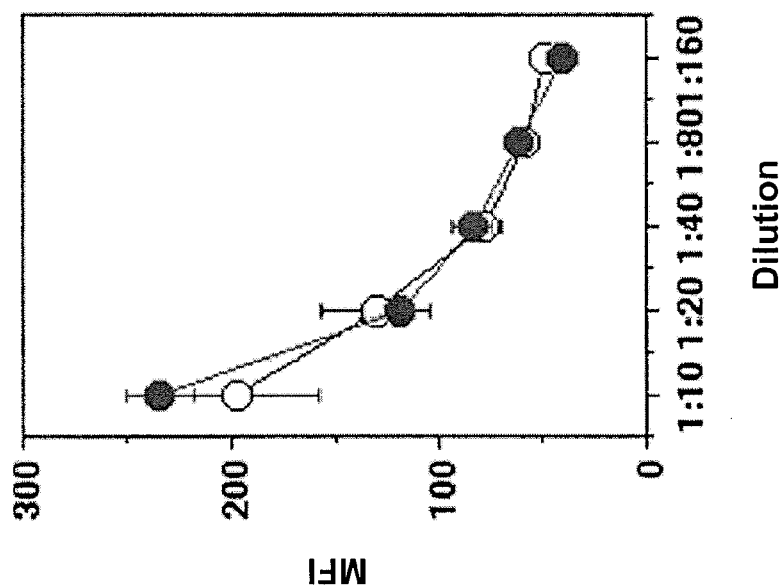
FIG. 9 is a graph showing antibody responses to B16 melanoma in mice treated with polyclonal human IgM control antibody (open circles) or sHIgM12 B7-DC cross-linking antibody (closed circles). Antibodies in serial dilutions of sera from the animals were evaluated by flow cytometry for their ability to bind to B16 melanoma cells. Data is represented as mean fluorescent intensity (MFI). n=5 mice per group.

The B-cell immune response, as measured by serum levels of anti-tumor antibodies, was indistinguishable between C57BL/6 mice receiving sHIgM12 or polyclonal IgM treatment. Serum was collected from mice on day 17, when animals treated with isotype control antibodies had developed tumors approaching 225 mm$^2$ in size. Animals treated with B7-DC cross-linking antibodies were tumor free. Serial dilutions of the sera were assessed for tumor-binding antibodies by flow cytometry. As shown in FIG. 9, levels of tumor reactive antibodies were indistinguishable in animals receiving tumor protective treatment with B7-DC cross-linking antibody or non-protective treatment with polyclonal human IgM antibody.

To further evaluate whether B cell responses contribute to the anti-tumor response induced by B7-DC cross-linking, B cell-deficient uMT animals were treated with B7-DC cross-linking antibodies and challenged with B16 melanoma using the prophylactic treatment model described in Example 8. Wild-type C57BL/6 mice treated with isotype control human IgM antibody developed rapidly growing tumors that reached 225 mm$^2$ by day 17 after tumor engraftment (n=4). In contrast, C57BL/6 (n=5) and B cell deficient uMT (n=5) mice treated with sHIgM12 B7-DC cross-linking antibody were strongly protected; one of five of the C57BL/6 mice eventually developed a tumor, while no tumors developed in the B-cell deficient uMT animals. B16 melanoma grew rapidly in the μMT mouse line following treatment with isotype control antibody, demonstrating histocompatibility of the tumor with the uMT subline. These results demonstrated that an anti-tumor antibody response is not a critical factor distinguishing susceptible from resistant mice in this tumor model. Further- In contrast, animals that resisted B16 melanoma following sHIgM12 antibody treatment showed no increased resistance to the unrelated tumor, EL-4.

Figure 10:
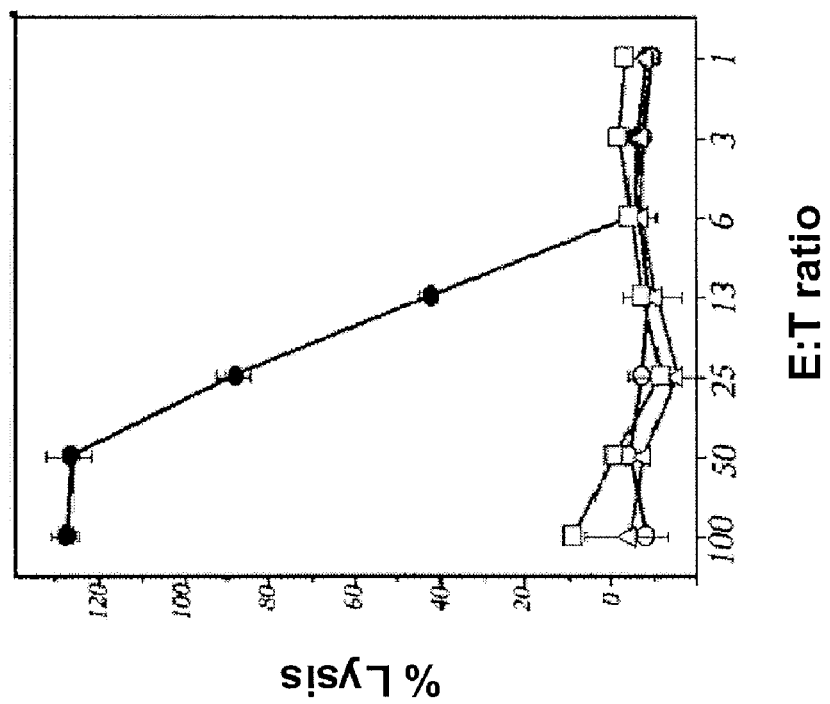
FIG. 10 is a graph showing levels of tumor specific cytotoxic T lymphocyte (CTL) induction in B16 tumor-bearing mice treated with sHIgM12 or with pHIgM control. Filled circles represent the average response of effector cells from sHIgM12 treated mice against B16 melanoma cells, while open circles represent the responses of effector cells from pHIgM treated mice. Open triangles and open squares represent the responses of effector cells from pHIgM treated mice or sHIgM12 treated mice, respectively, against EL-4 target cells.

To determine whether treatment with B7-DC cross-linking antibody potentiates tumor-specific CTL, the draining lymph nodes of mice bearing 7 day tumors were assayed for tumor-specific CTL precursors. The animals were treated with sHIgM12 antibody or control antibody one day prior to, the same day as, and one day after tumor challenge. Harvested lymph node cells were cultured in the presence of mitomycin-treated B16 melanoma cells for an additional four days and then assessed for tumor specific cytotoxic activity in a standard $^{51}$Cr release assay. Cytotoxic activity against B16 target cells was only observed in cultures of cells derived from animals treated with B7-DC cross-linking antibody (FIG. 10). Killing was specific for the B16 melanoma targets, as EL-4 tumor cells were not killed. Lymph node cells from B16 challenged mice treated with control antibody displayed no activity, a finding consistent with the

TABLE 4

B7-DC cross-linking antibody induces a recall response.

| Treatment | Tumor-Free (Day 17) | Statistic | Average Tumor Size (mm$^2$) | SEM (mm$^2$) | Statistic |
|---|---|---|---|---|---|
| Naïve, pHIgM | 0/5 | Reference | 206.0 | +/−25.2 | Reference |
| Naïve, sHIgM12 | 4/5 | P = 0.048 | 13.6 | +/−13.6 | P < 0.001 |

TABLE 4-continued

B7-DC cross-linking antibody induces a recall response.

| Treatment | Tumor-Free (Day 17) | Statistic | Average Tumor Size (mm²) | SEM (mm²) | Statistic |
|---|---|---|---|---|---|
| Tumor survivors (sHIgM12) | 6/9 | P = 0.031 | 35.6 | +/−20.2 | P < 0.001 |
| Naïve, EL-4 challenge | 0/4* | Reference | 171.5 | +/−17.7 | Reference |
| B16 survivor, EL-4 challenge | 0/4* | NS** | 158.5 | +/−20.1 | NS |

*Animals were evaluated for growth of EL-4 tumors on their flanks on day 13
**NS = no statistical difference known weak innate antigenicity of B16 melanoma tumor line. Taken together, these findings demonstrate that systemic treatment with the B7-DC cross-linking antibody sHIgM12 potentiates a cellular immune response against B16 melanoma, causing acute tumor rejection and long-term immunity.

Example 12

Treatment with sHIgM12 Protects Mice in a B16 Lung Metastasis Model

The F 10-B16 subline of B16 melanoma was selected for its efficient ability to metastasize to the lungs. This particular tumor line is highly virulent, weakly antigenic, and is characterized by depressed MHC class I gene expression. Intravenous introduction of F10-B16 melanoma as a cell suspension typically results in 50 to 200 tumor nodules in the lungs of within three to four weeks. To evaluate the effectiveness of sHIgM12 treatment on the induction of tumor resistance in this model, animals were seeded with lung metastases three days prior to antibody treatment. Animals received 10 μg of sHIgM12 B7-DC cross-linking antibody intravenously on days 3, 4, and 5 post tumor challenge. Untreated sentinel mice that received identical tumor challenges were monitored for tumor burden. When tumor burdens exceeded 50 nodules in the sentinel mice, the experiments were terminated and the lungs of animals from all treatment groups were analyzed for the presence of tumor.

Figure 11:
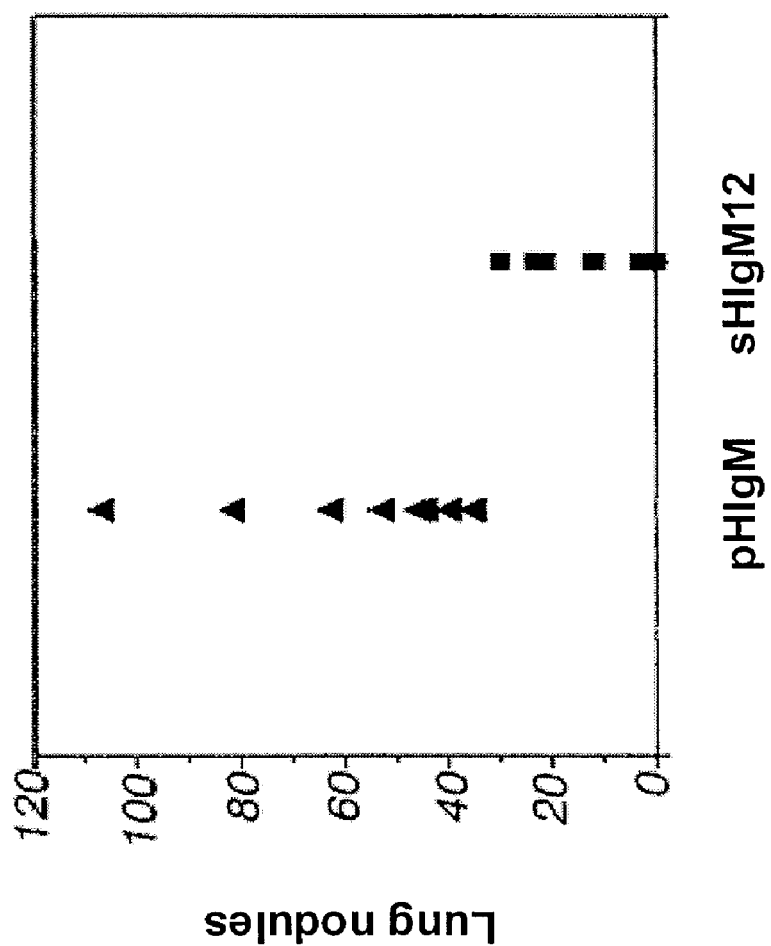
FIG. 11 is a graph showing the number of tumor nodules in the lungs of mice injected with a B16-F10 cell suspension and then treated with pHIgM control or sHIgM12. p<0.001. n=8 per treatment group.

As shown in FIG. 11, the lungs of animals receiving sHIgM12 antibody contained significantly fewer tumor nodules than mice receiving control pHIgM. In the experiment shown, all eight animals treated with sHIgM12 antibody developed fewer tumor nodules than the least number observed in the eight animals treated with control isotype matched antibody (p<0.001), and three of the eight protected animals developed no tumor. Overall, approximately half the animals (14 of 29) treated with sHIgM12 remained free of tumor. Thus, systemic administration of B7-DC cross-linking antibody confers resistance to a highly lethal, weakly immunogenic tumor even after the tumor is allowed to establish for three days prior to initiating treatment.

Example 13

Induced Resistance to F10-B16 Melanoma is Mediated by CD8+ T Cells

Figure 12:
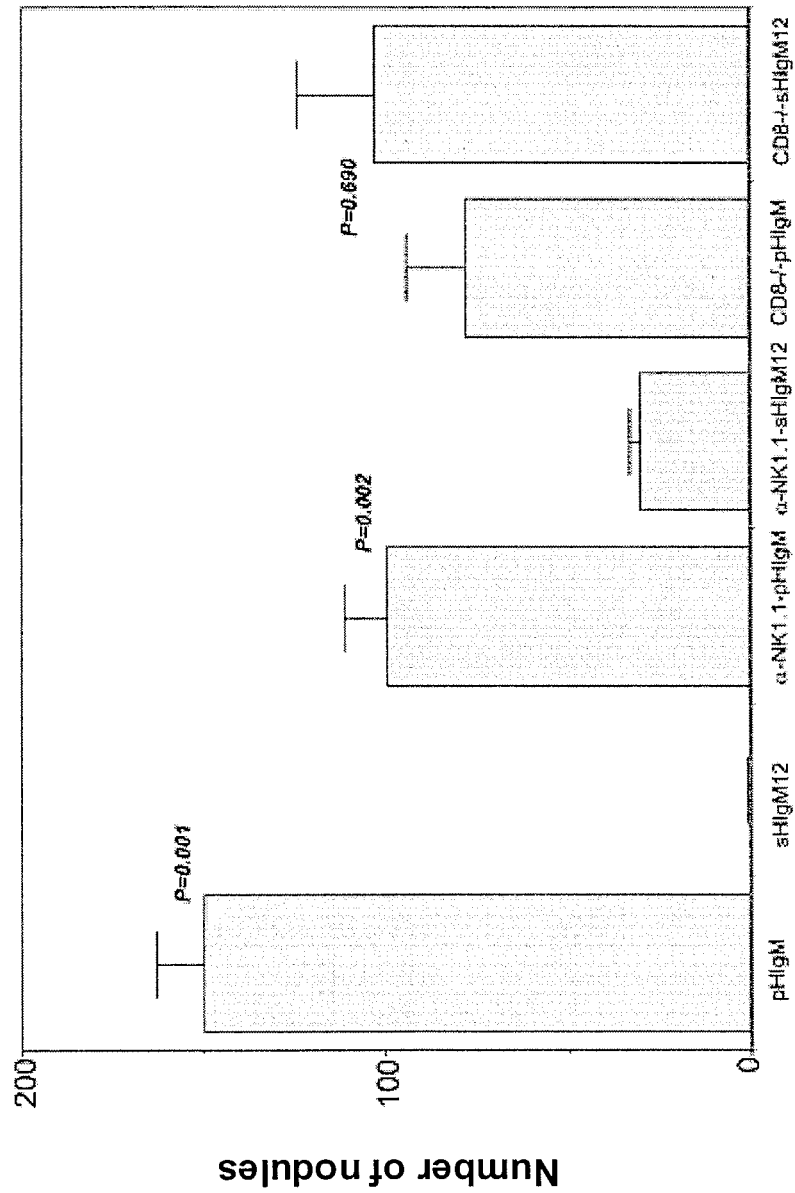
FIG. 12 is a graph showing the number of lung nodules in wild type or CD8 deficient mice that were injected with B16-F10 cells and treated with sHIgM12 or pHIgM control antibody, with or without treatment with an NK cell depleting antibody prior to injection of B16-F10 cells. Data represent the number of nodules from 5 to 7 mice in each group. Data were analyzed using rank-sum methods, and pair-wise comparisons are shown. In addition, p<0.001 for animals receiving sHIgM12 vs. those receiving sHIgM12 and the NK1.1 NK depleting antibody.

Since F10-B16 tumors express reduced amounts of MHC class 1 molecules, the possibility that resistance induced by treatment with sHIgM12 might be mediated by NK cells was evaluated. Animals were treated with anti-NK1.1 antibody prior to tumor challenge. The efficiency of the NK cell depletion protocol was monitored by flow cytometry using NK1.1- and DX-5-specific antibodies to visualize NK cells. Splenic NK cells were reduced by greater than 90% in animals treated with NK1.1 specific antiserum. As shown in FIG. 12, direct comparison of sHIgM12-treated, NK cell depleted animals with sHIgM12-treated mice suggests a minor, but statistically significant (p<0.001) contribution of NK cells in the anti-tumor response induced by systemic sHIgM12 treatment. However, NK cell depleted mice were still responsive to the immunotherapeutic effects of B7-DC cross-linking antibody administered three days after i.v. challenge with F10-B16 melanoma (p=0.002). In contrast, CD8-knockout mice were not responsive to treatment with B7-DC cross-linking antibody, indicating that CD8+ T cells are critical mediators of anti-tumor immunity in this model. NK-deficient or CD8-deficient mice that did not receive B7-DC cross-linking antibodies were no more susceptible or resistant to developing lung tumors than were untreated animals, consistent with the characteristically weak immunogenicity of the F10-B16 tumor line.

Figure 13:
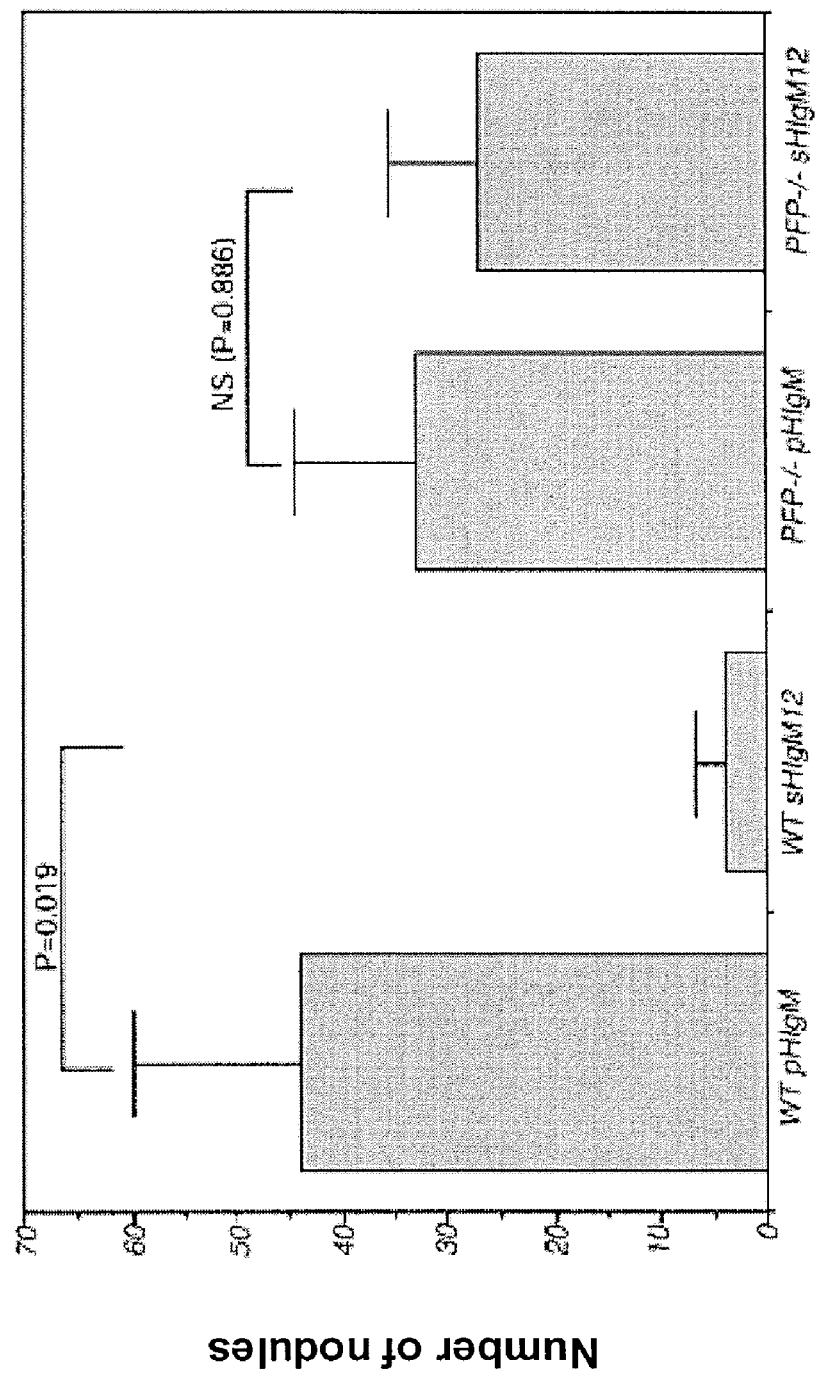
FIG. 13 is a graph showing the mean number of lung nodules in wild type mice or perforin deficient mice that were injected with B16-F10 cells and treated with sHIgM12 or pHIgM control antibody. Data represent the mean number of nodules in the lungs of 4 mice in the wild type (WT) or perforin-dependent ($PFP^{-/-}$), control antibody treated (pHIgM) or B7-DC cross-linking antibody treated (sHIgM12) groups. N=4 in all groups except for the wild type, sHIgM12 treated group, where n=6.

The ability of cytotoxic lymphocytes to kill tumor cells is mediated, in part, by perforin- and granzyme-dependent pathways (Van den Broek et al. (1996) J. Exp. Med. 184:1781-1790; and Pardo et al. (2002) Eur. J. Immunol. 32:2881-2887), although in some circumstances both mediators of cytotoxicity are not required (Smyth et al. (2003) J. Immunol. 171:515-518). Experiments were conducted to evaluate whether the protective effects induced by systemic antibody treatment are perforin mediated. Perforin knockout mice were treated with sHIgM12 on days 3, 4, and 5 post tumor challenge as described above, and lungs were analyzed for growth of tumor nodules. As shown in FIG. 13, sHIgM12 immunotherapy was ineffective in perforin deficient animals, while highly effective in wild type B6 mice. In an independent experiment, B7-DC cross-linking with sHIgM12 antibody also was not protective in granzyme B-deficient mice. Using the therapeutic treatment model, an average of 98.2 (+/−4.9 SEM, n=5) tumor nodules were found in the lungs of granzyme B-deficient mice treated with control polyclonal human IgM antibody, as compared to 99.2 (+/−15.0, n=5) tumor nodules in the lungs of granzyme B-deficient mice treated with sHIgM12 B7-DC cross-linking antibody. Since NK cells do not appear to be the primary mediators of the anti-tumor resistance induced by treatment with B7-DC cross-linking antibody, and since the protective response is dependent on CD8 T cells, these findings are most consistent with the view that treatment of tumor bearing mice with B7-DC cross-linking antibody potentiates cytolytic CD8+ T cells in vivo, and that cytotoxicity is mediated by both perforin and granzyme B.

Example 14

Production of Recombinant Human IgM Antibodies

Figure 14:
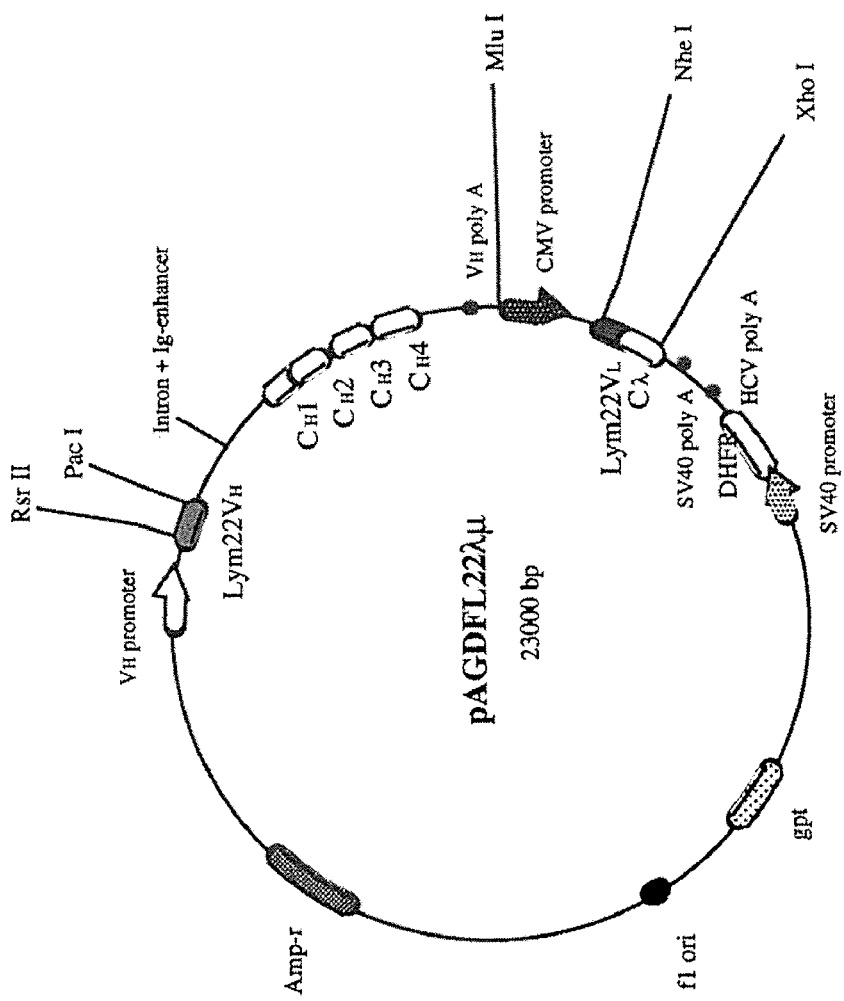
FIG. 14 is a map of an expression vector that can be used to produce antibodies.

Once antibodies of interest such as sHIgM12 are identified, immortalized sources are generated to sustain these important reagents. A vector system was developed and used to immortalize sHIgM12 as well as another human IgM antibody (sHIgM22) identified in the serum of a Waldenstrom's macroglobulinemia patient. The amino acid sequence of the antibodies were determined from Fv fragments generated from the serum. Since malignant B cells circulate in the blood of Waldenstrom patients, cDNA encoding the heavy and light chain genes of the sHIgM22 antibody present in highest serum concentrations was successfully isolated. These cDNA sequences were used to generate a genomic human IgM heavy chain gene encoding the variable region derived from the patient antibody and a cDNA-based light chain gene expressed under control of the cytomegalovirus (CMV) promoter. These antibody gene sequences were incorporated into a single vector (FIG. 14) along with a selectable dHfR gene expressed under the control of a SV40 promoter. The vector bearing the synthetic antibody genes was introduced into F3B6 hybridoma cells by electroporation. Methotrexate resistant cells were selected and amplified by stepping up the amount of methotrexate in the culture medium. A clone expressing 100 μg antibody per ml of supernatant was recovered. The recombinant antibody displayed all functional properties identified for the antibody isolated from the patient serum.

This same procedure was used to generate a recombinant supply of sHIgM12. An amino acid sequence analysis of sHIgM12 was obtained. Since the amino-terminus of the antibody heavy chain was blocked, Fv fragments were generated to increase the efficiency of obtaining an amino terminal sequence. The amino terminal sequence of the sHIgM12 heavy chain was determined to be Val-Gln-Leu-Gln-Glu-Ser-Gly-Pro-Gly-Leu-Leu-Lys-Pro-Ser-Glu-Thr-Leu-Arg/Ser-Leu-Thr-Asn (SEQ ID NO:4), while the amino terminal sequence of the light chain was determined to be Asp-Ile-Gln-Met-Thr-Gln-Ser-Pro-Ser-Ser-Leu-Ser-Ala-Ser-Val-Gly-Asp-Arg-Val (SEQ ID NO:5).

cDNA was isolated from the patient's peripheral blood cells, to be used for recovering full length cDNA copies of the mRNA encoding sHIgM12. In order to ensure than recovered cDNAs truly represented the antibody of interest, the amino acid sequences of CDR3 regions of sHIgM12 were determined. This was accomplished by proteolytic digestion of the Fv fragments and conventional amino acid sequencing of the digestion products. Once the sHIgM12 cDNAs were obtained, they were inserted into a vector that was similar to that described above but was modified for expression of IgM/Kappa antibodies by substituting the light chain constant region. Recombinant sHIgM12 then was expressed in the human/mouse hybridoma line F3B6 as described above. Amino acid sequences for the variable (Vk) and constant (Ck) domains of the sHIgM12 light chain are set forth in SEQ ID NOS:6 and 7, respectively. Amino acid sequences for the variable (Vh) and constant (CH1, CH2, CH3, and CH4) domains of the sHIgM12 heavy chain are set forth, respectively, in SEQ ID NOS:8, 9, 10, 11, and 12. These amino acid sequences also are provided in FIGS. 19A and 19B. Nucleotide sequences encoding the variable regions of the sHIgM12 light and heavy chains are shown in FIG. 20 (SEQ ID NOS:13 and 14, respectively). The modified vector also was used successfully to express the human antibody rHIgM46.

Example 15

Materials and Methods for Allergic Asthma Experiments

Mice and Reagents: Six to eight week-old BALBc/J and BALB/c-Stat4$^{tm1Gru}$ mice were obtained from Jackson Laboratory. OVA protein was purchased from Sigma Aldrich (St. Louis, Mo.).

Immunization and airway challenge: The sensitization and challenge procedure with OVA was modified from the method described by Zhang et al. ((1997) *Am. J. Respir. Crit. Care. Med.* 155:661-669). Briefly, all mice were sensitized by an intraperitoneal (i.p.) injection of 100 μg OVA adsorbed to 1 mg of alum (Pierce, Rockford, Ill.) on day 0. For the therapeutic regimen, mice received a second i.p. injection of 100 μg OVA adsorbed to alum on day 7. Experimental mice were intranasally challenged with 100 μg OVA in PBS under tribromoethanol anesthesia on days 14, 23, 24, 25 and 26.

Treatment with B7-DC cross-linking antibody: In the prophylactic regimen, mice were treated intravenously with sHIgM12 or the control polyclonal IgM (pHIgM) antibody at 10 μg per day on days −1, 0, and 1 relative to the first sensitization with OVA in alum. This schedule was designed to determine whether antibody treatment would prevent or reduce the establishment of a Th2 polarized response, which typically is elicited by the use of alum as an adjuvant. In the therapeutic regimen, the antibody treatments were carried out at the same dose and route on the day prior to the first intranasal challenge, the day of challenge, and the day after challenge with OVA in PBS (days 13, 14, and 15 relative to the first sensitization with OVA in alum). This treatment schedule was designed to assess whether treatment with B7-DC cross-linking antibody after immunization with a Th2 polarizing regimen could modulate an established response polarity.

Measurement of airway responsiveness to methacholine: Airway responsiveness was assessed on day 27 by methacholine-induced airflow obstruction in conscious mice in a whole body plethysmograph (Buxco Electronics, Troy, N.Y.). Pulmonary airflow obstruction was measured by enhanced pause (Penh) with a transducer connected to preamplifier modules and analyzed by system software. To measure methacholine responsiveness, mice were exposed for 2 minutes to PBS, followed by incremental dosages of aerosolised methacholine (Sigma Aldrich, St Louis, Mo.). Penh was monitored for each dose.

Collection of bronchoalveolar lavage (BAL) fluid: Immediately after measuring AHR, animals were injected i.p. with a lethal dose (250 mg/kg) of pentobarbital (Abbott Laboratories, Abbott Park, Ill.). The trachea was cannulated and the lungs were lavaged twice with 0.5 ml of HBSS. After centrifugation, the supernatant was collected and stored at −20° C. The cells were resuspended and counted using a hemocytometer. BAL cell differentials were determined with Wright-Giemsa stain; ≧200 cells were differentiated using conventional morphologic criteria. IL-5 in the BAL fluid supernatants was measured by ELISA as directed by the manufacturer (R&D Systems, Minneapolis, Minn.).

Histology: After BAL fluid collection, lungs were fixed in 10% formalin and embedded in paraffin. Sections were prepared and stained with Hematoxylin and Eosin. Some sections also were used for immunohistochemistry studies with an anti-CD3 antibody and a peroxidase-labeled secondary developing reagent. The sections were evaluated by microscopy at 100× and 400× magnification.

In vitro cytokine production and measurement of proliferation: On day 27, splenocytes from mice treated with the control antibody or sHIgM12 were harvested and processed. Briefly, after making a single cell suspension, red blood cells were lysed by hypertonic shock using ACK (ammonium chloride/potassium bicarbonate/EDTA). Cells were counted and resuspended at 3×10$^6$ cells/ml in RPMI (Cambrex Biosci, Walkersville, Md.). OVA at a concentration of 2 mg/ml was titrated at half log dilutions. Splenocytes were added at 3×10$^5$ cells in 100 Supernatants were harvested after 48 hours and stored for cytokine assay. Cells were pulsed with $^3$H-thymidine (Packard, Boston, Mass.) during the last 18 hours of the 72 hours assay. Cells were collected and counted for incorporation of $^3$H-thymidine. Stored supernatants were analyzed for IL-4, IL-5, IL-10, IFN-γ, and TNF-α by ELISA according to the protocol of the manufacturer (R&D Systems).

Statistical analysis: Data were analyzed using a two way repeated measures ANOVA or the Student T test for normally distributed data and the Whitney-Rank sum test for nonparametric data.

Example 16

Figure 16B:
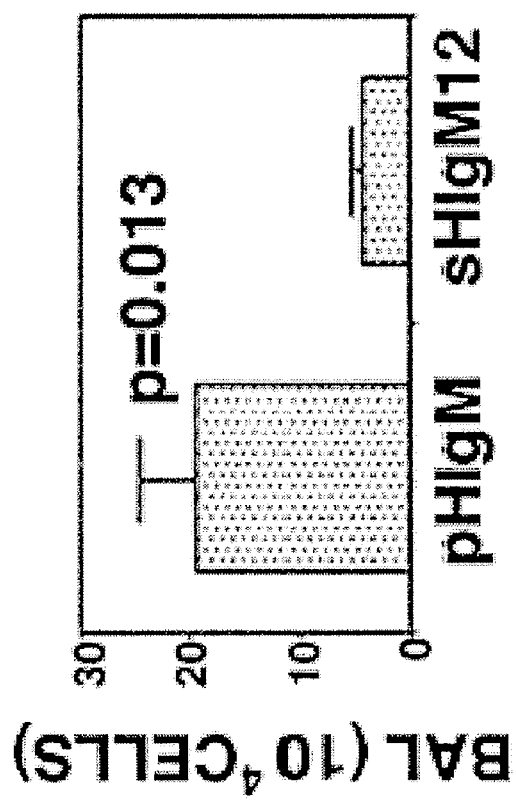
FIG. 16B is a graph plotting the number of cells present in bronchoalveolar lavage (BAL) fluid after methacholine challenge of mice that received either the control antibody or sHIgM12 as indicated. Data represent as mean±SEM, and n=10/group.
Figure 16A:
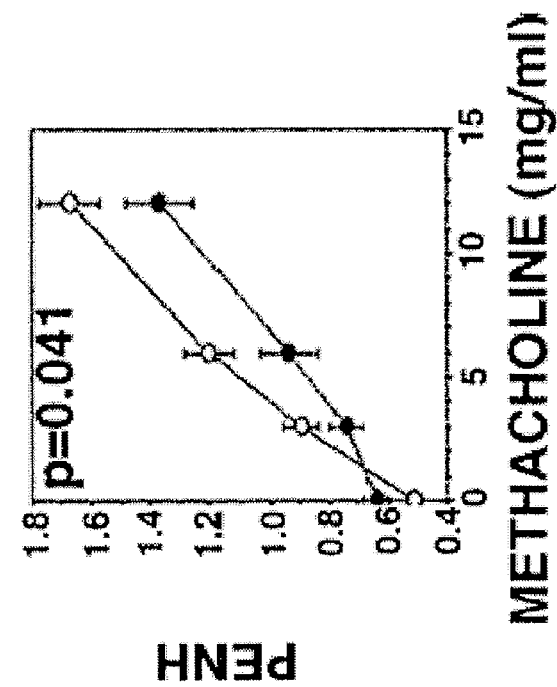
FIG. 16A is a graph plotting airway hyperreactivity (AHR) as measured by PENH in response to methacholine challenge of mice that received either the isotype control polyclonal IgM antibody (open circles) or the B7-DC cross-linking antibody sHIgM12 (filled circles). Data represent as mean±SEM, and n=10 per group.

Treatment with sHIgM12 Reduces Bronchial AHR in a Murine Model of Allergic Airway Inflammation Experiments were conducted to determine whether cross linking of B7-DC on murine DC with sHIgM12 antibody resulted in an immune response skewed away from the pathogenic Th2 phenotype that can be induced by immunization with the adjuvant alum. In particular, the effect of sHIgM12 on the asthma-like condition induced during initial immunization with OVA was analyzed. sHIgM12 was administered to mice starting one-day prior to, the day of, and one day after immunization with OVA in alum, as depicted in the protocol timeline of FIG. 15A. Mice treated with the sHIgM12 antibody were significantly protected from airway hyperresponsiveness (AHR) to methacholine challenge relative to animals treated with isotype control antibodies (FIG. 16A, p=0.041).

Figure 16D:
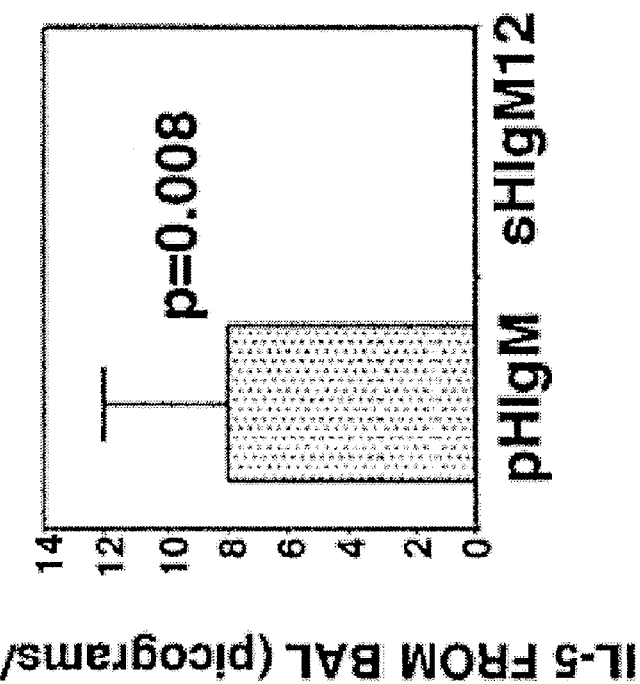
FIG. 16D is a graph plotting the level of IL-5 in BAL fluid obtained after methacholine challenge of mice that received either the control antibody or sHIgM12 as indicated. Data represent as mean±SEM, and n=10/group.
Figure 16C:
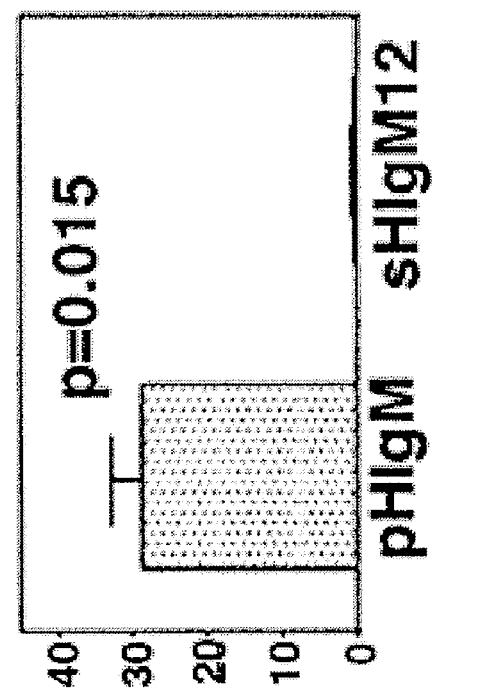
FIG. 16C is a graph plotting the percentage of eosinophils with respect to the total number of cells counted in BAL fluid obtained after methacholine challenge of mice that received either the control antibody or sHIgM12 as indicated.

The OVA model of allergic asthma is characterized by pulmonary inflammation reflected by an increase in the number of total cells in the BAL, an increase in the number of eosinophils in the lungs and BAL, and perivascular and peribronchial cellular infiltrates in lung tissue sections (Zhang et al., supra). The number of total cells in the BAL fluid was significantly reduced in sHIgM12 treated mice (FIG. 16B, p=0.013). Moreover, sHIgM12 treatment also resulted in dramatically reduced eosinophil migration to the lungs (FIG. 16C, p=0.015). IL-5 is a cytokine that plays a pivotal role in migration of eosinophils (Macatonia et al. (1995) *J. Immunol.* 154:5071-5079). The failure to detect significant eosinophilic infiltrates correlated with the observation of reduced levels of IL-5 following treatment with sHIgM12 antibody (FIG. 16D, p=0.008). Most striking was the finding that sHIgM12 treatment totally abrogated lung inflammation, the thickening of bronchial epithelium, and the accompanying accumulation of mucus plugs that were readily evident in mice treated with isotype control antibodies.

Example 17

Therapeutic Treatment with sHIgM12 Reduces Development of AHR

Figure 17B:
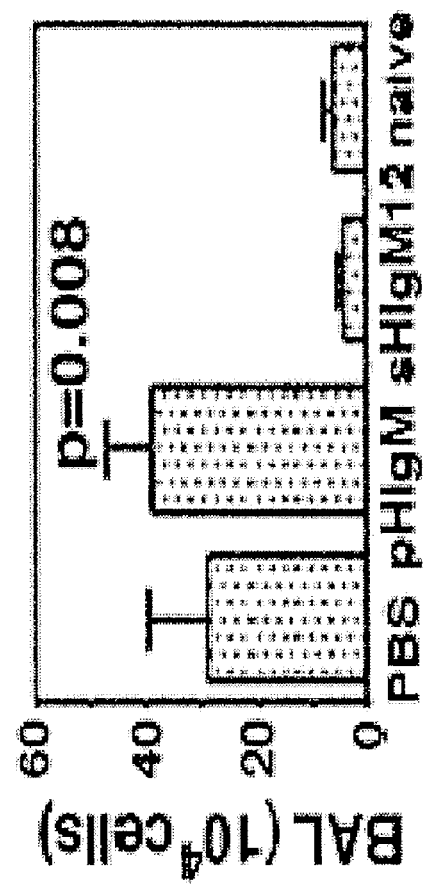
FIG. 17B is a graph plotting the number of cells in BAL fluid after methacholine challenge of normal mice and mice that received either PBS, control antibody, or sHIgM12 as indicated. Data represent mean±SEM. n=5 in the antibody treated groups. n=3 in normal and PBS treated groups.
Figure 17A:
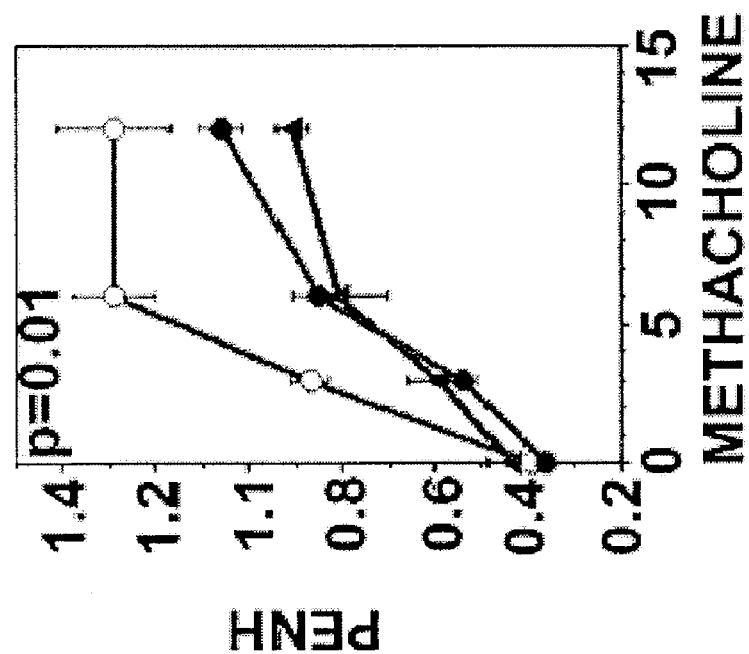
FIG. 17A is a graph plotting AHR as measured by PENH in response to methacholine challenge of mice that received either the isotype control polyclonal IgM antibody (open circles) or the B7-DC cross-linking antibody sHIgM12 (filled circles) 13 days after administration of antigen or of normal mice (filled triangles). Data represent mean±SEM, and n=5 per group.
Figure 17D:
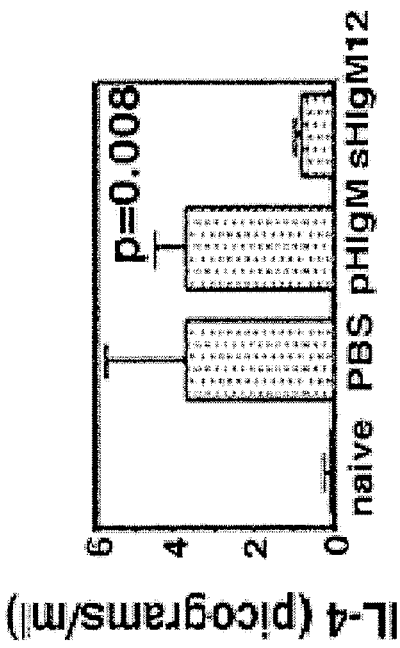
FIG. 17D is a graph plotting the levels of IL-4 in the lungs of methacholine challenged normal mice and mice that received either PBS, control antibody, or sHIgM12 as indicated.
Figure 17C:
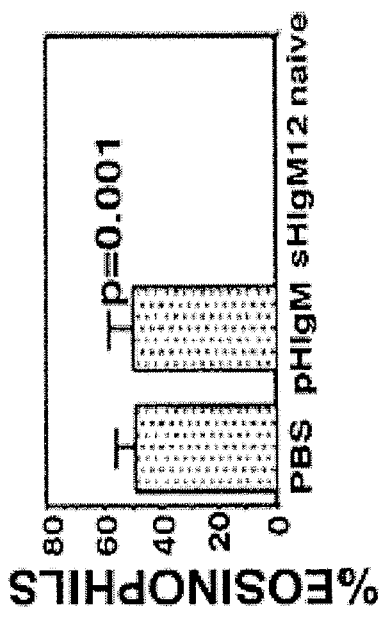
FIG. 17C is a graph plotting the percentage of eosinophils with respect to the total number of cells counted in BAL fluid obtained after methacholine challenge of normal mice and mice that received either PBS, control antibody, or sHIgM12 as indicated.

To determine whether treatment with sHIgM12 treatment could reduce development of allergic airway inflammatory disease in a therapeutic mouse model, mice were treated with sHIgM12 antibody on days 13, 14 and 15 following initial sensitization with OVA in alum adjuvant, as depicted in the protocol regimen of FIG. 15B. This regimen of treatment provided an opportunity to assess the potential of sHIgM12 antibody to modulate established T cell immune reactivity in a setting where the immune response was already skewed toward a pathogenic Th2 polarity. Mice that received the sHIgM12 antibody showed dramatic reduction in airway responsiveness to methacholine (FIG. 17A, p=0.01) relative to animals that received isotype control antibody. Moreover, the number of cellular infiltrates observed in the BAL of sHIgM12-treated mice was comparable to the number recovered in normal mice, and was significantly lower than the number of cellular infiltrates found in BAL from either the control antibody or the PBS treated mice (FIG. 17B, p=0.008). Similar to the findings with the prophylactic treatment regimen, there was no detectable eosinophilic infiltration in the mice treated therapeutically with sHIgM12 antibody (FIG. 17C, p=0.001).

Figure 17E:
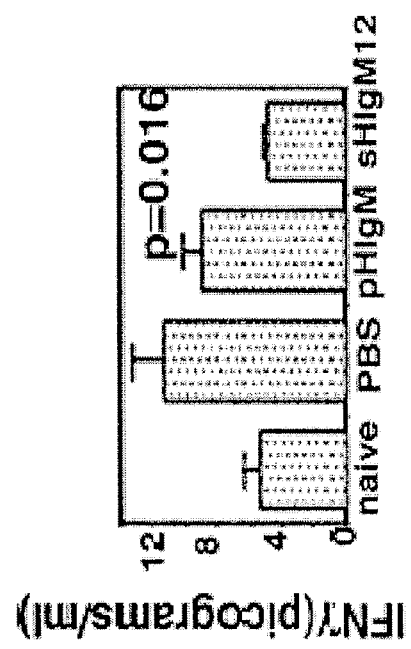
FIG. 17E is a graph plotting the levels of IFN-γ in the lungs of methacholine challenged normal mice and mice that received either PBS, control antibody, or sHIgM12 as indicated. Data represent mean±SEM. n=5 for antibody treated groups. n=3 for normal or PBS treated groups.

To further characterize the T cell response pattern, supernatants from the homogenized lungs of the various groups of mice were analyzed for the prototypic Th1 cytokine, IFN-γ, and the Th2 cytokine, IL-4. Mice that received sHIgM12 showed significantly reduced amounts of both IL-4 (FIG. 17D, p=0.008) and IFN-γ (FIG. 17E, p=0.016) in comparison to the control antibody treated mice. While IL-5 levels were not measured in this experiment, the complete absence of eosinophilia indicated that IL-5 levels also were low in the sHIgM12-treated animals. This cytokine pattern suggested that sHIgM12 treatment does not lead to a proinflammatory cytokine environment in the lungs by switching the polarity of the T cell response from Th2 to Th1, but rather blocks the development of either kind of T cell response. Immunohistochemistry analysis of lung tissue using a CD3-specific antibody as a probe supported this conclusion. Few T cells were present in the lungs of naïve animals. In contrast, lungs from mice treated with PBS or polyclonal IgM control antibody contained extensive T cell infiltrates. Remarkably, the lungs from sHIgM12 treated mice showed no signs of inflammation, similar to the lungs of untreated mice. In addition, there was no lung pathology in animals that received the therapeutic treatment protocol of sHIgM12 antibody 14 days after pre-sensitization; the lungs of naïve animals and sHIgM12 antibody treated mice were indistinguishable. In contrast, animals that were treated with PBS or isotype control antibody exhibited severe distortion of their bronchial airways and substantial inflammatory infiltration.

To determine whether the IL-12 signaling pathway is important for in vivo therapeutic effects of sHIgM12 antibody treatment, the ability of sHIgM12 to modulate inflammatory airway disease was assessed in Stat4 deficient animals. Stat 4 is a requisite intermediary that mediates IL-12 signaling (Jacobson et al. (1995) *J. Exp. Med.* 181:1755-1762). Stat 4 deficient animals are known to develop highly polarized Th2 responses, as their ability to develop immune responses with Th1 character is severely compromised by the mutation (Kaplan et al. (1996) *Nature* 382:174-177; and Thierfelder et al. (1996) *Nature* 382:171-174). In these experiments, the severity of induced airway inflammatory disease was substantially greater in Stat 4 deficient animals as compared to wild type mice. Therapeutic treatment of Stat 4 deficient animals with sHIgM12 had no effect, while in the same experiment wild type mice were completely protected from airway inflammatory disease. This finding indicates that the ability to mobilize the Stat 4 signaling molecule is critical for the effect of sHIgM12, and provides evidence that IL-12 production may be important for altering the polarity of the response by pre-sensitized animals.

Example 18

Treatment with sHIgM12 Alters Cytokine Production

In the absence of inflammation in the lungs of sHIgM12-treated animals, splenocytes from antibody treated animals were examined in vitro for the nature of their recall response to OVA challenge, to determine whether the Th2 polarity characteristic of an allergic response was altered toward a Th1 polarity. Mice were treated with sHIgM12 antibody or isotype control antibody on days 13, 14 and 15 post-sensitization with OVA in Alum adjuvant. Splenocytes were harvested at day 28 and were restimulated in vitro with OVA. The proliferative response of T cells in response to antigen was enhanced 10-fold in mice that had received sHIgM12 treatment in comparison to the control antibody treatment (FIG. 18A). This finding was consistent with the previous observation that treatment of DC with sHIgM12 enhances the ability to stimulate T cells (Radhakrishnan et al., supra). These experiments also demonstrated the potential of the sHIgM12 antibody to stimulate cellular responses against isolated proteins, an observation that may have important implications for the development of vaccines.

Figure 18B:
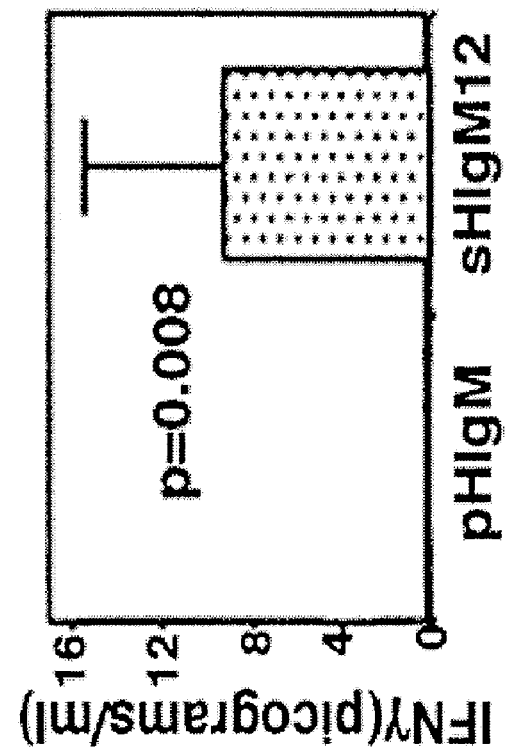
FIGS. 18B-18F are graphs plotting the levels of cytokine production by splenocytes that were harvested from the two groups of mice and restimulated in vitro with OVA. Data represent mean±SEM, and n=5.
Figure 18A:
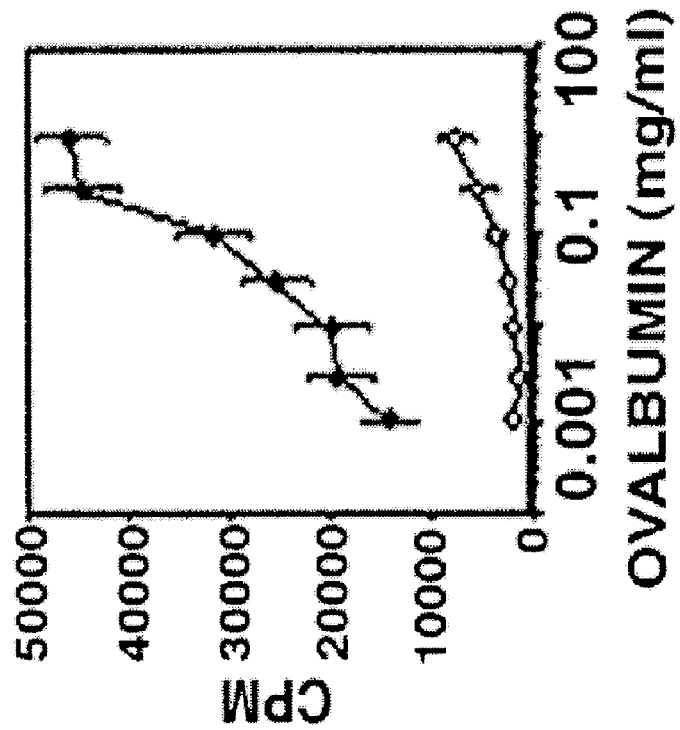
FIG. 18A is a graph plotting proliferation of splenocytes as measured by incorporation of $^3$[H]-thymidine into cells that were harvested from control (open circles) or sHIgM12 (filled circles) treated mice and stimulated in vitro with titrating amounts of OVA protein. Data represent mean±SEM, and n=5.
Figure 18D:
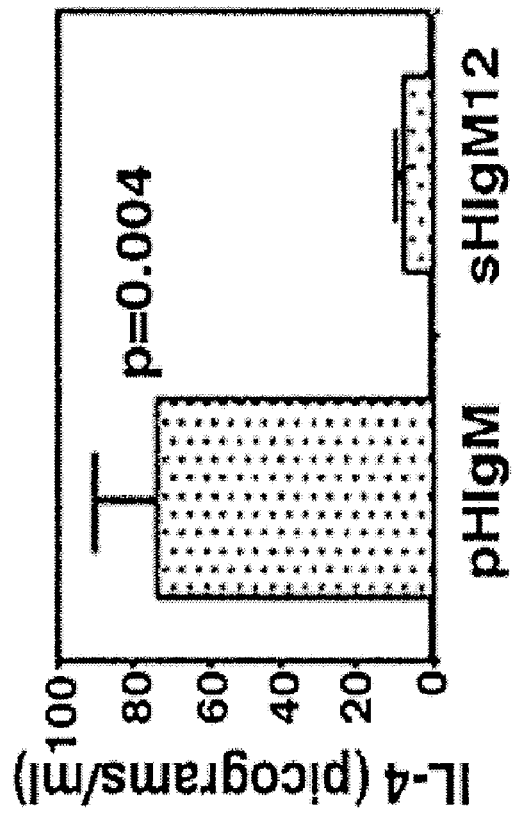
Figure 18C:
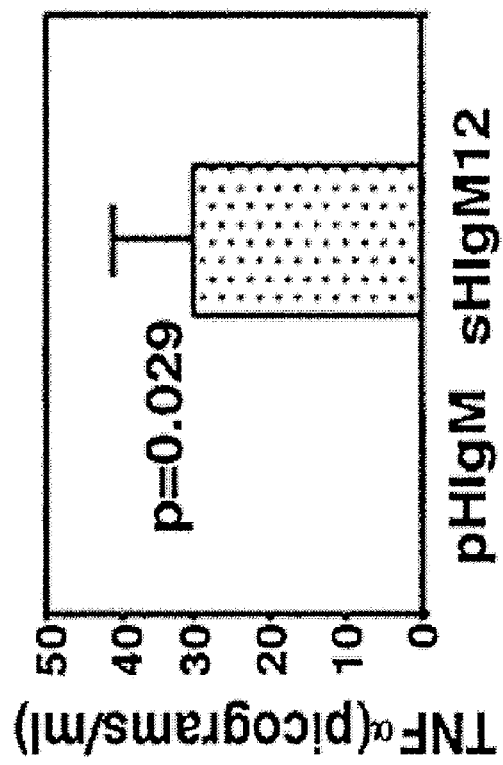
Figure 18F:
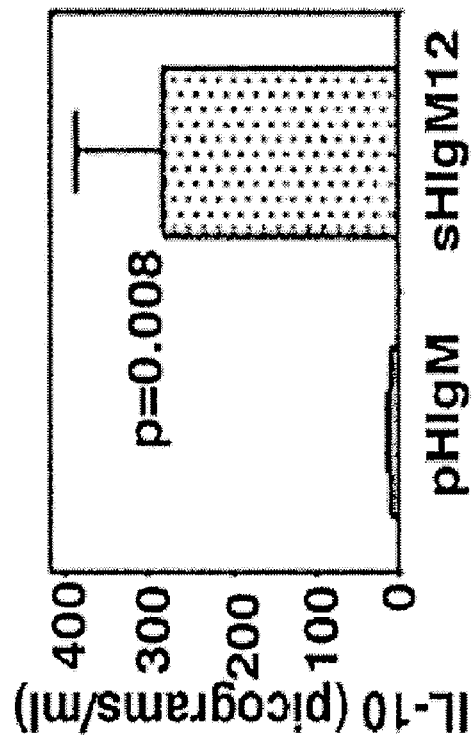
Figure 18E:
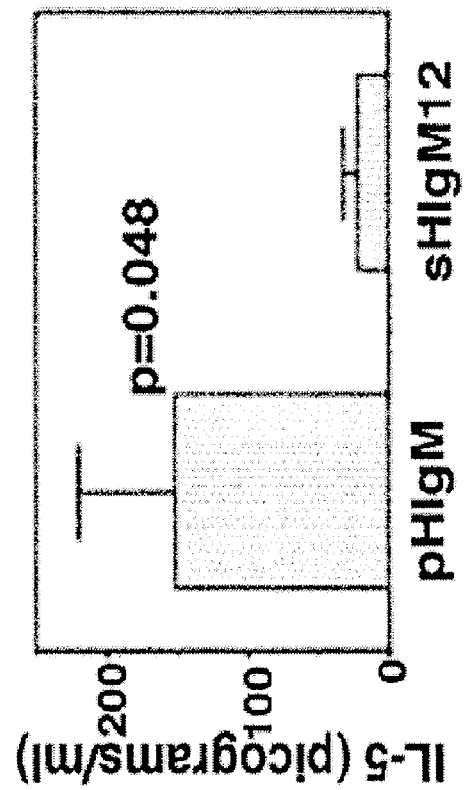

In further studies, supernatants from the stimulated cultures were harvested and tested for the presence of cytokines Although mice that received sHIgM12 produced significantly higher levels of INF-γ than mice treated with isotype control antibody, neither treatment group produced substantial levels of this cytokine (FIG. 18B, p=0.008). The same trend was observed for TNF-α production. Splenocytes from mice treated with sHIgM12 secreted small amounts of TNF-α, while no TNF-α was detected in supernatants from splenocytes treated with control antibody (FIG. 18C, p=0.029). In contrast to these Th1 cytokines, the prototypic Th2 cytokines IL-4 and IL-5 were substantially lower in cultures from mice treated with sHIgM12 antibody. Splenic cultures from mice treated with sHIgM12 contained very small quantities of IL-4 (FIG. 18D, p=0.004) and IL-5 (FIG. 18E, p=0.048). These data indicate that sHIgM12 skews the T cell response toward a Th1 polarity, but that even the Th1 response remains weak despite a strong proliferative response to secondary antigen challenge. The presence of substantial levels of IL-10 in secondary cultures pre-treated with sHIgM12 (FIG. 18F, p=0.008) might explain the absence of inflammation in the lungs of mice challenged intranasally with experimental allergen. In spite of the ability of T cells in these animals to secrete IFN-γ and TNF-α, T regulatory cells might dampen this tendency and inhibit the cytokines from tracking to the lungs. Taken together, these data support the notion that sHIgM12 treatment protects pre-sensitized individuals from allergic airway inflammatory disease by reducing a Th2 type of environment, and by promoting secretion of the anti-inflammatory cytokine, IL-10.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An isolated and recombinantly produced monoclonal antibody comprising a light chain variable domain amino acid sequence as set forth in SEQ ID NO:6, and a heavy chain variable domain amino acid sequence as set forth in SEQ ID NO:8.

2. The isolated antibody of claim 1 wherein said antibody further comprises a light chain constant domain amino acid sequence that comprises the amino acid sequence set forth in SEQ ID NO:7, and heavy chain constant domain CH1, CH2, CH3 and CH4 amino acid sequences of SEQ ID NO:9, SEQ ID NO:10, SEQ ID NO:11, and SEQ ID NO:12, respectively.

3. The isolated antibody of claim 1 wherein the antibody is an IgM antibody.

4. A monomeric fragment of the antibody of claim 3.

5. An Fab fragment, $F(ab)_2$ fragment, or single chain Fv fragment of the antibody of claim 1.

6. A composition comprising the isolated antibody of any of claim 1, 2 or 3 and a pharmaceutically acceptable carrier.

* * * * *